(12) United States Patent
Rheinheimer et al.

(10) Patent No.: US 9,271,501 B2
(45) Date of Patent: Mar. 1, 2016

(54) USE OF STROBILURIN TYPE COMPOUNDS FOR COMBATING PHYTOPATHOGENIC FUNGI RESISTANT TO QO INHIBITORS

(71) Applicants: Joachim Rheinheimer, Ludwigshafen (DE); Violeta Terteryan, Mannheim (DE); Stefan Redlich, Mannheim (DE); Doris Kremzow, Heidelberg (DE); Claudia Rosenbaum, Einhausen (DE); Sebastian Georgios Rohrer, Neckarsteinach (DE); Wassilios Grammenos, Ludwigshafen (DE); Christian Pilger, Ludwigshafen (DE); Franz Roehl, Goennheim (DE); Markus Gewehr, Kastellaun (DE); Gerd Stammler, Dossenheim (DE); Jurith Montag, Ludwigshafen (DE); Hubert Sauter, Baiersbronn (DE)

(72) Inventors: Joachim Rheinheimer, Ludwigshafen (DE); Violeta Terteryan, Mannheim (DE); Stefan Redlich, Mannheim (DE); Doris Kremzow, Heidelberg (DE); Claudia Rosenbaum, Einhausen (DE); Sebastian Georgios Rohrer, Neckarsteinach (DE); Wassilios Grammenos, Ludwigshafen (DE); Christian Pilger, Ludwigshafen (DE); Franz Roehl, Goennheim (DE); Markus Gewehr, Kastellaun (DE); Gerd Stammler, Dossenheim (DE); Jurith Montag, Ludwigshafen (DE); Hubert Sauter, Baiersbronn (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/364,532

(22) PCT Filed: Dec. 6, 2012

(86) PCT No.: PCT/EP2012/074586
§ 371 (c)(1),
(2) Date: Jun. 11, 2014

(87) PCT Pub. No.: WO2013/092224
PCT Pub. Date: Jun. 27, 2013

(65) Prior Publication Data
US 2014/0323305 A1    Oct. 30, 2014

(30) Foreign Application Priority Data

Dec. 21, 2011 (EP) .................... 11195032
Oct. 26, 2012 (EP) .................... 12190109

(51) Int. Cl.

| | | |
|---|---|---|
| *A01N 47/12* | (2006.01) | |
| *A01N 37/50* | (2006.01) | |
| *A01N 47/28* | (2006.01) | |
| *A01N 47/24* | (2006.01) | |
| *A01N 43/08* | (2006.01) | |
| *A01N 43/76* | (2006.01) | |
| *A01N 43/713* | (2006.01) | |
| *A01N 43/80* | (2006.01) | |
| *A01N 43/90* | (2006.01) | |
| *A01N 43/54* | (2006.01) | |
| *A01N 43/653* | (2006.01) | |
| *C07D 231/22* | (2006.01) | |
| *C07D 249/12* | (2006.01) | |
| *A01N 43/56* | (2006.01) | |
| *A01N 43/78* | (2006.01) | |
| *A01N 43/82* | (2006.01) | |
| *A01N 43/88* | (2006.01) | |

(52) U.S. Cl.
CPC ................ *A01N 47/12* (2013.01); *A01N 37/50* (2013.01); *A01N 43/08* (2013.01); *A01N 43/54* (2013.01); *A01N 43/56* (2013.01); *A01N 43/653* (2013.01); *A01N 43/713* (2013.01); *A01N 43/76* (2013.01); *A01N 43/78* (2013.01); *A01N 43/80* (2013.01); *A01N 43/82* (2013.01); *A01N 43/88* (2013.01); *A01N 43/90* (2013.01); *A01N 47/24* (2013.01); *A01N 47/28* (2013.01); *C07D 231/22* (2013.01); *C07D 249/12* (2013.01)

(58) Field of Classification Search
CPC ....... A01N 47/12; A01N 47/24; A01N 47/28; A01N 43/08; A01N 43/54; A01N 43/56; A01N 43/653; A01N 43/76; A01N 43/78; A01N 43/80; A01N 43/82; A01N 43/88; A01N 43/713; A01N 43/90; A01N 37/50; C07D 231/22; C07D 249/12
See application file for complete search history.

Structural Models of G143A mutant binding site

Pyraclostrobin (denoted F500 here)    compound I-6 (denoted compound 6 here)

The commercially available strobilurin analogue compound Pyraclostrobin modelled into an artificial cytochrome bc1 complex Qo-binding site displays steric clash of the phenyl ring with the 143A methyl group as indicated by arrow in the upper right part of the picture (left). Compound I-6 according to the present invention does not show a steric clash (right).

(56) References Cited

U.S. PATENT DOCUMENTS

| | | | |
|---|---|---|---|
| 6,583,090 B1 | 6/2003 | Gewehr et al. | |
| 2009/0306142 A1* | 12/2009 | Carson | A01N 37/24 514/336 |

FOREIGN PATENT DOCUMENTS

| | | |
|---|---|---|
| DE | 199 00 571 | 7/1999 |
| EP | 0 398 692 | 11/1990 |
| WO | WO 96/36229 | 11/1996 |
| WO | WO 98/21174 | 5/1998 |
| WO | WO 99/46246 | 9/1999 |
| WO | WO 2007/048735 | 5/2007 |
| WO | WO 2009/155095 | 12/2009 |

OTHER PUBLICATIONS

Schobert, Rainer et al., "Reactions of chelated $\eta^3$-pentadienyl iron complexes with nucleophiles", Journal of Organometallic Chemistry, 2004, p. 575-584, vol. 689, Search Report.

European Search Report dated Sep. 28, 2012, prepared in International Application No. 11195032.

International Search Report dated Mar. 1, 2013, prepared in International Application No. PCT/EP2012/074586.

International Preliminary Report on Patentability dated Jun. 24, 2014, prepared in International Application No. PCT/EP2012/074586.

* cited by examiner

*Primary Examiner* — Jane C Oswecki

(74) *Attorney, Agent, or Firm* — Brinks Gilson & Lione

(57) ABSTRACT

The present invention relates to the use of strobilurine type compounds of formula I and the N-oxides and the salts thereof for combating phytopathogenic fungi containing a mutation in the mitochondrial cytochrome b gene conferring resistance to Qo inhibitors, and to methods for combating such fungi. The invention also relates to novel compounds, processes for preparing these compounds, to compositions comprising at least one such compound, to plant health applications, and to seeds coated with at least one such compound.

20 Claims, 1 Drawing Sheet

Structural Models of G143A mutant binding site

Pyraclostrobin
(denoted F500 here)

compound I-6
(denoted compound 6 here)

The commercially available strobilurin analogue compound Pyraclostrobin modelled into an artificial cytochrome $bc_1$ complex Qo-binding site displays steric clash of the phenyl ring with the 143A methyl group as indicated by arrow in the upper right part of the picture (left). Compound I-6 according to the present invention does not show a steric clash (right).

USE OF STROBILURIN TYPE COMPOUNDS FOR COMBATING PHYTOPATHOGENIC FUNGI RESISTANT TO QO INHIBITORS

This application is a National Stage application of International Application No. PCT/EP2012/074586, filed Dec. 6, 2012, the entire contents of which is hereby incorporated herein by reference. This application also claims priority under 35 U.S.C. §119 to European Patent Application No. 11195032.5, filed Dec. 21, 2011, and to European Patent Application No. 12190109.4, filed Oct. 26, 2012, the entire contents of both of which are hereby incorporated herein by reference.

The present invention relates to the use of strobilurine type compounds of formula I and the N-oxides and the salts thereof for combating phytopathogenic fungi containing a mutation in the mitochondrial cytochrome b gene conferring resistance to Qo inhibitors, and to methods for combating such fungi. The invention also relates to novel compounds, processes for preparing these compounds, to compositions comprising at least one such compound, to plant health applications, and to seeds coated with at least one such compound.

Qo inhibitor fungicides, often referred to as strobilurin-type fungicides (Sauter 2007: Chapter 13.2. Strobilurins and other complex III inhibitors. In: Kramer, W.; Schirmer, U. (Ed.)—Modern Crop Protection Compounds. Volume 2. Wiley-VCH Verlag 457-495), are conventionally used to control a number of fungal pathogens in crops. Qo inhibitors typically work by inhibiting respiration by binding to a ubihydroquinone oxidation center of a cytochrome $bc_1$ complex (electron transport complex III) in mitochondria. Said oxidation center is located on the outer side of the inner mitochrondrial membrane. A prime example of the use of Qo inhibitors includes the use of, for example, strobilurins on wheat for the control of *Septoria tritici* (also known as *Mycosphaerella graminicola*), which is the cause of wheat leaf blotch. Unfortunately, widespread use of such Qo inhibitors has resulted in the selection of mutant pathogens which are resistant to such Qo inhibitors (Gisi et al., Pest Manag Sci 56, 833-841, (2000). Resistance to Qo inhibitors has been detected in several phytopathogenic fungi such as *Blumeria graminis, Mycosphaerella fijiensis, Pseudoperonspora cubensis* or *Venturia inaequalis*. Although several resistance mechanisms have been detected meanwhile (e.g. Jabs et al. Phytomedizin 31, 15-16 (2001); Olaya et al., Pestic Sci 54, 230-236 (1998), the major part of resistance to Qo inhibitors in agricultural uses has been attributed to pathogens containing a single amino acid residue substitution G143A in the cytochrome b gene for their cytochrome $bc_1$ complex, the target protein of Qo inhibitors. See, for example, Lucas, Pestic Outlook 14 (6), 268-70 (2003); and Fraaije et al., Phytopathol 95 (8), 933-41 (2005), (which both are expressly incorporated by reference herein). Thus, new methods and compositions are desirable for controlling pathogen induced diseases in crops comprising plants subjected to pathogens that are resistant to Qo inhibitors. Furthermore, in many cases, in particular at low application rates, the fungicidal activity of the known fungicidal strobilurin analogue compounds is unsatisfactory, especially in case that a high proportion of the fungal pathogens contain a mutation in the mitochondrial cytochrome b gene conferring resistance to Qo inhibitors. Based on this, it was also an object of the present invention to provide compounds having improved activity and/or a broader activity spectrum against phytopathogenic harmful fungi.

"Qo inhibitor," as used herein, includes any substance that is capable of diminishing and/or inhibiting respiration by binding to a ubihydroquinone oxidation center of a cytochrome $bc_1$ complex in mitochondria. The oxidation center is typically located on the outer side of the inner mitochrondrial membrane.

From WO 2009/155095, the use of a Qi inhibitor UK2A of formula

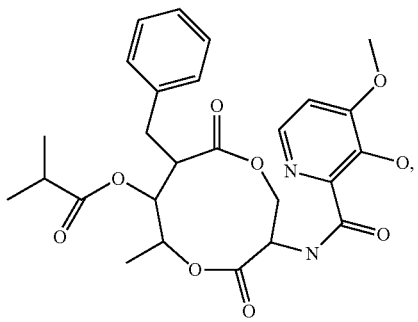

is known for combating phytopathogenic fungi that are resistant to Qo inhibitors. Qi inhibitors typically work by inhibiting respiration by binding to a ubihydroquinone oxidation center of a cytochrome bc1 complex in mitochondria, the said oxidation center being located on the inner side of the inner mitochrondrial membrane.

The strobilurin-analogue compounds according to the present invention differ from those described in the abovemention publication by the specific formula I and by inhibiting respiration by binding to a ubihydroquinone oxidation center of a cytochrome bc1 complex in mitochondria which defines them as Qo inhibitors. Besides the strobilurin analogue-specific structural elements $R^4$, these compounds contain two specific carbon atoms bound by a double bond wherein the groups $R^1$ and $R^2$ are cis-oriented or the $R^1$ and $R^2$ together with the abovementioned two carbon atoms linking them form a phenyl ring if $R^4$ is 4-methyl-1,4-dihydro-tetrazol-5-on-1-yl.

Accordingly, the present invention relates to the use of compounds of formula I

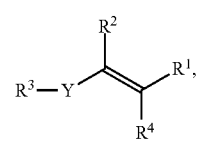

I wherein:
$R^1$, $R^2$ independently of each other are hydrogen, halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl or $C_3$-$C_6$-cycloalkyl-$C_1$-$C_4$-alkyl, wherein the groups $R^1$ and $R^2$ are cis-oriented, or
$R^1$ and $R^2$ together with the two carbon atoms linking them form a phenyl ring provided that $R^4$ is 4-methyl-1,4-dihydro-tetrazol-5-one-1-yl (formula R4-7), and
  wherein the aliphatic moieties of $R^1$ and/or $R^2$ or the abovementioned phenyl ring may carry 1, 2, 3 or up to the maximum number of identical or different groups $R^a$ which independently of one another are selected from:
$R^a$ halogen, CN, nitro, $C_1$-$C_4$-alkyl, $C_1$-$C_4$-alkoxy, $C_1$-$C_4$-haloalkyl and $C_1$-$C_4$-haloalkoxy;

Y is a direct bond or a divalent group selected from —OCH$_2$—, —CH$_2$—, —CH$_2$CH$_2$—, —C(Z)=N—O—CH$_2$—, —CHZ—C(Z)=N—O—CH$_2$—, —O—N=C(Z)—C(Z)=N—O—CH$_2$—, —C(=O)—C(Z)=N—O—CH$_2$— and —C(=N—O—Z)—C(Z)=N—O—CH$_2$—, where the bond depicted on the left side of the divalent group Y is attached to R$^3$, and the bond depicted on the right side is attached to the carbon atom being substituted by R$^2$, and Z, which may be the same or different to any other Z, is hydrogen, C$_1$-C$_4$-alkyl or C$_1$-C$_4$-haloalkyl;

R$^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group of N, O and S;

wherein the cyclic groups R$^3$ may carry 1, 2, 3, 4 or up to the maximum possible number of identical or different groups R$^b$ which independently of one another are selected from:

R$^b$, which may be the same or different to any other R$^b$, is amino, halogen, hydroxyl, oxo, nitro, CN, carboxyl, C$_1$-C$_4$-alkyl, C$_2$-C$_4$-alkenyl, C$_2$-C$_4$-alkynyl, C$_1$-C$_4$-haloalkyl, C$_1$-C$_4$-alkoxy, C$_1$-C$_4$-haloalkoxy, C$_3$-C$_6$-cycloalkyl, C$_3$-C$_6$-cycloalkenyl, C$_2$-C$_6$-alkenyloxy, C$_3$-C$_6$-alkynyloxy, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_1$-C$_4$-alkylamino, C$_1$-C$_4$-alkoxycarbonyl, C$_1$-C$_4$-alkylcarbonyloxy, phenyl, naphthyl or a 3- to 10-membered saturated, partially unsaturated or aromatic mono- or bicyclic heterocyclyl which, in addition to carbon atoms, contains one to four heteroatoms from the group consisting of N, O and S as ring members; and wherein the aforementioned phenyl and heterocyclyl groups R$^b$ are attached via a direct bond, an oxygen or sulfur atom, and two radicals R$^b$ that are bound to adjacent ring member atoms of the cyclic group R$^3$ may form together with said ring member atoms a fused 5-, 6- or 7-membered saturated, partially unsaturated or aromatic cycle, which may be a carbocycle or heterocycle, wherein the ring member atoms of the heterocycle include besides carbon atoms 1, 2, 3 or 4 heteroatoms selected from the group of N, O and S, and where the aliphatic or cyclic groups R$^b$ for their part may carry 1, 2, 3 or up to the maximum possible number of identical or different groups R$^c$:

R$^c$, which may be the same or different to any other R$^c$, is halogen, hydroxyl, nitro, CN, carboxyl, C$_1$-C$_4$-alkyl, C$_2$-C$_4$-alkenyl, C$_2$-C$_8$-alkynyl, C$_1$-C$_4$-haloalkyl, C$_1$-C$_4$-alkoxy, C$_1$-C$_4$-haloalkoxy, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_1$-C$_6$-alkoxyimino-, C$_2$-C$_6$-alkenyloxyimino-, C$_2$-C$_6$-alkynyloxyimino-, C$_2$-C$_6$-haloalkenyloxyimino-, C$_3$-C$_6$-cycloalkyl, C$_3$-C$_6$-cycloalkenyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups R$^c$ are attached via a direct bond, an oxygen or sulfur atom, and where the aliphatic or cyclic groups R$^c$ for their part may carry 1, 2, 3 or up to the maximum possible number of identical or different groups R$^d$:

R$^d$, which may be the same or different to any other R$^d$, is halogen, C$_1$-C$_4$-alkyl or C$_1$-C$_4$-haloalkyl;

or

R$^3$ is —CR$^A$=N—O—R$^B$, wherein

R$^A$ is amino, hydroxyl, C$_1$-C$_4$-alkyl, C$_2$-C$_4$-alkenyl, C$_2$-C$_4$-alkynyl, C$_1$-C$_4$-haloalkyl, C$_1$-C$_4$-alkoxy, C$_1$-C$_4$-haloalkoxy, C$_3$-C$_6$-cycloalkyl, C$_3$-C$_6$-cycloalkenyl, C$_2$-C$_6$-alkenyloxy, C$_3$-C$_6$-alkynyloxy, C$_1$-C$_4$-alkoxyimino-C$_1$-C$_4$-alkyl, C$_1$-C$_4$-alkylamino, C$_1$-C$_4$-alkoxycarbonyl, C$_1$-C$_4$-alkylcarbonyloxy, phenyl, phenyl-C$_1$-C$_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned cyclic R$^A$ are attached via a direct bond, an oxygen or sulfur atom;

R$^B$ is C$_1$-C$_4$-alkyl, C$_2$-C$_4$-alkenyl, C$_2$-C$_4$-alkynyl, C$_1$-C$_4$-haloalkyl, C$_3$-C$_6$-cycloalkyl, C$_3$-C$_6$-cycloalkenyl, C$_1$-C$_4$-alkoxyimino-C$_1$-C$_4$-alkyl, C$_1$-C$_4$-alkoxycarbonyl, phenyl, phenyl-C$_1$-C$_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members;

where the aliphatic or cyclic groups R$^A$ and/or R$^B$ for their part may carry 1, 2, 3 or up to the maximum possible number of identical or different groups R$^e$:

R$^e$, which may be the same or different to any other R$^e$, is halogen, hydroxyl, nitro, CN, carboxyl, C$_1$-C$_4$-alkyl, C$_2$-C$_4$-alkenyl, C$_2$-C$_8$-alkynyl, C$_1$-C$_4$-haloalkyl, C$_1$-C$_4$-alkoxy or C$_1$-C$_4$-haloalkoxy;

R$^4$ is a monovalent group selected from formulae R4-1 to R4-7

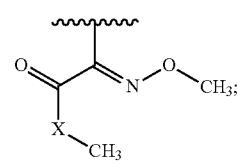

R4-1

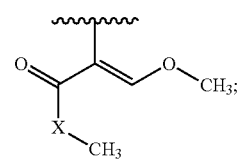

R4-2

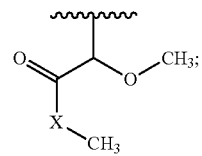

R4-3

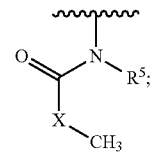

R4-4

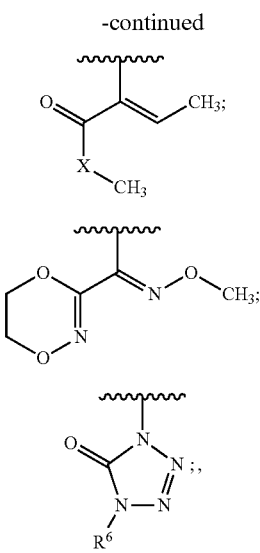

wherein the jagged line defines the point of attachment, and
X is a direct bond or a divalent group $CH_2$, O or NH,
$R^5$ is $C_1$-$C_4$-alkyl, $C_1$-$C_4$-alkoxy, $C_1$-$C_4$-haloalkyl, $C_1$-$C_4$-haloalkoxy or $C_3$-$C_6$-cycloalkyl,
$R^6$ is $C_1$-$C_4$-alkyl or $C_1$-$C_4$-haloalkyl;
and the N-oxides and the agriculturally acceptable salts thereof, for combating phytopathogenic fungi containing a mutation in the mitochondrial cytochrome b gene conferring resistance to Qo inhibitors.

Furthermore, the present invention also relates to methods for combating phytopathogenic fungi containing a mutation in the mitochondrial cytochrome b gene conferring resistance to Qo inhibitors using the abovementioned compounds of formula I.

Certain strobilurin type compounds of formula I, wherein $R^4$ is 1-methoxycarbonyl-2-methoxy-ethen-1-yl (defined as R4-2 herein, wherein X is O) and $R^1$ is $CF_3$, are mentioned in WO 1998/021174: (E)-2-[1-methoxy-meth-(E)-ylidene]-5-(4-phenoxy-phenoxy)-3-trifluoromethyl-pent-3-enoic acid methyl ester (CAS No. 207852-99-1); (E)-2-[1-methoxy-meth-(E)-ylidene]-5-(3-phenoxy-phenoxy)-3-trifluoromethyl-pent-3-enoic acid methyl ester (207853-00-7); (E)-2-[1-methoxy-meth-(E)-ylidene]-4-methyl-5-(3-phenoxy-phenoxy)-3-trifluoromethyl-pent-3-enoic acid methyl ester; and (E)-5,5,5-trifluoro-2-[1-methoxy-meth-(E)-ylidene]-3-methyl-4-(4-phenoxy-phenoxymethyl)-pent-3-enoic acid methyl ester. However, it is not mentioned that the strobilurine type compounds inhibit fungal pathogens containing a mutation in the mitochondrial cytochrome b gene conferring resistance to Qo inhibitors. II Further, preparation of the compound (2E,3Z)-2-(ethylidene)-5-phenyl-3-pentenoic acid methyl ester (CAS-No. 681026-20-0) has been described in J Organomet Chem 689, 575-584 (2004).

Further, certain strobilurin type compounds, wherein $R^1$ and $R^2$ together with the two carbon atoms linking them form a phenyl ring and wherein $R^4$ is 1-methyl-1,4-dihydro-tetrazole-5-one-4-yl (R4-7) are known inter alia from WO 1996/036229, WO 1999/046246 and DE 199 00 571 A1.

The compounds according to the present invention differ from those described in the abovementioned publications that $R^1$ and $R^2$ do not form with the two carbon atoms linking them a phenyl ring, and that (E)-2-[1-methoxy-meth-(E)-ylidene]-5-(4-phenoxy-phenoxy)-3-trifluoromethyl-pent-3-enoic acid methyl ester (207852-99-1); (E)-2-[1-methoxy-meth-(E)-ylidene]-5-(3-phenoxy-phenoxy)-3-trifluoromethyl-pent-3-enoic acid methyl ester (207853-00-7); (E)-2-[1-methoxy-meth-(E)-ylidene]-4-methyl-5-(3-phenoxy-phenoxy)-3-trifluoromethyl-pent-3-enoic acid methyl ester; (E)-5,5,5-trifluoro-2-[1-methoxy-meth-(E)-ylidene]-3-methyl-4-(4-phenoxy-phenoxymethyl)-pent-3-enoic acid methyl ester; and (2E,3Z)-2-(ethylidene)-5-phenyl-3-pentenoic acid methyl ester (CAS-No. 681026-20-0) are excluded.

Therefore, according to a second aspect, the invention provides compounds of formula I which are represented by formula I

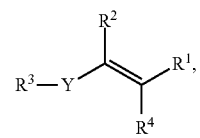

wherein:
$R^1$, $R^2$ independently of each other are hydrogen, halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl or $C_3$-$C_6$-cycloalkyl-$C_1$-$C_4$-alkyl, wherein the groups $R^1$ and $R^2$ are cis-oriented,
  wherein the aliphatic moieties of $R^1$ and/or $R^2$ may carry 1, 2, 3 or up to the maximum number of identical or different groups $R^a$ which independently of one another are selected from:
  $R^a$ halogen, CN, nitro, $C_1$-$C_4$-alkyl, $C_1$-$C_4$-alkoxy, $C_1$-$C_4$-haloalkyl and $C_1$-$C_4$-haloalkoxy;
Y is a direct bond or a divalent group selected from —$OCH_2$—, —$CH_2$—, —$CH_2CH_2$—, —C(Z)=N—O—$CH_2$—, —CHZ—C(Z)=N—O—$CH_2$—, —O—N=C(Z)—C(Z)=N—O—$CH_2$—, —C(=O)—C(Z)=N—O—$CH_2$— and —C(=N—O—Z)—C(Z)=N—O—$CH_2$—,
  where the bond depicted on the left side of the divalent group Y is attached to $R^3$, and the bond depicted on the right side is attached to the carbon atom being substituted by $R^2$, and
  Z, which may be the same or different to any other Z, is $C_1$-$C_4$-alkyl or $C_1$-$C_4$-haloalkyl;
$R^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group of N, O and S;
  wherein the cyclic groups $R^3$ may carry 1, 2, 3, 4 or up to the maximum possible number of identical or different groups $R^b$ which independently of one another are selected from:
  $R^b$, which may be the same or different to any other $R^b$, is amino, halogen, hydroxyl, oxo, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, naphthyl or a 3- to 10-membered saturated, partially unsaturated or aromatic mono- or bicyclic heterocyclyl or which, in addition to carbon atoms, contains one to four heteroatoms from the group consisting of N, O and S as ring members; and wherein the aforementioned phenyl and heterocyclyl groups $R^b$ are attached via a direct bond, an oxygen or sulfur atom;
and
two radicals $R^b$ that are bound to adjacent ring member atoms of the cyclic group $R^3$ may form together with said ring member atoms a fused 5-, 6- or 7-membered saturated, partially unsaturated or aromatic cycle, which may be a carbocycle or heterocycle, wherein the ring member atoms of the fused heterocycle include besides carbon atoms 1, 2, 3 or 4 heteroatoms selected from the group of N, O and S, and where the aliphatic or cyclic groups $R^b$ for their part may carry 1, 2, 3 or up to the maximum possible number of identical or different groups $R^c$:
$R^c$, which may be the same or different to any other $R^c$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkoxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups $R^c$ are attached via a direct bond, an oxygen or sulfur atom and where the aliphatic or cyclic groups $R^c$ for their part may carry 1, 2, 3 or up to the maximum possible number of identical or different groups $R^d$:
$R^d$, which may be the same or different to any other $R^d$, is halogen, $C_1$-$C_4$-alkyl or $C_1$-$C_4$-haloalkyl;
or
$R^3$ is —$CR^A$=N—O—$R^B$, wherein
$R^A$ is amino, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_4$-alkoxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, phenyl-$C_1$-$C_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned cyclic $R^A$ are attached via a direct bond, an oxygen or sulfur atom;
$R^B$ is $C_1$-$C_4$-alkyl, $C_2$-$C_4$-alkenyl, $C_2$-$C_4$-alkynyl, $C_1$-$C_4$-haloalkyl, $C_3$-$C_6$-cycloalkyl, $C_3$-$C_6$-cycloalkenyl, $C_1$-$C_4$-alkoxyimino-$C_1$-$C_4$-alkyl, $C_1$-$C_4$-alkoxycarbonyl, phenyl, phenyl-$C_1$-$C_4$-alkyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members;
where the aliphatic or cyclic groups $R^A$ and/or $R^B$ for their part may carry 1, 2, 3 or up to the maximum possible number of identical or different groups $R^e$:
$R^e$, which may be the same or different to any other $R^e$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy or $C_1$-$C_4$-haloalkoxy;
$R^4$ is a monovalent group selected from formulae R4-1 to R4-7

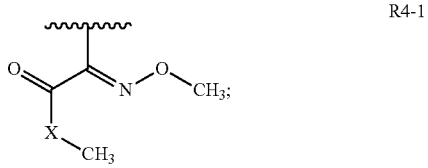

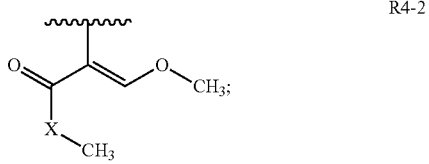

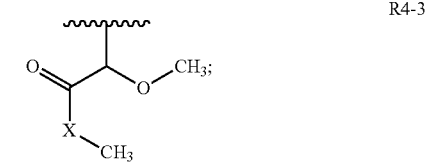

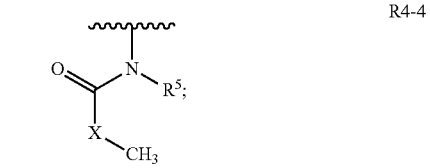

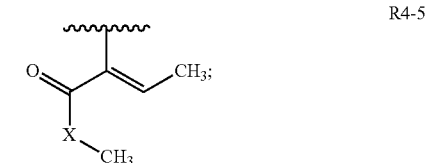

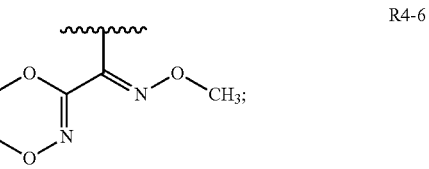

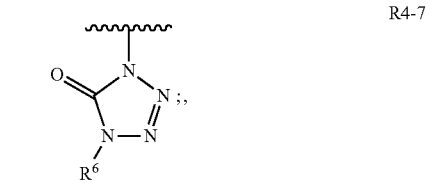

wherein the jagged line defines the point of attachment, and where
X is a divalent group O or NH,
$R^5$ is $C_1$-$C_4$-alkyl, $C_1$-$C_4$-alkoxy, $C_1$-$C_4$-haloalkyl, $C_1$-$C_4$-haloalkoxy or $C_3$-$C_6$-cycloalkyl,
$R^6$ is $C_1$-$C_4$-alkyl or $C_1$-$C_4$-haloalkyl;
and the N-oxides and the agriculturally acceptable salts thereof, except for (E)-2-[1-methoxy-meth-(E)-ylidene]-5-(4-phenoxy-phenoxy)-3-trifluoromethyl-pent-3-enoic acid methyl ester (207852-99-1), (E)-2-[1-methoxy-meth-(E)-ylidene]-5-(3-phenoxy-phenoxy)-3-trifluoromethyl-pent-3-enoic acid methyl ester (207853-00-7); (E)-2-[1-methoxy-meth-(E)-ylidene]-4-methyl-5-(3-phenoxy-phenoxy)-3-trifluoromethyl-pent-3-enoic acid methyl ester, (E)-5,5,5- trifluoro-2-[1-methoxy-meth-(E)-ylidene]-3-methyl-4-(4-phenoxy-phenoxymethyl)-pent-3-enoic acid methyl ester, and (2E,3Z)-2-(ethylidene)-5-phenyl-3-pentenoic acid methyl ester (CAS-No. 681026-20-0).

The term "compounds I" refers to compounds of formula I. Likewise, this terminology applies to all sub-formulae, e.g. "compounds I.2" refers to compounds of formula I.2 or "compounds V" refers to compounds of formula V, etc.

The compounds I can be obtained by various routes in analogy to prior art processes known (e.g. WO 1998/021174, J Organomet Chem 689, 575-584 (2004), WO 1996/036229) and, advantageously, by the synthesis shown in the following schemes and in the experimental part of this application.

A suitable method to prepare compounds I is illustrated in scheme 1. It starts with the reduction of an acetylene compound II with a reducing agent like lithium aluminium hydride preferably in the presence of a solvent. Suitable solvents are inert against the reducing agent used and preferably selected from cyclic or aliphatic ethers like dietyl ether, tetrahydrofurane (THF), 1,4-dioxane, and methyl-tert.-butyl ether (MTBE). The reaction temperature can be between −40° C. and 100° C., preferably −20 to 60° C. After a reduced intermediate has been formed, a tin compound of formula III, wherein Alk defines a suitable alkyl residue like methyl, ethyl, n-propyl, or n-butyl and wherein L is a leaving group such as halogen, ethoxy and methoxy, in particular methoxy, is added. The resulting intermediate IV is a stable compound which can be isolated and purified with the usual methods (for example extraction and chromatography).

Compound IV is further reacted with compound V to yield the intermediate VI applying the usual methods for coupling aliphatic alcohols with hydroxyl compounds IV. The Mitsonobu reaction has proven especially useful.

Compound VI is then coupled with compound VII, wherein LG is a leaving group, preferably being halogen (except fluoro) or a sulfonyloxy group such as triflate, preferably in the presence of a suitable catalyst such as known transition metal catalysts, more preferably palladium catalysts, wherein the ligand may be trifuryl phoshine, triphenyl phosphine, tritolyl phosphine or bidentate phosphine ligands. The Copper compounds, such as $CuI_2$ can be added to improve the reaction. A wide variety of solvents is possible here, with THF, 1,4-dioxane and amides like dimethylformamide (DMF) being preferred. The reaction temperatures can be −20 to 150° C., preferably 20 to 120° C.

The resulting compounds I, wherein Y is —$OCH_2$— and $R^2$ is H, can be further modified. For example, if $R^4$ contains an ester group, VIII can be transformed into a methyl amide by reaction with methyl amine.

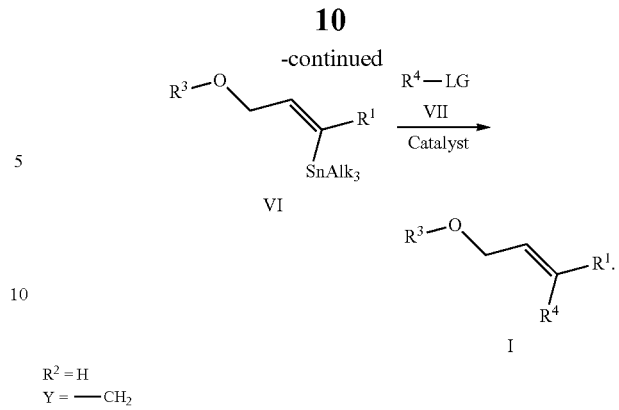

$R^2 = H$
$Y = ——CH_2$

Another general method to prepare compounds I is illustrated in scheme 2. The starting materials VIII are either known or can be prepared analogous to known compounds. The Wittig-Horner reaction of compounds VIII with compounds IX illustrated here (see also Tetrahedron Lett. 1988, 29, 3361) can be replaced by the Wittig reaction if this results in better yields. These reactions as well as the reaction conditions are well known. A specific problem is the E/Z-ratio in the newly formed double bond. The desired isomer is usually accompanied by some undesired isomer, which has to be removed by purification known in the art (e.g. chromatography, destillation, crystallization, etc.).

Scheme 2:

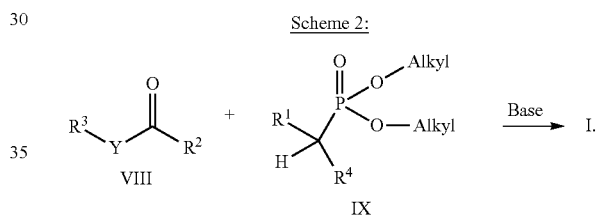

A route to compounds I, wherein $R^4$ is of formula R4-4, is illustrated in scheme 3. The compound X can be obtained for example from compound VI by direct reaction with iodine. The iodine in compounds X may be replaced by other suitable leaving groups, for example by bromine, chlorine or triflate. The sodium atom in the salt VII can be replaced by other suitable metal atoms, for example potassium, lithium, magnesium, calcium, etc. The coupling reaction of X and XI is performed preferably in the presence of a transition metal catalyst being preferably copper in the presence of a nitrogen containing ligand system (see e.g.: Tetrahedron Lett 2008, 49 (26), 4196-4199; Org. Lett. 2004, 6 (11), 1809-1812).

Scheme 1:

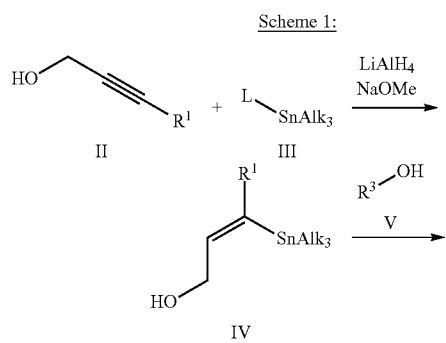

Scheme 3:

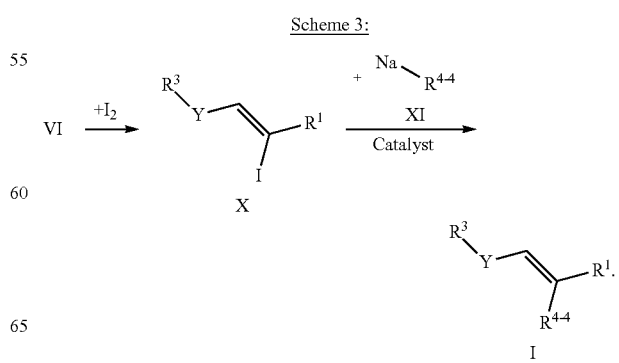

If individual compounds I cannot be obtained by the routes described above, they can be prepared by derivatization of other compounds I.

If the synthesis yields mixtures of isomers in the case of oximes, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl (isobutyl), 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_1$-$C_4$-alkyl" refers to a straight-chained or branched alkyl group having 1 to 4 carbon atoms.

The term "$C_1$-$C_4$-haloalkyl" refers to a straight-chained or branched alkyl group having 1 to 4 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. Likewise, the term "$C_1$-$C_6$-haloalkyl" refers to a straight-chained or branched alkyl group having 1 to 6 carbon atoms.

The term "$C_1$-$C_6$-alkoxy" refers to a straight-chain or branched alkyl group having 1 to 6 carbon atoms which is bonded via an oxygen, at any position in the alkyl group, e.g. $OCH_3$, $OCH_2CH_3$, $O(CH_2)_2CH_3$, 1-methylethoxy, $O(CH_2)_3CH_3$, 1-methylpropoxy, 2-methylpropoxy or 1,1-dimethylethoxy, $O(CH_2)_4CH_3$ or $O(CH_2)_5CH_3$. Likewise, the term "$C_1$-$C_4$-alkoxy" refers to a straight-chain or branched alkyl group having 1 to 4 carbon atoms which is bonded via an oxygen, at any position in the alkyl group.

The term "$C_1$-$C_4$-haloalkoxy" refers to a $C_1$-$C_4$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, $OC_2F_5$, 2-fluoropropoxy, 3-fluoropropoxy, 2,2-difluoropropoxy, 2,3-difluoro-propoxy, 2-chloropropoxy, 3-chloropropoxy, 2,3-dichloropropoxy, 2-bromo-propoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromo-ethoxy, 4-fluorobutoxy, 4-chlorobutoxy, 4-bromobutoxy or nonafluorobutoxy. Likewise, the term "$C_1$-$C_6$-haloalkoxy" refers to a $C_1$-$C_6$-alkoxy group as defined above, wherein some or all of the hydrogen atoms may be replaced by halogen atoms as mentioned above.

The term "$C_1$-$C_4$-alkoxy-$C_1$-$C_4$-alkyl" refers to alkyl having 1 to 4 carbon atoms, wherein one hydrogen atom of the alkyl radical is replaced by a $C_1$-$C_4$-alkoxy group. Likewise, the term "$C_1$-$C_6$-alkoxy-$C_1$-$C_6$-alkyl" refers to alkyl having 1 to 6 carbon atoms, wherein one hydrogen atom of the alkyl radical is replaced by a $C_1$-$C_6$-alkoxy group.

The term "$C_1$-$C_4$-alkylamino" refers to an amino radical carrying one $C_1$-$C_4$-alkyl group as substituent, e.g. methylamino, ethylamino, propylamino, 1-methylethylamino, butylamino, 1-methylpropylamino, 2-methylpropylamino, 1,1-dimethylethylamino and the like. Likewise, the term "$C_1$-$C_6$-alkylamino" refers to an amino radical carrying one $C_1$-$C_6$-alkyl group as substituent.

The term "di($C_1$-$C_4$-alkyl)amino" refers to an amino radical carrying two identical or different $C_1$-$C_4$-alkyl groups as substituents, e.g. dimethylamino, diethylamino, di-n-propylamino, diisopropylamino, N-ethyl-N-methylamino, N-(n-propyl)-N-methylamino, N-(isopropyl)-N methylamino, N-(n-butyl)-N-methylamino, N-(2-butyl)-N methylamino, N-(isobutyl)-N-methylamino, and the like. Likewise, the term "di($C_1$-$C_6$-alkyl)amino" refers to an amino radical carrying two identical or different $C_1$-$C_6$-alkyl groups as substituents.

The term "$C_1$-$C_4$-alkoxyimino" refers to a divalent imino radical ($C_1$-$C_4$-alkyl-O—N=) carrying one $C_1$-$C_4$-alkoxy group as substituent, e.g. methylimino, ethylimino, propylimino, 1-methylethylimino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms (as defined above), wherein two hydrogen atoms of one carbon atom of the alkyl radical are replaced by a divalent $C_1$-$C_6$-alkoxyimino radical ($C_1$-$C_6$-alkyl-O—N=) as defined above.

The term "$C_2$-$C_6$-alkenyloxyimino-$C_1$-$C_4$-alkyl" refers to alkyl having 1 to 4 carbon atoms (as defined above), wherein two hydrogen atoms of one carbon atom of the alkyl radical are replaced by a divalent $C_2$-$C_6$-alkenyloxyimino radical ($C_2$-$C_6$-alkenyl-O—N=).

The term "$C_2$-$C_6$-alkynyloxyimino-$C_1$-$C_4$-alkyl" refers to alkyl having 1 to 4 carbon atoms (as defined above), wherein two hydrogen atoms of one carbon atom of the alkyl radical are replaced by a divalent $C_2$-$C_6$-alkynyloxyimino radical ($C_2$-$C_6$-alkynyl-O—N=).

The term "$C_1$-$C_4$-alkylcarbonyl" refers to a $C_1$-$C_4$-alkyl radical which is attached via a carbonyl group. The term "($C_1$-$C_6$-alkoxy)carbonyl" refers to a $C_1$-$C_6$-alkoxy radical which is attached via a carbonyl group.

The term "$C_1$-$C_6$-alkylaminocarbonyl" refers to a $C_1$-$C_6$-alkylamino radical which is attached via a carbonyl group. Likewise, the term "di($C_1$-$C_6$-alkyl)aminocarbonyl" refers to a di($C_1$-$C_6$)alkylamino radical which is attached via a carbonyl group.

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl(allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, 1-propynyl, 2-propynyl, 1-butynyl, 2-butynyl, 3-butynyl, 1-methyl-2-propynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_6$-cycloalkyl" refers to monocyclic, bicyclic, saturated hydrocarbon radicals having 3 to 6 carbon ring members, such as cyclopropyl, cyclobutyl, cyclopentyl or cyclohexyl.

Likewise, the term "$C_3$-$C_6$-cycloalkenyl" refers to unsaturated hydrocarbon radicals having 3 to 6 carbon ring members and a double bond in any position, such as cyclopropenyl, cyclobutenyl, cyclopentenyl or cyclohexenyl.

The term "$C_3$-$C_6$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 6 carbon atoms.

The term "phenyl-$C_1$-$C_4$-alkyl" refers to alkyl having 1 to 4 carbon atoms (as defined above), wherein one hydrogen atom of the alkyl radical is replaced by a phenyl radical.

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae provided herein, e.g. formulae I.1 and I.2, and to the intermediates such as compounds II, III, IV and V, wherein the substituents and variables (such as k, $R^1$, $R^2$, $R^3$, $R^4$, $R^5$, $R^6$, X, Y, Z, $R^A$, $R^B$, $R^a$, $R^b$, $R^c$, $R^d$ and $R^e$) have independently of each other or more preferably in combination (any possible combination of 2 or more substituents as defined herein) the following meanings:

Preference is also given to the uses, methods, mixtures and compositions, wherein the definitions (such as phytopathogenic fungi, treatments, crops, compounds II, further active ingredients, solvents, solid carriers) have independently of each other or more preferably in combination the following meanings and even more preferably in combination (any possible combination of 2 or more definitions as provided herein) with the preferred meanings of compounds I herein:

According to one embodiment of the invention, the invention also relates to a method for combating phytopathogenic fungi containing a mutation in the mitochondrial cytochrome b gene conferring resistance to Qo inhibitors, comprising: treating the phytopathogenic fungi containing a mutation in the mitochondrial cytochrome b gene conferring resistance to Qo inhibitors or the materials, plants, the soil or seeds that are at risk of being diseased from phytopathogenic fungi containing a mutation in the mitochondrial cytochrome b gene conferring resistance to Qo inhibitors with an effective amount of at least one compound I, or a composition comprising it thereof.

The term "phytopathogenic fungi containing a mutation in the mitochondrial cytochrome b gene conferring resistance to Qo inhibitors" ist be understood that at least 10% of the fungal isolates to be controlled contain a mutation in the mitochondrial cytochrome b gene conferring resistance to Qo inhibitors, more preferably at least 30%, even more preferably at least 50%, and most preferably at least 75% of the fungi, in particular between 90 and 100%.

It has been observed under field conditions that populations of phytopathogenic fungi apparently consisting of non-resistant strains can readily develop resistance. The compounds can be applied under such conditions, too, in order to prevent the formation of resistance and the spread of resistant strains altogether. In this regard it is useful that they have strong activity against non-resistant phytopathogenic fungi also.

According to another embodiment, the method for combating phytopathogenic fungi, comprises: a) identifying the phytopathogenic fungi containing a mutation in the mitochondrial cytochrome b gene conferring resistance to Qo inhibitors, or the materials, plants, the soil or seeds that are at risk of being diseased from phytopathogenic fungi as defined herein, and b) treating said fungi or the materials, plants, the soil or seeds with an effective amount of at least one compound I, or a composition comprising it thereof.

According to another embodiment of the invention, the invention also relates to a method for combating phytopathogenic fungi containing a mutation in the mitochondrial cytochrome b gene conferring resistance to Qo inhibitors, comprising: treating the phytopathogenic fungi whereof at least 10% contain a mutation in the mitochondrial cytochrome b gene conferring resistance to Qo inhibitors or the materials, plants, the soil or seeds that are at risk of being diseased from phytopathogenic fungi containing a mutation in the mitochondrial cytochrome b gene conferring resistance to Qo inhibitors with an effective amount of at least one compound I, or a composition comprising it thereof; more preferably at least 30%, even more preferably at least 50%, and most preferably at least 75% of the fungi contain a mutation in the mitochondrial cytochrome b gene conferring resistance to Qo inhibitors.

According to one embodiment of the use and the method for combating phytopathogenic fungi, wherein the mutation in the mitochondrial cytochrome b gene of the phytopathogenic fungi is G143A.

According to another embodiment, the phytopathogenic fungi are selected from the group consisting of basidomycetes, ascomycetes, and oomycetes.

According to a further embodiment, the phytopathogenic fungi are selected from the group consisting of *Alternaria alternata, Blumeria graminis, Pyriculania oryzae* (also known as *Magnaporthe grisea*), *Septoria tritici* (also known as *Mycosphaerella graminicola*), *Mycosphaerella fijiensis, Venturia inaequalis, Pyrenophora teres, Pyrenophona tritici-repentis* and *Plasmopara viticola*, in particular *Septoria tritici.*

One embodiment of the invention relates to compounds I, wherein $R^1$ is halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl or $C_3$-$C_6$-cycloalkyl-$C_1$-$C_4$-alkyl, wherein the aliphatic moieties of $R^1$ may carry 1, 2, 3 or up to the maximum number of identical or different groups $R^b$ which independently of one another are selected from halogen, CN, nitro, $C_1$-$C_4$-alkyl, $C_1$-$C_4$-alkoxy, $C_1$-$C_4$-haloalkyl and $C_1$-$C_4$-haloalkoxy; more preferably $R^1$ is halogen, $C_1$-$C_4$-alkyl, $C_1$-$C_4$-haloalkyl, $C_1$-$C_4$-alkoxy, $C_1$-$C_4$-alkoxy-$C_1$-$C_4$-alkyl or $C_1$-$C_4$-haloalkoxy-$C_1$-$C_4$-alkyl; even more preferably $R^1$ is halogen, $C_1$-$C_4$-alkyl, $C_1$-$C_4$-chloroalkyl, $C_1$-$C_4$-alkoxy, $C_1$-$C_4$-alkoxy-$C_1$-$C_4$-alkyl or $C_1$-$C_4$-haloalkoxy-$C_1$-$C_4$-alkyl; in particular $C_1$-$C_4$-alkyl.

According to another embodiment, if $R^4$ is 1-methoxycarbonyl-2-methoxy-ethen-1-yl (R4-2, wherein X is O), $R^1$ cannot be $CF_3$.

According to a further embodiment, $R^2$ is hydrogen, halogen, $C_1$-$C_4$-alkyl, $C_1$-$C_4$-haloalkyl, $C_1$-$C_4$-alkoxy, $C_1$-$C_4$-alkoxy-$C_1$-$C_4$-alkyl or $C_1$-$C_4$-haloalkoxy-$C_1$-$C_4$-alkyl; more preferably $R^2$ is hydrogen, halogen, $C_1$-$C_4$-alkyl, $C_1$-$C_4$-alkoxy, or $C_1$-$C_4$-alkoxy-$C_1$-$C_4$-alkyl; even more preferably $R^2$ is hydrogen, $C_1$-$C_4$-alkyl or $C_1$-$C_4$-alkoxy; in particular hydrogen.

According to a further embodiment, $R^2$ is halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl or $C_3$-$C_6$-cycloalkyl-$C_1$-$C_4$-alkyl, wherein the aliphatic moieties of $R^2$ may carry 1, 2, 3 or up to the maximum number of identical or different groups $R^a$ which independently of one another are selected from halogen, CN, nitro, $C_1$-$C_4$-alkyl, $C_1$-$C_4$-alkoxy, $C_1$-$C_4$-haloalkyl and $C_1$-$C_4$-haloalkoxy.

According to a further embodiment, Z is hydrogen or methyl, in particular methyl.

According to a further embodiment, Y is a divalent group selected from $—OCH_2—$, $—CH_2—$, $—CH_2CH_2—$, $—C(CH_3){=}N—O—CH_2—$, $—O—N{=}C(CH_3)—C(CH_3){=}N—O—CH_2—$ and $—C({=}N—O—CH_3)—C(CH_3){=}N—O—CH_2—$; preferably $—OCH_2—$, $—CH_2CH_2—$, $—C(CH_3){=}N—O—CH_2—$, $—O—N{=}C(CH_3)—C(CH_3){=}N—O—CH_2—$ or $—C({=}N—O—CH_3)—C(CH_3){=}N—O—CH_2—$, where the bond depicted on the left side of the divalent group Y is attached to $R^3$, and the bond depicted on the right side is attached to the carbon atom being substituted by $R^2$; in particular Y is $—OCH_2$, which compounds are of formula I.1:

I.1

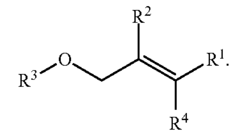

According to a further embodiment, Y is $—CH_2—$, which compounds are of formula I.2:

I.2

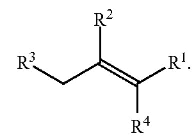

According to a further embodiment, Y is $—CH_2CH_2—$, which compounds are of formula I.3:

I.3

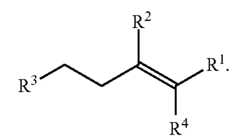

According to a further embodiment, Y is $—C(CH_3){=}N—O—CH_2—$, which compounds are of formula I.4:

I.4

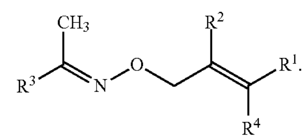

According to a further embodiment, Y is $—O—N{=}C(CH_3)—C(CH_3){=}N—O—CH_2—$, which compounds are of formula I.5:

I.5

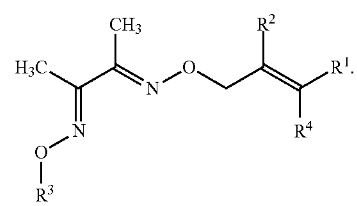

According to a further embodiment, Y is $—C({=}N—O—CH_3)—C(CH_3){=}N—O—CH_2—$, which compounds are of formula I.6:

I.6

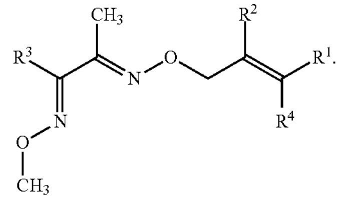

Particularly preferred embodiments of the invention relate to compounds I, wherein the group Y is one of the following radicals Y-1 to Y-10, where the bond depicted on the left side of the divalent group Y is attached to $R^3$, and the bond depicted on the right side is attached to the carbon atom being substituted by $R^2$:

| No. | Y |
|---|---|
| Y-1 | —OCH$_2$— |
| Y-2 | —CH$_2$— |
| Y-3 | —CH$_2$CH$_2$— |
| Y-4 | —C(CH$_3$)=N—O—CH$_2$— |
| Y-5 | —O—N=C(CH$_3$)—C(CH$_3$)=N—O—CH$_2$— |
| Y-6 | —C(=N—O—CH3)—C(CH3)=N—O—CH$_2$— |
| Y-7 | —CH$_2$—C(CH$_3$)=N—O—CH$_2$— |
| Y-8 | —C(=O)—C(CH$_3$)=N—O—CH$_2$— |
| Y-9 | —CH$_2$OCH$_2$— |
| Y-10 | —CH=N—O—CH$_2$— |

Particularly preferred embodiments of the invention relate to compounds I, wherein the group Y is —OCH$_2$—.

According to a further embodiment, $R^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group of N, O and S, wherein $R^3$ may carry 1, 2, 3, 4 or up to the maximum possible number of identical or different groups $R^b$ as defined herein; more preferably said 3- to 10-membered saturated, partially unsaturated or aromatic mono- or bicyclic heterocyclyl is a 5- to 6-membered heteroaryl wherein the ring member atoms of the heteroaryl include besides carbon atoms 1, 2 or 3 heteroatoms selected from the group of N, O and S.

According to a further embodiment, $R^3$ is phenyl, wherein the phenyl may carry 1, 2, 3, 4 or up to the maximum possible number of identical or different groups $R^b$ as defined herein.

According to a further embodiment, $R^3$ is a 5-membered-heteroaryl, wherein the ring member atoms of the heterocyclyl include besides carbon atoms 1, 2 or 3 heteroatoms selected from the group of N, O and S, wherein the heteroaryl may carry 1, 2, 3, 4 or up to the maximum possible number of identical or different groups $R^b$ as defined herein; more preferably said heteroaryl is pyrazolyl, imidazolyl, oxazolyl, isoxazolyl, thiazolyl, 1,2,4-triazolyl, 1,2,4-oxadiazolyl, 1,3,4-oxadiazolyl or 1,2,4-thiadiazolyl.

According to a further embodiment, $R^3$ is pyrazolyl, imidazolyl, oxazolyl, isoxazolyl, thiazolyl, 1,2,4-triazolyl, 1,2,4-oxadiazolyl, 1,3,4-oxadiazolyl or 1,2,4-thiadiazolyl, which is substituted by phenyl, wherein said phenyl may carry 1, 2, 3 or up to the maximum possible number of identical or different groups $R^c$, which may be the same or different to any other $R^c$, wherein $R^c$ is halogen, $C_1$-$C_4$-alkyl, $C_2$-$C_4$-alkenyl, $C_1$-$C_4$-haloalkyl, $C_1$-$C_4$-alkoxy, $C_1$-$C_4$-haloalkoxy, $C_1$-$C_4$-alkoxyimino-$C_1$-$C_4$-alkyl, phenyl or a 5-membered saturated, partially unsaturated or aromatic heterocyclyl which, in addition to carbon atoms, contains one to three heteroatoms from the group consisting of N, O and S as ring members; and wherein the aforementioned heterocyclyl groups $R^c$ are attached via a direct bond, an oxygen or sulfur atom and for their part may carry 1, 2, 3 or up to the maximum possible number of identical or different groups $R^d$ as defined herein.

According to a further embodiment, $R^3$ is a 6-membered-heteroaryl, wherein the ring member atoms of the heterocyclyl include besides carbon atoms 1, 2 or 3 heteroatoms selected from the group of N, O and S, wherein the heteroaryl may carry 1, 2, 3, 4 or up to the maximum possible number of identical or different groups $R^b$ as defined herein; more preferably said heteroaryl is pyridinyl or pyrimidinyl.

According to a further embodiment, $R^3$ carries 1, 2 or 3 identical or different groups $R^b$.

According to a further embodiment, $R^b$ independently of one another are selected from carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_1$-$C_4$-alkylamino, $C_1$-$C_4$-alkoxycarbonyl, $C_1$-$C_4$-alkylcarbonyloxy, phenyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned phenyl and heterocyclyl groups $R^b$ are attached via a direct bond, an oxygen or sulfur atom.

According to a further embodiment, the aliphatic or cyclic groups $R^b$ for their part carry 1, 2, 3 or up to the maximum possible number of identical or different groups $R^c$, which, may be the same or different to any other $R^c$, selected from halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy and $C_1$-$C_4$-haloalkoxy; more preferably $R^b$ for their part carry 1, 2 or 3 identical or different groups $R^c$.

According to a further embodiment, $R^c$, which, may be the same or different to any other $R^c$, is halogen, $C_1$-$C_4$-alkyl, $C_1$-$C_4$-haloalkyl, $C_1$-$C_4$-alkoxyimino-$C_1$-$C_4$-alkyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups $R^c$ are attached via a direct bond, an oxygen or sulfur atom and for their part may carry 1, 2, 3 or up to the maximum possible number of identical or different groups $R^d$ as defined herein.

According to a further embodiment, two radicals $R^b$ that are bound to adjacent ring member atoms of the cyclic group $R^3$ form together with said ring member atoms a fused 5-, 6- or 7-membered saturated, partially unsaturated or aromatic cycle, which may be a carbocycle or heterocycle, wherein the ring member atoms of the fused heterocycle include besides carbon atoms 1, 2, 3 or 4 heteroatoms selected from the group of N, O and S.

According to a further embodiment, $R^3$ is —$CR^A$=N—O—$R^B$, wherein $R^A$ is amino, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_4$-alkoxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned phenyl and heterocyclyl groups $R^A$ are attached via a direct bond, an oxygen or sulfur atom, where the aliphatic or cyclic groups $R^A$ may carry 1, 2, 3 or up to the maximum possible number of identical or different groups $R^e$, which may be the same or different to any other $R^e$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy or $C_1$-$C_4$-haloalkoxy.

According to a further embodiment, $R^3$ is —$CR^A$=N—O—$R^B$, wherein $R^B$ is hydroxyl, $C_1$-$C_4$-alkyl, $C_2$-$C_4$-alkenyl, $C_2$-$C_4$-alkynyl, $C_1$-$C_4$-haloalkyl, $C_3$-$C_6$-cycloalkyl, $C_3$-$C_6$-cycloalkenyl, $C_1$-$C_4$-alkoxyimino-$C_1$-$C_4$-alkyl$C_1$-$C_4$-alkoxycarbonyl, phenyl, naphthyl or a 3- to 10-membered saturated, partially unsaturated or aromatic mono- or bicyclic heterocyclyl or which, in addition to carbon atoms, contains one to four heteroatoms from the group consisting of O, N and S as ring members, where the aliphatic or cyclic groups $R^B$ may carry 1, 2, 3 or up to the maximum possible number of identical or different groups $R^e$, which may be the same or different to any other $R^e$, is halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy or $C_1$-$C_4$-haloalkoxy.

More preferably $R^A$ and $R^B$, independently of each other, are $C_1$-$C_4$-alkyl which may carry 1, 2, 3 or up to the maximum possible number of identical or different halogen; in particular $R^A$ and $R^B$ are methyl.

According to a further embodiment, the aliphatic or cyclic groups $R^A$ and/or $R^B$ for their part may carry 1, 2, 3 or up to the maximum possible number of identical or different groups $R^e$, more preferably they carry 0, 1 or 3 identical or different groups $R^e$. According to a further embodiment, $R^e$, which may be the same or different to any other $R^e$, is halogen, $C_1$-$C_4$-alkyl, $C_1$-$C_4$-haloalkyl, $C_1$-$C_4$-alkoxy or $C_1$-$C_4$-haloalkoxy.

According to a further embodiment, $R^4$ is —C(=NOCH$_3$)—CONHCH$_3$, —C(=NOCH$_3$)—COOCH$_3$, —C(=CHOCH$_3$)—COOCH$_3$, —C(=CHOCH$_3$)—CONHCH$_3$, —N(OCH$_3$)—COOCH$_3$, —N(CH$_3$)—COOCH$_3$ or —N(CH$_2$CH$_3$)—COOCH$_3$ According to a further embodiment, $R^4$ is R4-1 as defined herein, wherein X is O.
According to a further embodiment, $R^4$ is R4-1 as defined herein, wherein X is NH.
According to a further embodiment, $R^4$ is R4-2 as defined herein, wherein X is O.
According to a further embodiment, $R^4$ is R4-2 as defined herein, wherein X is NH.
According to a further embodiment, $R^4$ is R4-3 as defined herein, wherein X is O.
According to a further embodiment, $R^4$ is R4-3 as defined herein, wherein X is NH.
According to a further embodiment, $R^4$ is R4-4 as defined herein, wherein X is O.
According to a further embodiment, $R^4$ is R4-4 as defined herein, wherein X is NH.
According to a further embodiment, $R^5$ is $C_1$-$C_4$-alkyl, $C_1$-$C_4$-haloalkyl, $C_1$-$C_4$-alkoxy or $C_1$-$C_4$-haloalkoxy, more preferably $C_1$-$C_2$-alkyl or $C_1$-$C_2$-alkoxy, even more preferably methyl, ethyl or methoxy.
According to a further embodiment, $R^4$ is R4-4 as defined herein, wherein X is O and wherein $R^5$ is methyl, ethyl or methoxy.
According to a further embodiment, $R^4$ is R4-5 as defined herein, wherein X is O.
According to a further embodiment, $R^4$ is R4-5 as defined herein, wherein X is NH.
According to a further embodiment, $R^4$ is R4-6 as defined herein.
According to a further embodiment, $R^4$ is R4-7 as defined herein.

Further embodiments of the invention relate to compounds I, wherein the group $R^3$ is one of the following radicals R3-A to R3-B, wherein # indicates the point of attachment to the linker moiety Y:

| Line | $R^3$ |
|---|---|
| R3-A | (structure) |
| R3-B | (structure) |

Particularly preferred embodiments of the invention relate to compounds I, wherein the group $R^3$ is one of the following radicals R3-1 to R3-195, wherein # indicates the point of attachment to the linker moiety Y:

TABLE A

| Line | $R^3$ |
|---|---|
| R3-1 | (structure) |
| R3-2 | (structure) |
| R3-3 | (structure) |
| R3-4 | (structure) |
| R3-5 | (structure) |
| R3-6 | (structure) |
| R3-7 | (structure) |
| R3-8 | (structure) |

TABLE A-continued

| Line | R³ |
|---|---|
| R3-9 | 4-fluoro-3-methylphenyl-pyrazol-3-yl |
| R3-10 | 4-chloro-3-(trifluoromethyl)phenyl-pyrazol-3-yl |
| R3-11 | 3,4-dimethylphenyl-pyrazol-3-yl |
| R3-12 | 2,2-difluoro-1,3-benzodioxol-5-yl-pyrazol-3-yl |
| R3-13 | 4-bromophenyl-pyrazol-3-yl |
| R3-14 | 4-methoxyphenyl-pyrazol-3-yl |
| R3-15 | 4-ethoxyphenyl-pyrazol-3-yl |
| R3-16 | 4-(difluoromethoxy)phenyl-pyrazol-3-yl |
| R3-17 | 4-[1-(methoxyimino)ethyl]phenyl-pyrazol-3-yl |
| R3-18 | 4-phenoxyphenyl-pyrazol-3-yl |
| R3-19 | 3-chlorophenyl-pyrazol-3-yl |
| R3-20 | 3-(trifluoromethyl)phenyl-pyrazol-3-yl |
| R3-21 | 4-fluorophenyl-pyrazol-3-yl |
| R3-22 | 4-methylphenyl-pyrazol-3-yl |
| R3-23 | 4-ethylphenyl-pyrazol-3-yl |
| R3-24 | 4-(trifluoromethyl)phenyl-pyrazol-3-yl |

TABLE A-continued
| Line | R³ |
|---|---|
| R3-25 |  |
| R3-26 | 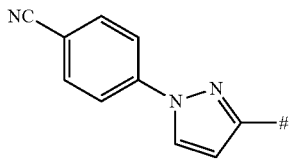 |
| R3-27 | 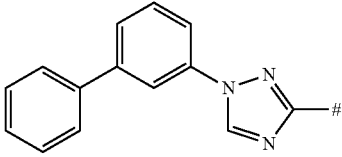 |
| R3-28 | 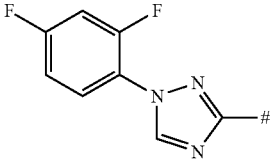 |
| R3-29 | 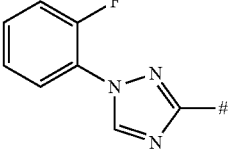 |
| R3-30 | 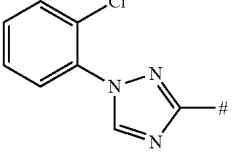 |
| R3-31 | 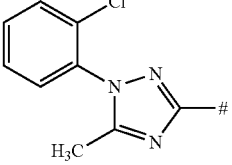 |
| R3-32 | 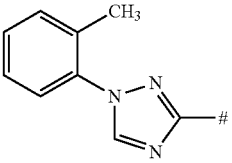 |
| R3-33 | 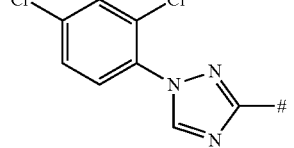 |
| R3-34 | 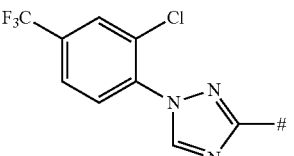 |
| R3-35 | 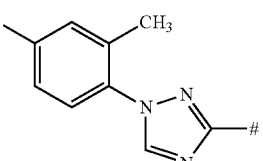 |
| R3-36 | 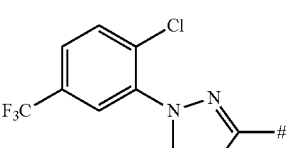 |
| R3-37 | 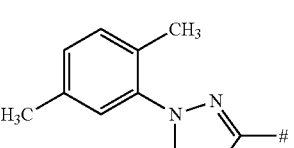 |
| R3-38 | 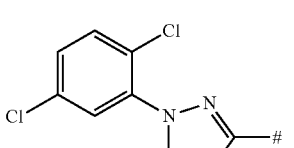 |
| R3-39 | 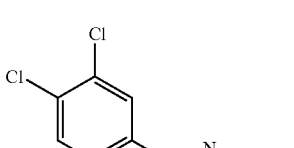 |
| R3-40 | 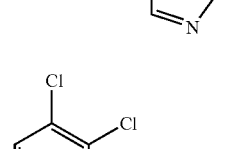 |
| R3-41 | 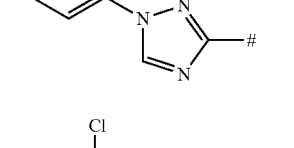 |

TABLE A-continued
| Line | R³ |
|---|---|
| R3-42 | 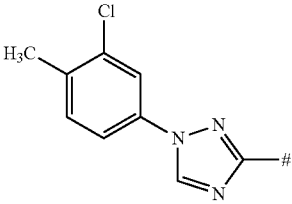 |
| R3-43 | 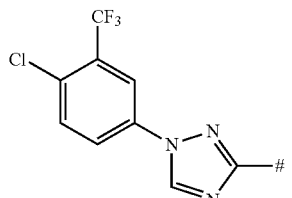 |
| R3-44 | 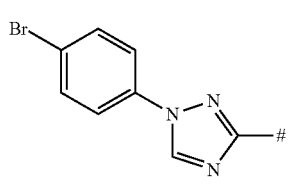 |
| R3-45 | 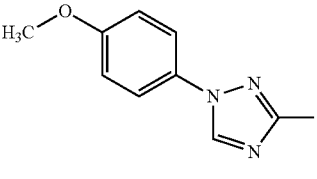 |
| R3-46 | 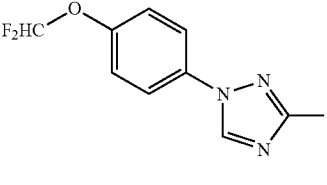 |
| R3-47 | 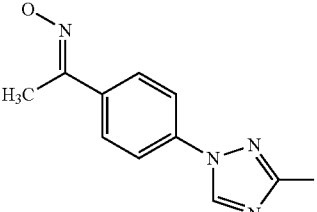 |
| R3-48 | 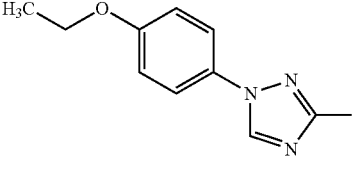 |
| R3-49 | 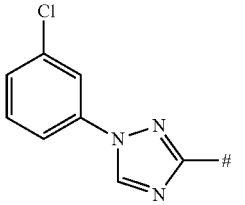 |
| R3-50 | 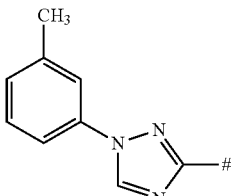 |
| R3-51 | 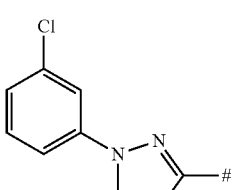 |
| R3-52 | 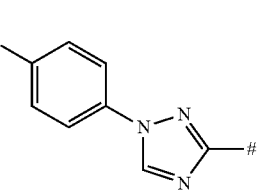 |
| R3-53 | 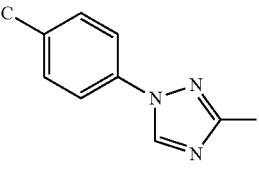 |
| R3-54 | 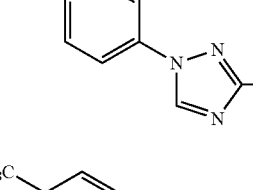 |
| R3-55 | 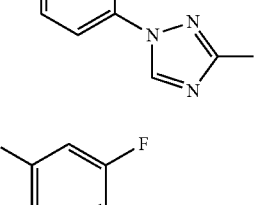 |
| R3-56 | 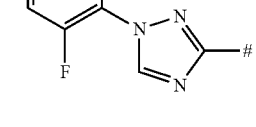 |

TABLE A-continued
| Line | R³ |
|---|---|
| R3-57 | 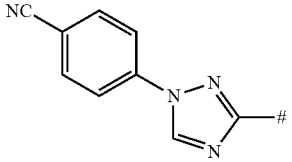 |
| R3-58 | 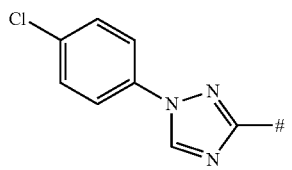 |
| R3-59 | 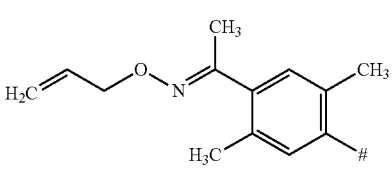 |
| R3-60 | 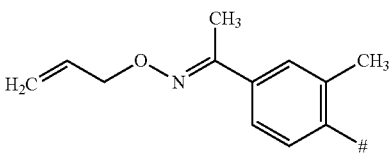 |
| R3-61 | 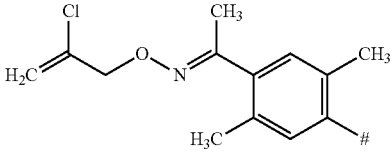 |
| R3-62 | 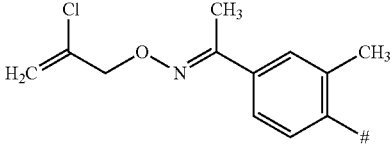 |
| R3-63 | 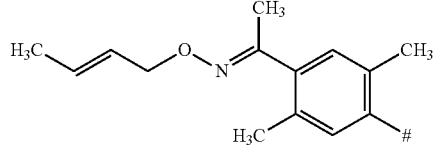 |
| R3-64 | 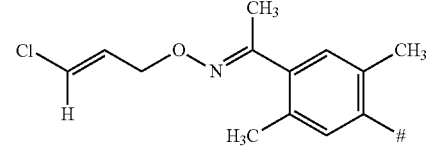 |
| R3-65 | 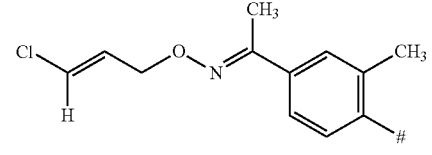 |
| R3-66 | 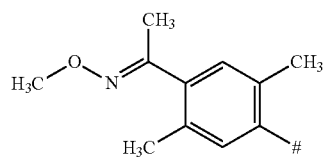 |
| R3-67 | 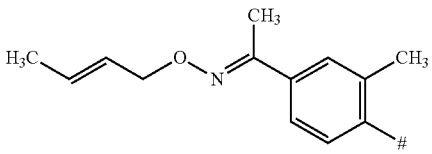 |
| R3-68 | 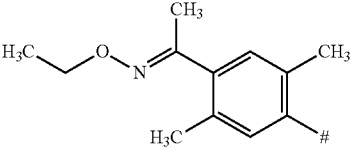 |
| R3-69 | 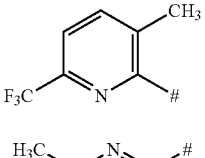 |
| R3-70 |  |
| R3-71 | 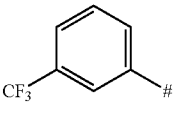 |
| R3-72 | 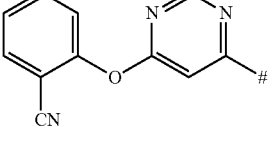 |
| R3-73 | 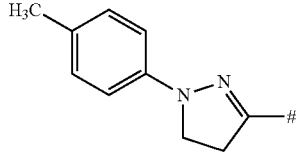 |
| R3-74 | 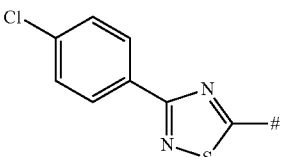 |
| R3-75 | 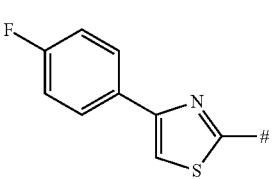 |

TABLE A-continued
| Line | R³ |
|---|---|
| R3-76 |  |
| R3-77 | 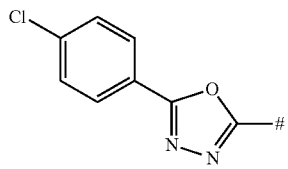 |
| R3-78 | 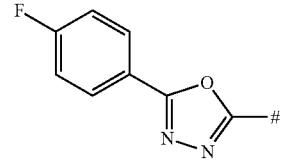 |
| R3-79 | 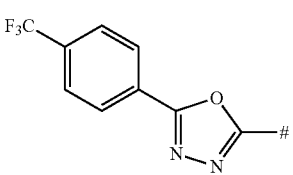 |
| R3-80 | 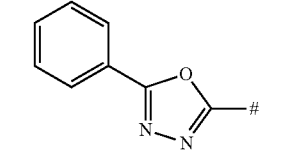 |
| R3-81 | 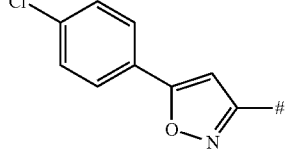 |
| R3-82 | 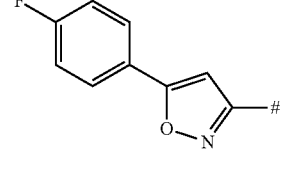 |
| R3-83 | 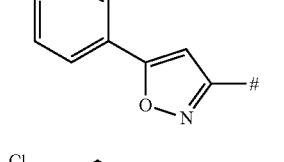 |
| R3-84 | 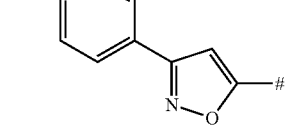 |
| R3-85 | 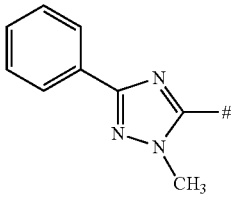 |
| R3-86 | 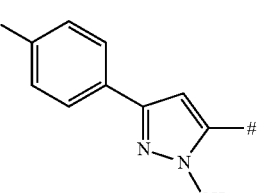 |
| R3-87 | 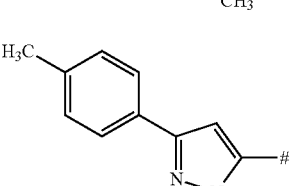 |
| R3-88 | 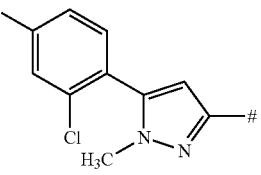 |
| R3-89 | 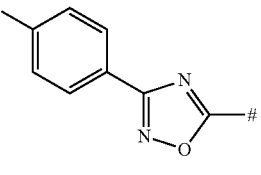 |
| R3-90 | 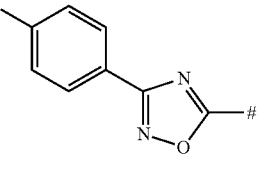 |
| R3-91 | 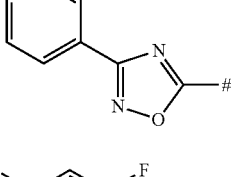 |
| R3-92 | 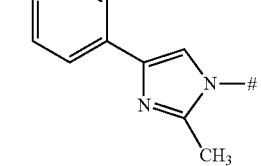 |

TABLE A-continued
| Line | R³ |
|------|-----|
| R3-93 | 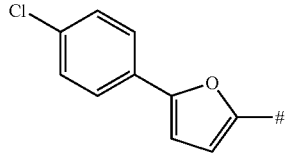 |
| R3-94 | 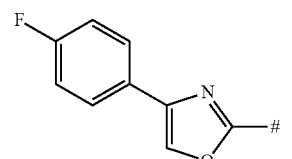 |
| R3-95 | 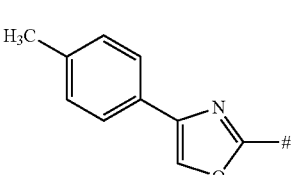 |
| R3-96 | 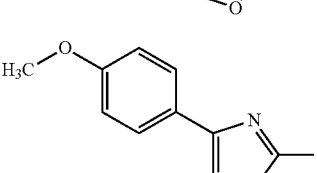 |
| R3-97 | 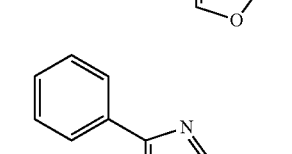 |
| R3-98 | 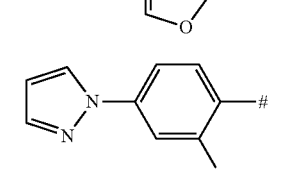 |
| R3-99 | 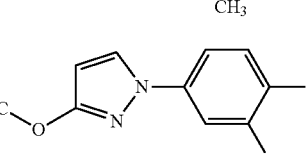 |
| R3-100 | 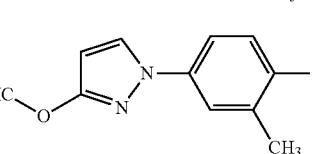 |
| R3-101 | 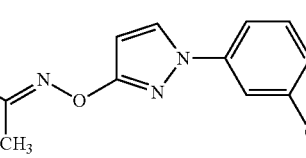 |
| R3-102 | 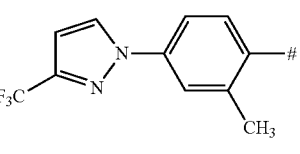 |
| R3-103 | 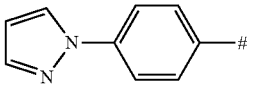 |
| R3-104 | 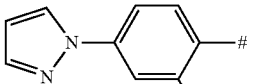 |
| R3-105 | 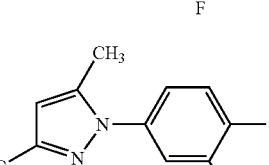 |
| R3-106 | 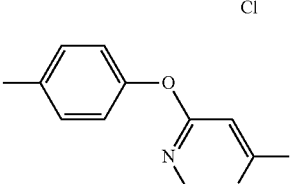 |
| R3-107 | 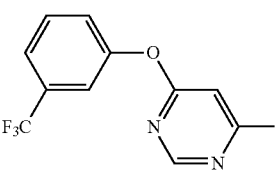 |
| R3-108 | 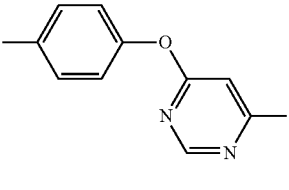 |
| R3-109 | 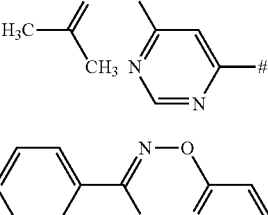 |
| R3-110 | 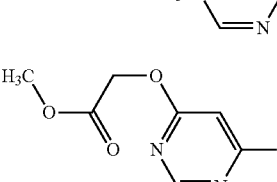 |
| R3-111 | 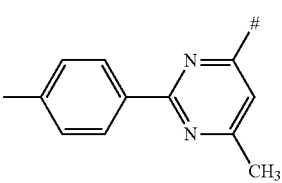 |
| R3-112 |  |

TABLE A-continued

| Line | R³ |
|---|---|
| R3-113 | 4-(difluoromethoxy)phenyl-6-methylpyrimidin-2-yl |
| R3-114 | 6-(4-chlorophenyl)pyrimidin-4-yl |
| R3-115 | 3-chloro-5-(trifluoromethyl)pyridin-2-yl |
| R3-116 | 3-methyl-5-(trifluoromethyl)pyridin-2-yl |
| R3-117 | pyridin-2-yl |
| R3-118 | (E)-1-(4-fluorophenyl)-N-methoxymethanimine |
| R3-119 | (E)-1-(4-chlorophenyl)-N-methoxymethanimine |
| R3-120 | (E)-N-ethoxy-ethanimine |
| R3-121 | (E)-N-((4-fluorobenzyl)oxy)ethanimine |
| R3-122 | (E)-N-((4-fluorophenoxy))ethanimine |
| R3-123 | (E)-N-((5-(trifluoromethyl)pyridin-2-yl)oxy)ethanimine |
| R3-124 | (E)-N-((3-chloro-5-(trifluoromethyl)pyridin-2-yl)oxy)ethanimine |
| R3-125 | (E)-N-methoxy-3-methylbut-2-en-imine |
| R3-126 | 2,5,7-trimethyl-3-methylpyrazolo[1,5-a]pyrimidine |
| R3-127 | (E)-1-(3,4-dimethylphenyl)-N-methoxyethanimine |
| R3-128 | (E)-1-(3,4-dimethylphenyl)-N-ethoxyethanimine |

TABLE A-continued

| Line | R³ |
|---|---|
| R3-129 | 4-isopropoxyphenyl-pyrazol-3-yl (#) |
| R3-130 | 3-(1-phenyl-1H-pyrazol-4-yl)phenyl (#) |
| R3-131 | 4-(1-phenyl-1H-pyrazol-4-yl)phenyl (#) |
| R3-132 | 1-(4-#-phenyl)ethan-1-one O-allyl oxime |
| R3-133 | 2'-methyl-5-methyl-[2,4'-bithiazol]-4-yl (#) |
| R3-134 | 1-(3-methyl-4-#-phenyl)ethan-1-one O-propargyl oxime |
| R3-135 | 1-(3-methyl-4-#-phenyl)ethan-1-one |
| R3-136 | 1-(2,5-dimethyl-4-#-phenyl)ethan-1-one O-propargyl oxime |
| R3-137 | 1-(3-methyl-4-#-phenyl)ethan-1-one O-(3-chloroallyl) oxime |
| R3-138 | 1-(2,5-dimethyl-4-#-phenyl)ethan-1-one O-(3-chloroallyl) oxime |
| R3-139 | 2,3,5-trifluorophenyl (#) |
| R3-140 | 4-chlorophenyl (#) |
| R3-141 | 3-(difluoromethyl)-1-methyl-1H-pyrazol-5-yl (#) |
| R3-142 | 4-(trifluoromethyl)phenyl (#) |
| R3-143 | 1-(2,5-dimethyl-4-#-phenyl)butan-1-one O-methyl oxime |
| R3-144 | 1-(3-methyl-4-#-phenyl)butan-1-one O-methyl oxime |
| R3-145 | cyclopropyl(3-methyl-4-#-phenyl)methanone O-ethyl oxime |

TABLE A-continued
| Line | R³ |
|---|---|
| R3-146 | 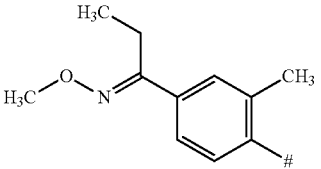 |
| R3-147 | 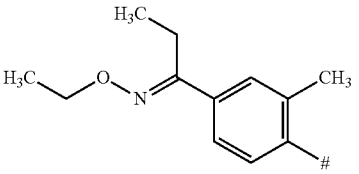 |
| R3-148 | 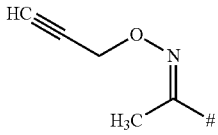 |
| R3-149 | 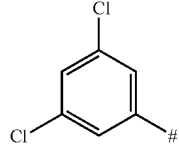 |
| R3-150 | 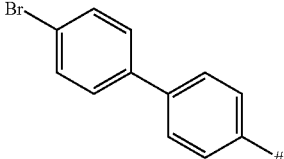 |
| R3-151 | 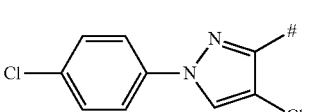 |
| R3-152 | 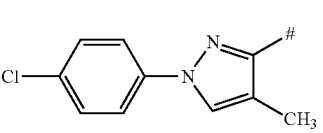 |
| R3-153 | 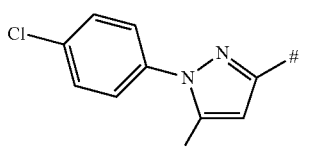 |
| R3-154 | 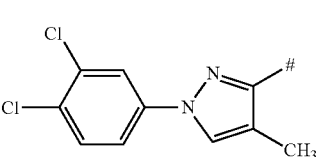 |
| R3-155 | 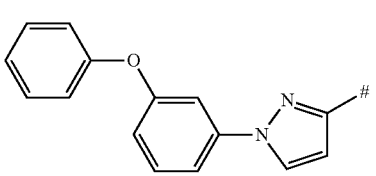 |
| R3-156 | 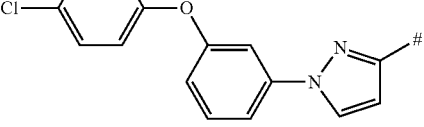 |
| R3-157 | 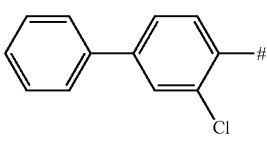 |
| R3-158 | 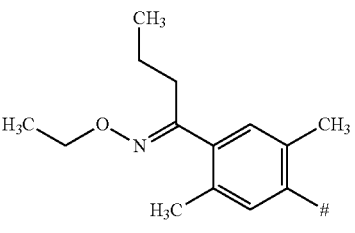 |
| R3-159 | 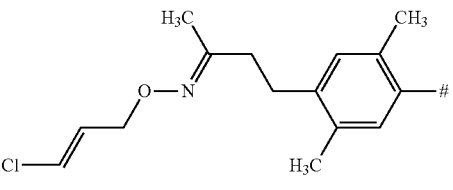 |
| R3-160 | 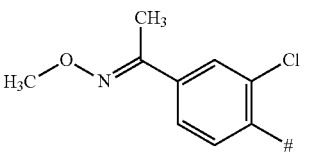 |
| R3-161 | 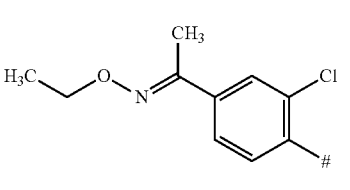 |
| R3-162 | 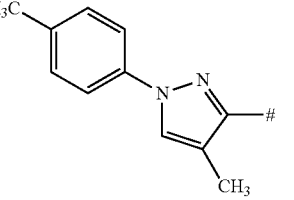 |
| R3-163 | 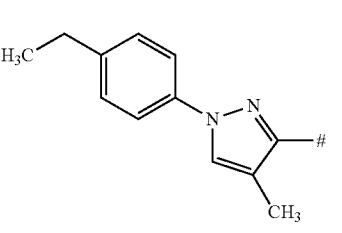 |

TABLE A-continued
| Line | R³ |
|---|---|
| R3-164 | 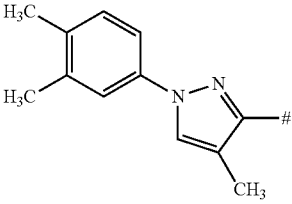 |
| R3-165 | 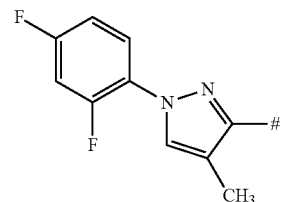 |
| R3-166 | 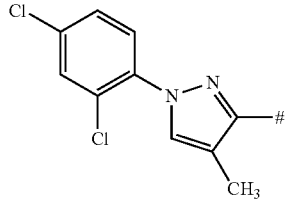 |
| R3-167 | 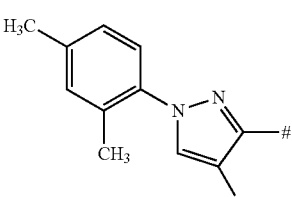 |
| R3-168 | 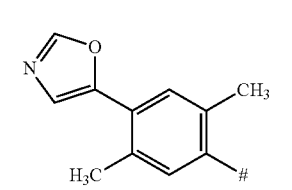 |
| R3-169 | 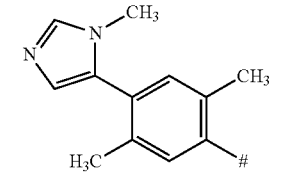 |
| R3-170 | 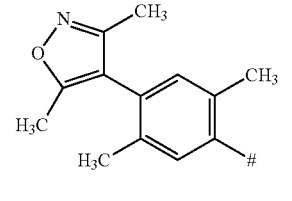 |
| R3-171 | 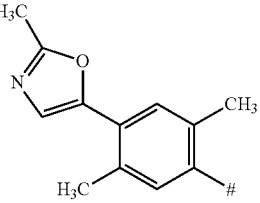 |
| R3-172 | 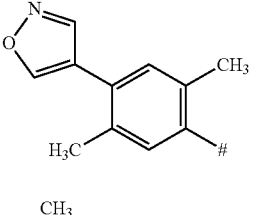 |
| R3-173 | 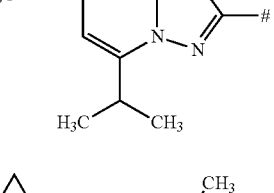 |
| R3-174 | 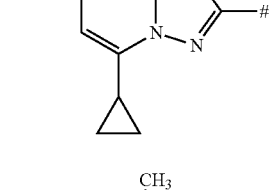 |
| R3-175 | 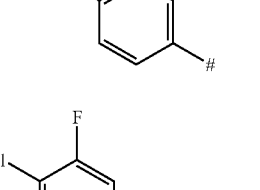 |
| R3-176 | 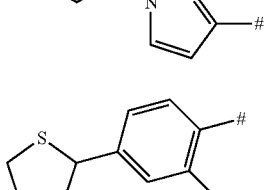 |
| R3-177 | 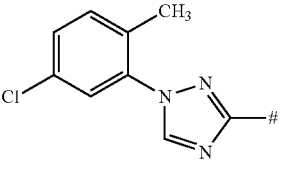 |
| R3-178 | 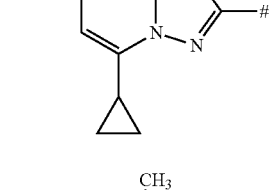 |

TABLE A-continued

| Line | R³ |
|---|---|
| R3-179 | 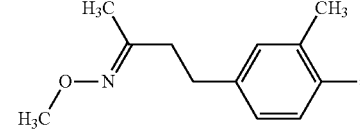 |
| R3-180 | 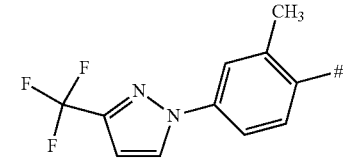 |
| R3-181 | 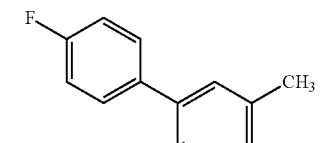 |
| R3-182 | 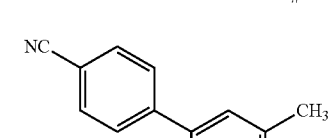 |
| R3-183 | 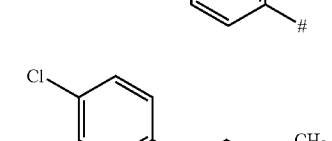 |
| R3-184 | 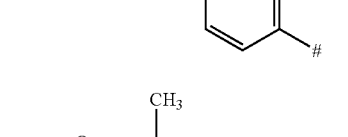 |
| R3-185 | 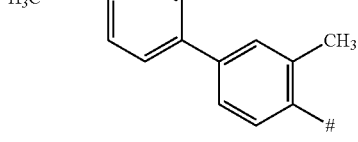 |
| R3-186 | 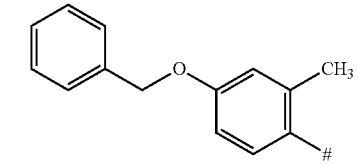 |
| R3-187 | 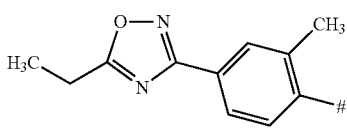 |
| R3-188 | 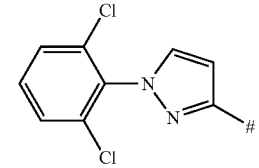 |
| R3-189 | 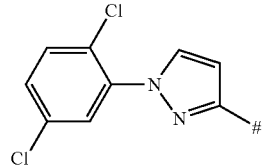 |
| R3-190 | 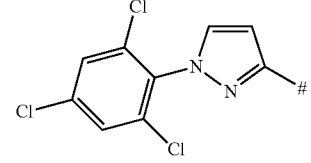 |
| R3-191 | 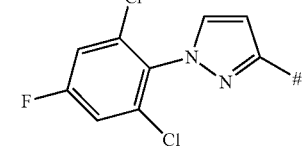 |
| R3-192 | 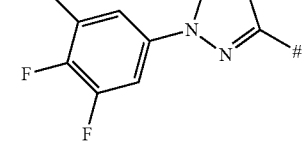 |
| R3-193 | 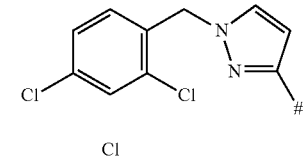 |
| R3-194 | 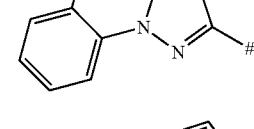 |
| R3-195 | 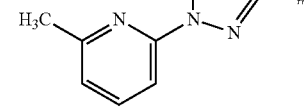 | wherein # indicates the point of attachment to the linker moiety Y.

Preferred embodiments of the invention relate to compounds I, wherein the group R³ is R3-A, in particular R3-1 (1-(4-chlorophenyl)-pyrazol-3-yl).

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. cf. http://ceragmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted posttranslational modification of protein(s), oligo- or polypeptides e.g. by glycosylation or polymer additions such as prenylated, acetylated or farnesylated moieties or PEG moieties.

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*. Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F.*

*culmorum* (root rot, scab or head blight) on cereals (e.g. wheat or barley), *F. oxysporum* on tomatoes, *F. solani* on soybeans and *F. verticilloides* on corn; *Gaeumannomyces graminis* (take-all) on cereals (e.g. wheat or barley) and corn; *Gibberella* spp. on cereals (e.g. *G. zeae*) and rice (e.g. *G. fujikuroi* Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoi*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humilion* hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei*(dwarf rust), *P. graminis* (stem or black rust) or *P. recondita* (brown or leaf rust) on cereals, such as e.g. wheat, barley or rye, *P. kuehnii* (orange rust) on sugar cane and *P. asparagion* asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. griseaon* turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. scerotiorum*) and soybeans (e.g. *S. rolfsii* or *S. scerotiorum*); *Septoria* spp. on various plants, e.g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator*(powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrum endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate,ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for Composition Types and their Preparation are:

i) Water-Soluble Concentrates (SL, LS)

10-60 wt % of a compound I and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a compound I are ground finely and mixed intimately with solid carrier (e.g. finely divided kaolin) ad 100 wt %.

x) Granules (GR, FG)

0.5-30 wt % of a compound I is ground finely and associated with solid carrier (e.g. silicate) ad 100 wt %. Granulation is achieved by extrusion, spray-drying or fluidized bed.

xi) Ultra-Low Volume Liquids (UL)

1-50 wt % of a compound I are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I can be used, is intended to illustrate the possible combinations but does not limit them:

A) Respiration inhibitors
  Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)phenyl)-2-methoxyimino-N-methyl-acetamide, pyribencarb, triclopyricarb/chlorodincarb, famoxadone, fenamidone;
  inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate inhibitors of complex II (e.g. carboxamides): benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4′-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C) Nucleic acid synthesis inhibitors
  phenylamides or acyl amino acid fungicides: benalaxyl, benalaxyl-M, kiralaxyl, metalaxyl, metalaxyl-M (mefenoxam), ofurace, oxadixyl;
  others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of cell division and cytoskeleton
  tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of amino acid and protein synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal transduction inhibitors
MAP/histidine kinase inhibitors: fluoroimid, iprodione, procymidone, vinclozolin, fenpiclonil, fludioxonil;
G protein inhibitors: quinoxyfen;

G) Lipid and membrane synthesis inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl)carbamic acid-(4-fluorophenyl)ester;
compounds affecting cell membrane permeability and fatty acids: propamocarb, propamocarb-hydrochlorid
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)tetraone;

I) Cell wall synthesis inhibitors
inhibitors of glucan synthesis: validamycin, polyoxin B;
melanin synthesis inhibitors: pyroquilon, tricyclazole, carpropamid, dicyclomet, fenoxanil;

J) Plant defence inducers
acibenzolar-S-methyl, probenazole, isotianil, tiadinil, prohexadione-calcium; phosphonates: fosetyl, fosetyl-aluminum, phosphorous acid and its salts;

K) Unknown mode of action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxincopper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamide, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanylpropoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole),
N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ri-cerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; benzovindiflupyr, bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-369 of Table B.

A further embodiment relates to the compositions B-1 to B-369 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
| --- | --- | --- |
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Benzovindiflupyr |
| B-25 | one individualized compound I | Bixafen |
| B-26 | one individualized compound I | Boscalid |
| B-27 | one individualized compound I | Carboxin |
| B-28 | one individualized compound I | Fenfuram |
| B-29 | one individualized compound I | Fenhexamid |
| B-30 | one individualized compound I | Flutolanil |
| B-31 | one individualized compound I | Fluxapyroxad |
| B-32 | one individualized compound I | Furametpyr |
| B-33 | one individualized compound I | Isopyrazam |
| B-34 | one individualized compound I | Isotianil |
| B-35 | one individualized compound I | Kiralaxyl |
| B-36 | one individualized compound I | Mepronil |
| B-37 | one individualized compound I | Metalaxyl |
| B-38 | one individualized compound I | Metalaxyl-M |
| B-39 | one individualized compound I | Ofurace |
| B-40 | one individualized compound I | Oxadixyl |
| B-41 | one individualized compound I | Oxycarboxin |
| B-42 | one individualized compound I | Penflufen |
| B-43 | one individualized compound I | Penthiopyrad |
| B-44 | one individualized compound I | Sedaxane |
| B-45 | one individualized compound I | Tecloftalam |
| B-46 | one individualized compound I | Thifluzamide |
| B-47 | one individualized compound I | Tiadinil |
| B-48 | one individualized compound I | 2-Amino-4-methyl-thiazole-5-carboxylic acid anilide |
| B-49 | one individualized compound I | N-(4'-trifluoromethylthiobiphenyl-2-yl)-3-difluoromethyl-1-methyl-1H-pyrazole-4-carboxamide |

TABLE B-continued

Composition comprising one indiviualized compound I
and one further active substance from groups A) to O)

| Mixture | Component 1 | Component 2 |
|---|---|---|
| B-50 | one individualized compound I | N-(2-(1,3,3-trimethyl-butyl)-phenyl)-1,3-dimethyl-5-fluoro-1H-pyrazole-4-carboxamide |
| B-51 | one individualized compound I | 3-(difluoromethyl)-1-methyl-N-(1,1,3-tri-methylindan-4-yl)pyrazole-4-carbox-amide |
| B-52 | one individualized compound I | 3-(trifluoromethyl)-1-methyl-N-(1,1,3-tri-methylindan-4-yl)pyrazole-4-carbox-amide |
| B-53 | one individualized compound I | 1,3-dimethyl-N-(1,1,3-trimethylindan-4-yl)pyrazole-4-carboxamide |
| B-54 | one individualized compound I | 3-(trifluoromethyl)-1,5-dimethyl-N-(1,1,3-trimethylindan-4-yl)pyrazole-4-carboxamide |
| B-55 | one individualized compound I | 3-(difluoromethyl)-1,5-dimethyl-N-(1,1,3-trimethylindan-4-yl)pyrazole-4-carboxamide |
| B-56 | one individualized compound I | 1,3,5-trimethyl-N-(1,1,3-trimethylindan-4-yl)pyrazole-4-carboxamide |
| B-57 | one individualized compound I | Dimethomorph |
| B-58 | one individualized compound I | Flumorph |
| B-59 | one individualized compound I | Pyrimorph |
| B-60 | one individualized compound I | Flumetover |
| B-61 | one individualized compound I | Fluopicolide |
| B-62 | one individualized compound I | Fluopyram |
| B-63 | one individualized compound I | Zoxamide |
| B-64 | one individualized compound I | Carpropamid |
| B-65 | one individualized compound I | Diclocymet |
| B-66 | one individualized compound I | Mandipropamid |
| B-67 | one individualized compound I | Oxytetracyclin |
| B-68 | one individualized compound I | Silthiofam |
| B-69 | one individualized compound I | N-(6-methoxy-pyridin-3-yl) cyclopro-panecarboxylic acid amide |
| B-70 | one individualized compound I | Azaconazole |
| B-71 | one individualized compound I | Bitertanol |
| B-72 | one individualized compound I | Bromuconazole |
| B-73 | one individualized compound I | Cyproconazole |
| B-74 | one individualized compound I | Difenoconazole |
| B-75 | one individualized compound I | Diniconazole |
| B-76 | one individualized compound I | Diniconazole-M |
| B-77 | one individualized compound I | Epoxiconazole |
| B-78 | one individualized compound I | Fenbuconazole |
| B-79 | one individualized compound I | Fluquinconazole |
| B-80 | one individualized compound I | Flusilazole |
| B-81 | one individualized compound I | Flutriafol |
| B-82 | one individualized compound I | Hexaconazol |
| B-83 | one individualized compound I | Imibenconazole |
| B-84 | one individualized compound I | Ipconazole |
| B-85 | one individualized compound I | Metconazole |
| B-86 | one individualized compound I | Myclobutanil |
| B-87 | one individualized compound I | Oxpoconazol |
| B-88 | one individualized compound I | Paclobutrazol |
| B-89 | one individualized compound I | Penconazole |
| B-90 | one individualized compound I | Propiconazole |
| B-91 | one individualized compound I | Prothioconazole |
| B-92 | one individualized compound I | Simeconazole |
| B-93 | one individualized compound I | Tebuconazole |
| B-94 | one individualized compound I | Tetraconazole |
| B-95 | one individualized compound I | Triadimefon |
| B-96 | one individualized compound I | Triadimenol |
| B-97 | one individualized compound I | Triticonazole |
| B-98 | one individualized compound I | Uniconazole |
| B-99 | one individualized compound I | 1-[rel-(2S;3R)-3-(2-chlorophenyl)-2-(2,4-difluorophenyl)-oxiranylmethyl]-5-thiocyanato-1H-[1,2,4]triazole, |
| B-100 | one individualized compound I | 2-[rel-(2S;3R)-3-(2-chlorophenyl)-2-(2,4-difluorophenyl)-oxiranylmethyl]-2H-[1,2,4]triazole-3-thiol |
| B-101 | one individualized compound I | Cyazofamid |
| B-102 | one individualized compound I | Amisulbrom |
| B-103 | one individualized compound I | Imazalil |
| B-104 | one individualized compound I | Imazalil-sulfate |
| B-105 | one individualized compound I | Pefurazoate |
| B-106 | one individualized compound I | Prochloraz |
| B-107 | one individualized compound I | Triflumizole |

TABLE B-continued

Composition comprising one indiviualized compound I
and one further active substance from groups A) to O)

| Mixture | Component 1 | Component 2 |
|---|---|---|
| B-108 | one individualized compound I | Benomyl |
| B-109 | one individualized compound I | Carbendazim |
| B-110 | one individualized compound I | Fuberidazole |
| B-111 | one individualized compound I | Thiabendazole |
| B-112 | one individualized compound I | Ethaboxam |
| B-113 | one individualized compound I | Etridiazole |
| B-114 | one individualized compound I | Hymexazole |
| B-115 | one individualized compound I | 2-(4-Chloro-phenyl)-N-[4-(3,4-di-methoxy-phenyl)-isoxazol-5-yl]-2-prop-2-yn-yloxy-acetamide |
| B-116 | one individualized compound I | Fluazinam |
| B-117 | one individualized compound I | Pyrifenox |
| B-118 | one individualized compound I | 3-[5-(4-Chloro-phenyl)-2,3-dimethyl-isoxazolidin-3-yl]-pyridine (Pyrisoxazole) |
| B-119 | one individualized compound I | 3-[5-(4-Methyl-phenyl)-2,3-dimethyl-isoxazolidin-3-yl]-pyridine |
| B-120 | one individualized compound I | Bupirimate |
| B-121 | one individualized compound I | Cyprodinil |
| B-122 | one individualized compound I | 5-Fluorocytosine |
| B-123 | one individualized compound I | 5-Fluoro-2-(p-tolylmethoxy)pyrimidin-4-amine |
| B-124 | one individualized compound I | 5-Fluoro-2-(4-fluorophenylmethoxy)-pyrimidin-4-amine |
| B-125 | one individualized compound I | Diflumetorim |
| B-126 | one individualized compound I | (5,8-Difluoroquinazolin-4-yl)-{2-[2-fluoro-4-(4-trifluoromethylpyridin-2-yloxy)-phenyl]-ethyl}-amine |
| B-127 | one individualized compound I | Fenarimol |
| B-128 | one individualized compound I | Ferimzone |
| B-129 | one individualized compound I | Mepanipyrim |
| B-130 | one individualized compound I | Nitrapyrin |
| B-131 | one individualized compound I | Nuarimol |
| B-132 | one individualized compound I | Pyrimethanil |
| B-133 | one individualized compound I | Triforine |
| B-134 | one individualized compound I | Fenpiclonil |
| B-135 | one individualized compound I | Fludioxonil |
| B-136 | one individualized compound I | Aldimorph |
| B-137 | one individualized compound I | Dodemorph |
| B-138 | one individualized compound I | Dodemorph-acetate |
| B-139 | one individualized compound I | Fenpropimorph |
| B-140 | one individualized compound I | Tridemorph |
| B-141 | one individualized compound I | Fenpropidin |
| B-142 | one individualized compound I | Fluoroimid |
| B-143 | one individualized compound I | Iprodione |
| B-144 | one individualized compound I | Procymidone |
| B-145 | one individualized compound I | Vinclozolin |
| B-146 | one individualized compound I | Famoxadone |
| B-147 | one individualized compound I | Fenamidone |
| B-148 | one individualized compound I | Flutianil |
| B-149 | one individualized compound I | Octhilinone |
| B-150 | one individualized compound I | Probenazole |
| B-151 | one individualized compound I | Fenpyrazamine |
| B-152 | one individualized compound I | Acibenzolar-S-methyl |
| B-153 | one individualized compound I | Ametoctradin |
| B-154 | one individualized compound I | Amisulbrom |
| B-155 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-156 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-157 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-158 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |

TABLE B-continued

Composition comprising one indiviualized compound I
and one further active substance from groups A) to O)

| Mixture | Component 1 | Component 2 |
|---|---|---|
| B-159 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| B-160 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-161 | one individualized compound I | Anilazin |
| B-162 | one individualized compound I | Blasticidin-S |
| B-163 | one individualized compound I | Captafol |
| B-164 | one individualized compound I | Captan |
| B-165 | one individualized compound I | Chinomethionat |
| B-166 | one individualized compound I | Dazomet |
| B-167 | one individualized compound I | Debacarb |
| B-168 | one individualized compound I | Diclomezine |
| B-169 | one individualized compound I | Difenzoquat, |
| B-170 | one individualized compound I | Difenzoquat-methylsulfate |
| B-171 | one individualized compound I | Fenoxanil |
| B-172 | one individualized compound I | Folpet |
| B-173 | one individualized compound I | Oxolinsäure |
| B-174 | one individualized compound I | Piperalin |
| B-175 | one individualized compound I | Proquinazid |
| B-176 | one individualized compound I | Pyroquilon |
| B-177 | one individualized compound I | Quinoxyfen |
| B-178 | one individualized compound I | Triazoxid |
| B-179 | one individualized compound I | Tricyclazole |
| B-180 | one individualized compound I | 2-Butoxy-6-iodo-3-propyl-chromen-4-one |
| B-181 | one individualized compound I | 5-Chloro-1-(4,6-dimethoxy-pyrimidin-2-yl)-2-methyl-1H-benzoimidazole |
| B-182 | one individualized compound I | 5-Chloro-7-(4-methyl-piperidin-1-yl)-6-(2,4,6-trifluoro-phenyl)-[1,2,4]triazolo[1,5-a]pyrimidine |
| B-183 | one individualized compound I | Ferbam |
| B-184 | one individualized compound I | Mancozeb |
| B-185 | one individualized compound I | Maneb |
| B-186 | one individualized compound I | Metam |
| B-187 | one individualized compound I | Methasulphocarb |
| B-188 | one individualized compound I | Metiram |
| B-189 | one individualized compound I | Propineb |
| B-190 | one individualized compound I | Thiram |
| B-191 | one individualized compound I | Zineb |
| B-192 | one individualized compound I | Ziram |
| B-193 | one individualized compound I | Diethofencarb |
| B-194 | one individualized compound I | Benthiavalicarb |
| B-195 | one individualized compound I | Iprovalicarb |
| B-196 | one individualized compound I | Propamocarb |
| B-197 | one individualized compound I | Propamocarb hydrochlorid |
| B-198 | one individualized compound I | Valifenalate |
| B-199 | one individualized compound I | N-(1-(1-(4-cyanophenyl)ethanesulfonyl)-but-2-yl) carbamic acid-(4-fluoro-phenyl) ester |
| B-200 | one individualized compound I | Dodine |
| B-201 | one individualized compound I | Dodine free base |
| B-202 | one individualized compound I | Guazatine |
| B-203 | one individualized compound I | Guazatine-acetate |
| B-204 | one individualized compound I | Iminoctadine |
| B-205 | one individualized compound I | Iminoctadine-triacetate |
| B-206 | one individualized compound I | Iminoctadine-tris(albesilate) |
| B-207 | one individualized compound I | Kasugamycin |
| B-208 | one individualized compound I | Kasugamycin-hydrochloride-hydrate |
| B-209 | one individualized compound I | Polyoxine |
| B-210 | one individualized compound I | Streptomycin |
| B-211 | one individualized compound I | Validamycin A |
| B-212 | one individualized compound I | Binapacryl |
| B-213 | one individualized compound I | Dicloran |
| B-214 | one individualized compound I | Dinobuton |
| B-215 | one individualized compound I | Dinocap |
| B-216 | one individualized compound I | Nitrothal-isopropyl |
| B-217 | one individualized compound I | Tecnazen |
| B-218 | one individualized compound I | Fentin salts |
| B-219 | one individualized compound I | Dithianon |

TABLE B-continued

Composition comprising one indiviualized compound I
and one further active substance from groups A) to O)

| Mixture | Component 1 | Component 2 |
| --- | --- | --- |
| B-220 | one individualized compound I | 2,6-dimethyl-1H,5H-[1,4]dithiino[2,3-c:5,6-c']dipyrrole-1,3,5,7(2H,6H)-tetraone |
| B-221 | one individualized compound I | Isoprothiolane |
| B-222 | one individualized compound I | Edifenphos |
| B-223 | one individualized compound I | Fosetyl, Fosetyl-aluminium |
| B-224 | one individualized compound I | Iprobenfos |
| B-225 | one individualized compound I | Phosphorous acid ($H_3PO_3$) and derivatives |
| B-226 | one individualized compound I | Pyrazophos |
| B-227 | one individualized compound I | Tolclofos-methyl |
| B-228 | one individualized compound I | Chlorothalonil |
| B-229 | one individualized compound I | Dichlofluanid |
| B-230 | one individualized compound I | Dichlorophen |
| B-231 | one individualized compound I | Flusulfamide |
| B-232 | one individualized compound I | Hexachlorbenzene |
| B-233 | one individualized compound I | Pencycuron |
| B-234 | one individualized compound I | Pentachlorophenol and salts |
| B-235 | one individualized compound I | Phthalide |
| B-236 | one individualized compound I | Quintozene |
| B-237 | one individualized compound I | Thiophanate Methyl |
| B-238 | one individualized compound I | Tolylfluanid |
| B-239 | one individualized compound I | N-(4-chloro-2-nitro-phenyl)-N-ethyl-4-methyl-benzenesulfonamide |
| B-240 | one individualized compound I | Bordeaux mixture |
| B-241 | one individualized compound I | Copper acetate |
| B-242 | one individualized compound I | Copper hydroxide |
| B-243 | one individualized compound I | Copper oxychloride |
| B-244 | one individualized compound I | basic Copper sulfate |
| B-245 | one individualized compound I | Sulfur |
| B-246 | one individualized compound I | Biphenyl |
| B-247 | one individualized compound I | Bronopol |
| B-248 | one individualized compound I | Cyflufenamid |
| B-249 | one individualized compound I | Cymoxanil |
| B-250 | one individualized compound I | Diphenylamin |
| B-251 | one individualized compound I | Metrafenone |
| B-252 | one individualized compound I | Pyriofenone |
| B-253 | one individualized compound I | Mildiomycin |
| B-254 | one individualized compound I | Oxin-copper |
| B-255 | one individualized compound I | Oxathiapiprolin |
| B-256 | one individualized compound I | Prohexadione calcium |
| B-257 | one individualized compound I | Spiroxamine |
| B-258 | one individualized compound I | Tebufloquin |
| B-259 | one individualized compound I | Tolylfluanid |
| B-260 | one individualized compound I | N-(Cyclopropylmethoxyimino-(6-difluoromethoxy-2,3-difluoro-phenyl)-methyl)-2-phenyl acetamide |
| B-261 | one individualized compound I | N'-(4-(4-chloro-3-trifluoromethyl-phenoxy)-2,5-dimethyl-phenyl)-N-ethyl-N-methyl formamidine |
| B-262 | one individualized compound I | N'-(4-(4-fluoro-3-trifluoromethyl-phenoxy)-2,5-dimethyl-phenyl)-N-ethyl-N-methyl formamidine |
| B-263 | one individualized compound I | N'-(2-methyl-5-trifluoromethyl-4-(3-trimethylsilanyl-propoxy)-phenyl)-N-ethyl-N-methyl formamidine |
| B-264 | one individualized compound I | N'-(5-difluoromethyl-2-methyl-4-(3-trimethylsilanyl-propoxy)-phenyl)-N-ethyl-N-methyl formamidine |
| B-265 | one individualized compound I | Methoxy-acetic acid 6-tert-butyl-8-fluoro-2,3-dimethyl-quinolin-4-yl ester |
| B-266 | one individualized compound I | *Bacillus subtilis* NRRL No. B-21661 |
| B-267 | one individualized compound I | *Bacillus pumilus* NRRL No. B-30087 |
| B-268 | one individualized compound I | *Ulocladium oudemansii* |
| B-269 | one individualized compound I | Carbaryl |
| B-270 | one individualized compound I | Carbofuran |
| B-271 | one individualized compound I | Carbosulfan |
| B-272 | one individualized compound I | Methomylthiodicarb |
| B-273 | one individualized compound I | Bifenthrin |
| B-274 | one individualized compound I | Cyfluthrin |
| B-275 | one individualized compound I | Cypermethrin |
| B-276 | one individualized compound I | alpha-Cypermethrin |
| B-277 | one individualized compound I | zeta-Cypermethrin |
| B-278 | one individualized compound I | Deltamethrin |
| B-279 | one individualized compound I | Esfenvalerate |

TABLE B-continued

Composition comprising one indiviualized compound I
and one further active substance from groups A) to O)

| Mixture | Component 1 | Component 2 |
|---|---|---|
| B-280 | one individualized compound I | Lambda-cyhalothrin |
| B-281 | one individualized compound I | Permethrin |
| B-282 | one individualized compound I | Tefluthrin |
| B-283 | one individualized compound I | Diflubenzuron |
| B-284 | one individualized compound I | Flufenoxuron |
| B-285 | one individualized compound I | Lufenuron |
| B-286 | one individualized compound I | Teflubenzuron |
| B-287 | one individualized compound I | Spirotetramate |
| B-288 | one individualized compound I | Clothianidin |
| B-289 | one individualized compound I | Dinotefuran |
| B-290 | one individualized compound I | Imidacloprid |
| B-291 | one individualized compound I | Thiamethoxam |
| B-292 | one individualized compound I | Flupyradifurone |
| B-293 | one individualized compound I | Acetamiprid |
| B-294 | one individualized compound I | Thiacloprid |
| B-295 | one individualized compound I | Endosulfan |
| B-296 | one individualized compound I | Fipronil |
| B-297 | one individualized compound I | Abamectin |
| B-298 | one individualized compound I | Emamectin |
| B-299 | one individualized compound I | Spinosad |
| B-300 | one individualized compound I | Spinetoram |
| B-301 | one individualized compound I | Hydramethylnon |
| B-302 | one individualized compound I | Chlorfenapyr |
| B-303 | one individualized compound I | Fenbutatin oxide |
| B-304 | one individualized compound I | Indoxacarb |
| B-305 | one individualized compound I | Metaflumizone |
| B-306 | one individualized compound I | Flonicamid |
| B-307 | one individualized compound I | Lubendiamide |
| B-308 | one individualized compound I | Chlorantraniliprole |
| B-309 | one individualized compound I | Cyazypyr (HGW86) |
| B-310 | one individualized compound I | Cyflumetofen |
| B-311 | one individualized compound I | Acetochlor |
| B-312 | one individualized compound I | Dimethenamid |
| B-313 | one individualized compound I | metolachlor |
| B-314 | one individualized compound I | Metazachlor |
| B-315 | one individualized compound I | Glyphosate |
| B-316 | one individualized compound I | Glufosinate |
| B-317 | one individualized compound I | Sulfosate |
| B-318 | one individualized compound I | Clodinafop |
| B-319 | one individualized compound I | Fenoxaprop |
| B-320 | one individualized compound I | Fluazifop |
| B-321 | one individualized compound I | Haloxyfop |
| B-322 | one individualized compound I | Paraquat |
| B-323 | one individualized compound I | Phenmedipham |
| B-324 | one individualized compound I | Clethodim |
| B-325 | one individualized compound I | Cycloxydim |
| B-326 | one individualized compound I | Profoxydim |
| B-327 | one individualized compound I | Sethoxydim |
| B-328 | one individualized compound I | Tepraloxydim |
| B-329 | one individualized compound I | Pendimethalin |
| B-330 | one individualized compound I | Prodiamine |
| B-331 | one individualized compound I | Trifluralin |
| B-332 | one individualized compound I | Acifluorfen |
| B-333 | one individualized compound I | Bromoxynil |
| B-334 | one individualized compound I | Imazamethabenz |
| B-335 | one individualized compound I | Imazamox |
| B-336 | one individualized compound I | Imazapic |
| B-337 | one individualized compound I | Imazapyr |
| B-338 | one individualized compound I | Imazaquin |
| B-339 | one individualized compound I | Imazethapyr |
| B-340 | one individualized compound I | 2,4-Dichlorophenoxyacetic acid (2,4-D) |
| B-341 | one individualized compound I | Chloridazon |
| B-342 | one individualized compound I | Clopyralid |
| B-343 | one individualized compound I | Fluroxypyr |
| B-344 | one individualized compound I | Picloram |
| B-345 | one individualized compound I | Picolinafen |
| B-346 | one individualized compound I | Bensulfuron |
| B-347 | one individualized compound I | Chlorimuron-ethyl |
| B-348 | one individualized compound I | Cyclosulfamuron |
| B-349 | one individualized compound I | Iodosulfuron |
| B-350 | one individualized compound I | Mesosulfuron |
| B-351 | one individualized compound I | Metsulfuron-methyl |
| B-352 | one individualized compound I | Nicosulfuron |
| B-353 | one individualized compound I | Rimsulfuron |
| B-354 | one individualized compound I | Triflusulfuron |

TABLE B-continued

Composition comprising one indiviualized compound I and one further active substance from groups A) to O)

| Mixture | Component 1 | Component 2 |
|---|---|---|
| B-355 | one individualized compound I | Atrazine |
| B-356 | one individualized compound I | Hexazinone |
| B-357 | one individualized compound I | Diuron |
| B-358 | one individualized compound I | Florasulam |
| B-359 | one individualized compound I | Pyroxasulfone |
| B-360 | one individualized compound I | Bentazone |
| B-361 | one individualized compound I | Cinidon-ethyl |
| B-362 | one individualized compound I | Cinmethylin |
| B-363 | one individualized compound I | Dicamba |
| B-364 | one individualized compound I | Diflufenzopyr |
| B-365 | one individualized compound I | Quinclorac |
| B-366 | one individualized compound I | Quinmerac |
| B-367 | one individualized compound I | Mesotrione |
| B-368 | one individualized compound I | Saflufenacil |
| B-369 | one individualized compound I | Topramezone |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48 (6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

With due modification of the starting compounds, the procedures shown in the synthesis examples below were used to obtain further compounds I. The resulting compounds, together with physical data, are listed in Table I below.

I.1 Preparation of Strobilurin Type Compounds I

Example 1

Preparation of (Z)-5-[1-(4-Chloro-phenyl)-1H-pyrazol-3-yloxy]-2-[(E)-methoxyimino]-3-methyl-pent-3-enic acid methyl amide (I-6)

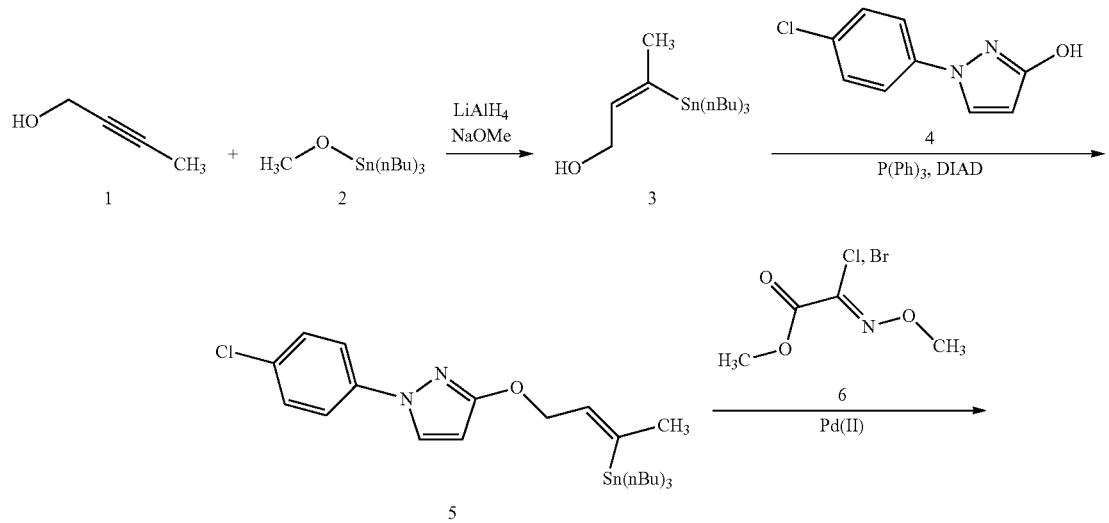

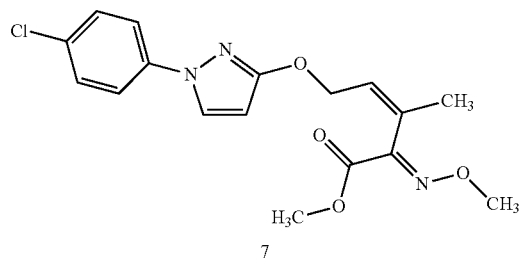

7

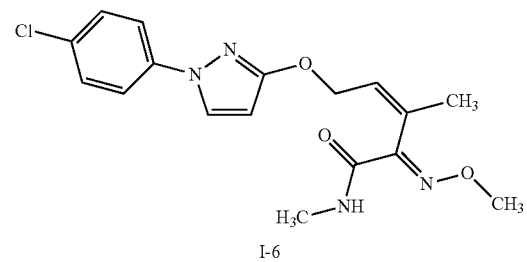

I-6

Ex. 1a (Z)-3-Tributylstannanyl-but-2-en-1-ol (3)

To 156.9 ml (156.9 mmol) of a 1 molar solution of lithium-aluminum-hydride in THF 0.77 g (14.3 mmol) sodium methylate have been added and the temperature has been lowered to 0° C. afterwards. Then a solution of 10.0 g (142.7 mmol) 2-butin-1-ol in 108 ml THF has been added dropwise with stirring at this temperature. Stirring was continued for 36 h at 4° C. Thereafter, at about 0° C., 28.6 ml (292.5 mmol) ethyl acetate was-added slowly while stirring. A strongly exothermic reaction was observed. Stirring was continued for 10 min without cooling. After cooling to about 0° C., 45.8 g (142.7 mmol) tri(n-butyl)stannyl-methanolate have been added dropwise while stirring. Stirring was continued for 2 d at 4° C. After addition of 112.9 g methanol stirring was continued for 1 h at ambient temperature. The reaction mixture was poured into 250 ml of water, extracted thrice with 150 ml diethyl ether each, the combined extracts were washed twice with 80 ml of water each, then once with 40 ml saturated aqueous sodium chloride solution, dried with sodium sulfate and concentrated in vacuo. Yield 48.6 g oil, which have been purified by chromatography on 300 g silica gel with hexane/MTBE (10:1). Final yield 34.6 g (67%) oil. δ=0.90 (m); 1.30 (m); 1.50 m); 1.97 (s); 4.02 (t); 6.27 (t).

Ex. 1b 1-(4-Chloro-phenyl)-3-((Z)-3-tributylstannanyl-but-2-enyloxy)-1H-pyrazole (5)

To 8.09 g (30.8 mmol) triphenylphosphine in 200 ml THF have been added with stirring at −75° C. 6.23 g (30.8 mmol) azodicarbonic acid diisopropyl ester. The mixture has been stirred at this temperature for 5 min. Then 10.39 g (28.8 mmol) (Z)-3-tributylstannanyl-but-2-en-1-ol have been added dropwise and stirred for 5 min at −75° C. After addition of 4.00 g (20.6 mmol) 1-(4-chlorophenyl)-3-hydroxypyrazole at −75° C. a red suspension was formed. The mixture was allowed to warm up to ambient temperature and stirred for 3 d. After removal of the solvents in vacuo 29 g oil have been collected and purified by chromatography on 120 g silica with MTBE/heptane. Yield 8.3 g (75%) oil. δ=0.85 (m); 0.95 (m); 1.30 (m); 1.50 m); 2.00 (s); 4.65 (d); 5.90 (d); 6.43 (t); 7.35 (d); 7.52 (d); 7.68 (d).

Ex. 1c (Z)-5-[1-(4-Chloro-phenyl)-1H-pyrazol-3-yloxy]-2-[(E)-methoxyimino]-3-methyl-pent-3-enic acid methyl ester (7)

3.00 g (5.58 mmol) 1-(4-Chloro-phenyl)-3-((Z)-3-tributyl-stannanyl-but-2-enyloxy)-1H-pyrazole, 1.15 g (5.86 mmol) hydroxamic acid bromide (6), 0.155 g (0.67 mmol) tri(2-furyl)phosphine and 96 mg (0.17 mmol) bis(dibenzylidenac-etone)-palladium have been stirred in 10 ml 1,4-dioxane for 4 d at about 80° C. After removal of the solvents in vacuo 4.3 g oil have been collected and purified by chromatography on 70 g silica with MTBE/heptane/1% triethylamine. Yield 1.2 g (59%) oil. δ=1.95 (s); 3.85 (s); 4.07 (s); 4.58 (d); 5.85 (d); 5.93 (t); 7.35 (d); 7.52 (d); 7.65 (d).

Ex. 1d (Z)-5-[1-(4-Chloro-phenyl)-1H-pyrazol-3-yloxy]-2-[(E)-methoxyimino]-3-methyl-pent-3-enic acid methyl amide (I-6)

120 mg (0.33 mmol) (Z)-5-[1-(4-chloro-phenyl)-1H-pyrazol-3-yloxy]-2-[(E)-methoxyimino]-3-methyl-pent-3-enic acid methyl ester and 0.99 ml (1.98 mmol) of a 2-molar solution of methyl amine in THF have been stirred overnight at ambient temperature in 2.0 ml of THF and 0.5 ml of water. After removal of the solvent in vacuo the product (120 mg) was collected in quantitative yield and good purity. Melting point 129-130° C.

Example 2

(Z)-5-[1-(4-Chloro-phenyl)-1H-pyrazol-3-yloxy]-2-[1-methoxy-meth-(E)-ylidene]-3-methyl-pent-3-enoic acid methyl ester (compound I-7)

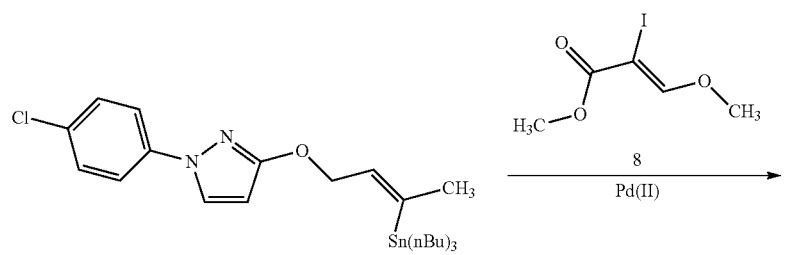

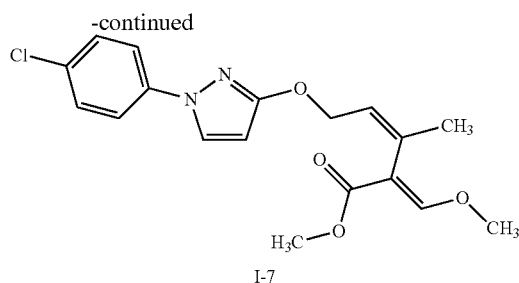
I-7

1.50 g (2.79 mmol) 1-(4-Chloro-phenyl)-3-((Z)-3-tributyl-stannanyl-but-2-enyloxy)-1H-pyrazole (5), 0.81 g (3.35 mmol) of ester compound (8) [Chem Comm 4, 423-425, (2006)], 0.223 g (0.28 mmol) [(R)-(+)-2,2"-Bis(diphenylphosphino)-1,1"-bisnaphthyl]-palladium(II)chloride have been stirred in 14 ml 1,4-dioxane for 4.5 d at about 100° C. After removal of the solvents in vacuo the crude product has been collected, which has been purified by chromatography on 50 g silica with MTBE/hexane/2% triethylamine. Yield 0.12 g, melting point 123-125° C.

Example 3

Methyl N—[(Z)-3-[1-(4-chlorophenyl)pyrazol-3-yl]oxy-1-methyl-prop-1-enyl]-N-methyl-carbamate (I-10)

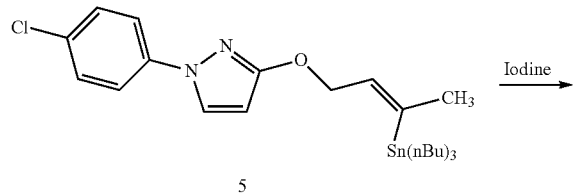

Ex. 3a 1-(4-chlorophenyl)-3-[(Z)-3-iodobut-2-enoxy]pyrazole (10)

To 10.0 g (18.6 mmol) 1-(4-chloro-phenyl)-3-((Z)-3-tributylstannanyl-but-2-enyloxy)-1H-pyrazole in 100 ml methylene chloride have been added 4.7 g (18.6 mmol) iodine at ambient temperature with stirring which was continued for 3 h. After removal of the solvents in vacuo the crude product was dissolved in 200 ml MTBE. 100 ml 20% aqueous potassium fluoride solution have been added and the mixture was stirred for 2 h at ambient temperature. The aqueous layer was separated and extracted with 20 ml methyl-tert.-butyl ether twice. The combined organic phases have been washed twice with 20 ml of water each, dried with sodium sulfate, and the solvents were removed in vacuo. The crude product (7.2 g) has been purified by chromatography on 50 g silica with methyl-tert.-butylether/hexane (1:20). Yield 5.9 g, melting point 75-77° C.

Ex. 3b

Methyl N—[(Z)-3-[1-(4-chlorophenyl)pyrazol-3-yl]oxy-1-methyl-prop-1-enyl]-N-methyl-carbamate 1.50 g (4.00 mmol) 1-(4-chlorophenyl)-3-[(Z)-3-iodobut-2-enoxy]pyrazole, 0.43 g (4.81 mmol) N-methylcarbamic

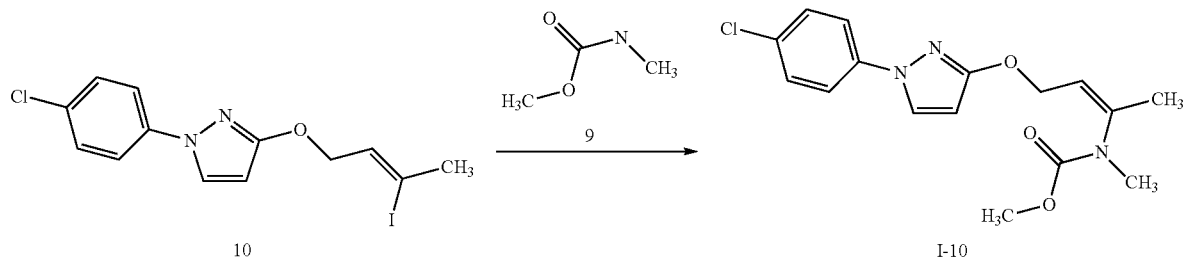

acid methyl ester (9), 76 mg (0.4 mmol) copperiodide, 1.27 g (6.00 mmol) potassium phosphate and 71 mg (0.80 mmol) N,N'-dimethylethylene diamine in 14 ml toluene have been stirred for 1.5 d at 100° C. After removal of the solvents in vacuo the crude product has been purified by chromatography on 50 g silica with MTBE/hexane (1:3). Yield 0.67 g. $^1$H-NMR (CDCl$_3$): δ=1.90 (s); 3.05 (s); 3.70 (s); 4.68 (m); 5.63 (m); 5.90 (d); 7.35 (m); 7.55 (m); 7.68 (d).

Example 4

(Z,2E)-5-[1-(4-chlorophenyl)pyrazol-3-yl]oxy-2-methoxyimino-N,4-dimethyl-pent-3-enamide (compound I-79)

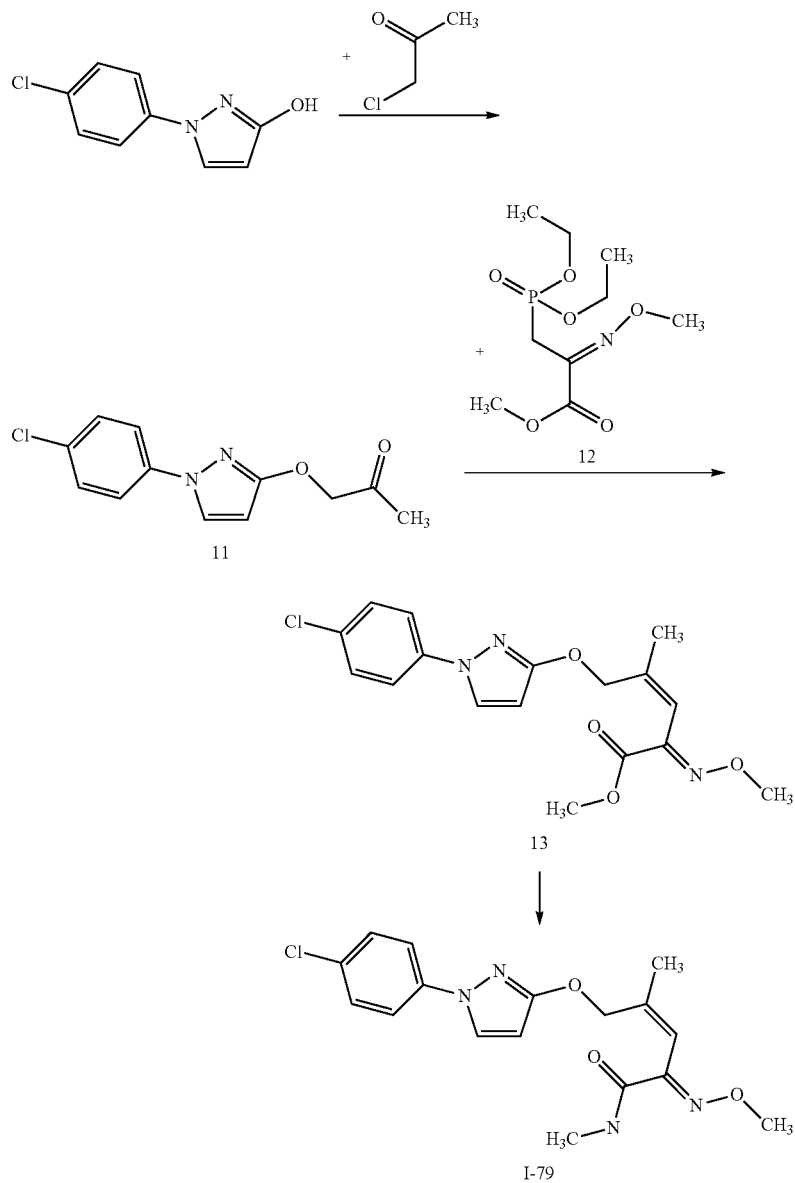

chloride solution and extracted with ethyl acetate three times. The combined extracts have been washed with 10% lithium chloride solution twice and dried with sodium sulfate. After removal of the solvent in vacuo the crude product has been purified by chromatography on silica. Yield 6.5 g. The product was used for the next step.

Ex. 4a

1-[1-(4-Chlorophenyl)pyrazol-3-yl]oxypropan-2-one (11)

5.50 g (28.3 mmol) 1-(4-chlorophenyl)pyrazol-3-ol, 3.91 g (28.3 mmol) potassium carbonate and 50 mg sodium iodide in 30 ml DMF have been stirred for 5 min at ambient temperature. Then 2.62 g (28.3 mmol) chloroacetone have been added dropwise while stirring which was continued at 60° C. for 5 h. The mixture was poured into excess 10% aqueous lithium

Ex. 4b

Methyl(Z,2E)-5-[1-(4-chlorophenyl)pyrazol-3-yl]oxy-2-methoxyimino-4-methyl-pent-3-enoate and E-isomer (13)

To 5.26 g (21.0 mmol) 1-[1-(4-chlorophenyl)pyrazol-3-yl]oxypropan-2-one and 7.20 g (26.9 mmol) methyl (2Z)-3-diethoxyphosphoryl-2-methoxyimino-propanoate (which can be prepared as described for the dimethoxy derivative [(Tetrahedron Let 29, 3361-3364 (1988)] in 100 ml THF have been added at ambient temperature with stirring 2.59 g (23.1 mmol) potassium tert.-butylate. Stirring was continued over night. After removal of the solvent in vacuo the mixture was purified by chromatography on silica with heptane/ethyl acetate. 1.07 g of a 80:20 E:Z-mixture have been collected. This has been used directly for the next step.

Ex. 4c

Z,2E)-5-[1-(4-chlorophenyl)pyrazol-3-yl]oxy-2-methoxyimino-N,4-dimethyl-pent-3-enamide 0.68 g (1.87 mmol) methyl(Z,2E)-5-[1-(4-chlorophenyl)pyrazol-3-yl]oxy-2-methoxyimino-4-methyl-pent-3-enoate and E-isomer from the previous reaction have been dissolved in 3.0 ml THF. 2.0 ml 40% aqueous methylamine have been added at ambient temperature with stirring which was continued over night. After removal of the solvent in vacuo the mixture was purified by chromatography on silica with a heptane/ethyl acetate gradient. 90 mg of the desired Z-isomer have been collected. $^1$H-NMR (CDCl$_3$): δ=2.03 (s); 2.85 (d); 3.97 (s); 4.64 (s); 5.87 (s); 6.02 (d); 6.65 (br); 7.35 (d); 7.50 (d); 7.67 (d).

Example 5

Methyl N—[(Z)-3-[1-(4-chlorophenyl)pyrazol-3-yl]oxy-1-methyl-prop-1-enyl]-N-methoxy-carbamate (I-1)

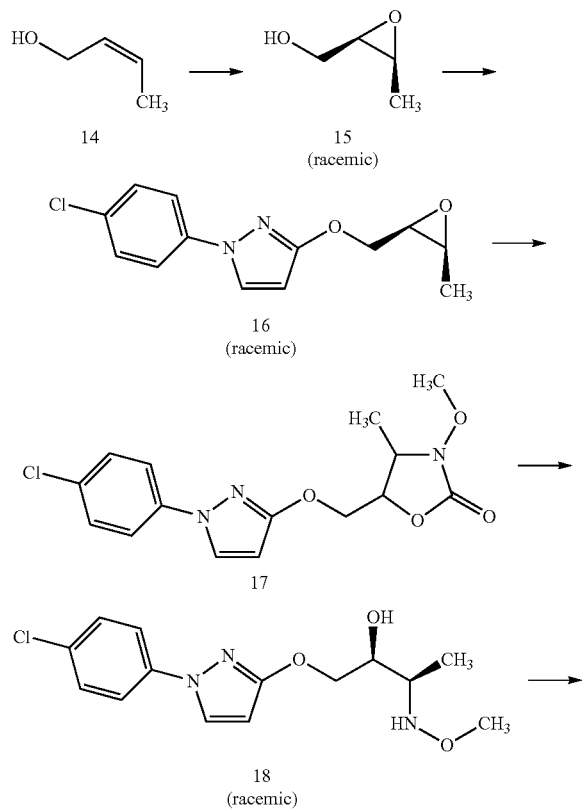

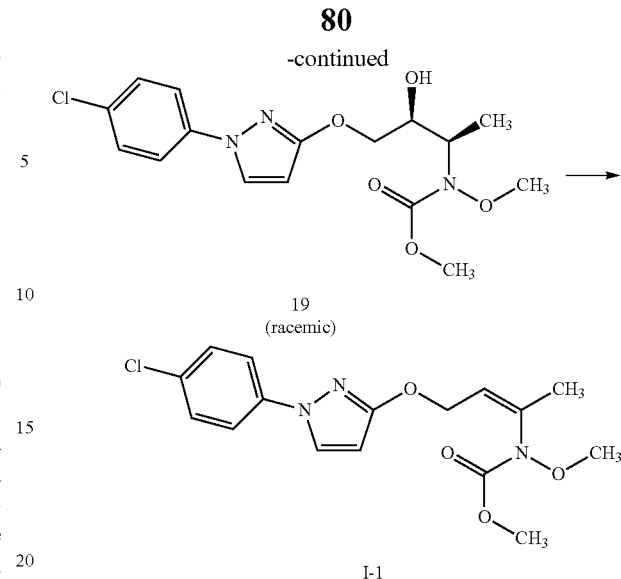

Ex. 5a

Cis-3-methyloxiran-2-yl]methanol (15)

To 10.0 g (138.7 mmol) Z-but-2-en-1-ol in 140 ml dichloromethane (DCM) 37.6 g (152.6 mmol) 3-chloroperbenzoic acid (70% purity) have been added at 0-5° C. in small portions with stirring. Stirring was continued at 0° C. for 2 h. 35.0 g calcium hydroxide have been added at 0-5° C. with stirring which was continued for about 2 h at 0° C. The precipitate was filtered off, washed with DCM, and the filtrates dried with sodium sulfate. The solvent was largely removed at 380 mbar/30° C. The crude product (15.0 g, purity 75%) was used without further purification.

Ex. 5b

Racemic 1-(4-chlorophenyl)-3-[[(2R,3S)-3-methyloxiran-2-yl]methoxy]pyrazole (16)

To 28.3 g (107.9 mmol) triphenylphosphine and 15.0 g (127.7 mmol) cis-3-methyloxiran-2-yl]methanol (15) from the preceding experiment in 400 ml THF have been added with stirring at −75° C. 22.9 g (113.0 mmol) azodicarbonic acid diisopropyl ester. The mixture has been stirred at this temperature for 5 min. Then 20.0 g (102.8 mmol) 1-(4-chlorophenyl)-3-hydroxypyrazole have been added with stirring at −70° C. The mixture was allowed to warm up to ambient temperature and stirred for about 1d. After removal of the solvents in vacuo the crude product was stirred with 200 ml of diisopropylether from which 42 g of a solid substance have been collected and further purified by chromatography on 330 g silica with MTBE/heptane. Yield 22.5 g (82%).

Ex. 5c

5-[[1-(4-chlorophenyl)pyrazol-3-yl]oxymethyl]-3-methoxy-4-methyl-oxazolidin-2-one (17)

To 1.08 g (10.0 mmol) methyl N-methoxycarbamate in 17 ml DMSO have been added with stirring at ambient temperature 1.00 g (8.9 mmol) potassium tert.-butylate. Stirring has been continued for 5 min before 2.00 g (7.56 mmol) 1-(4-chloro-phenyl)-3-[[(2R,3S)-3-methyloxiran-2-yl]methoxy]

pyrazole have been added. The mixture was stirred at 90° C. for 20 h. After cooling to ambient temperature the reaction mixture was poured into 150 ml of water, extracted thrice with 30 ml ethyl acetate each, the combined extracts have been dried with sodium sulfate and the solvent removed in vacuo. The crude product (2.5 g) was used without further purification.

Ex. 5d

Racemic (2S,3R-1-[1-(4-chlorophenyl)pyrazol-3-yl] oxy-3-(methoxyamino)butan-2-ol (18)

To 10.0 g (30.0 mmol) 5-[[1-(4-chlorophenyl)pyrazol-3-yl]oxymethyl]-3-methoxy-4-methyl-oxazolidin-2-one in 100 ml ethanol has been added at ambient temperature with stirring 14.6 g (40.0 mmol) 21% sodium ethylate solution (in ethanol) and stirred over night. The solvent was largely removed in vacuo and the remaining mixture poured into 250 ml aqueous sodium dihydrogenphosphate solution, extracted thrice with 150 ml ethyl acetate each, dried with sodium sulfate to yield 8.7 g of an oil after evaporation of the solvent in vacuo. Further purified by chromatography on 120 g silica with MTBE/heptane. Yield 4.0 g (43%). $^1$H-NMR (CDCl$_3$): δ=1.22 (d); 3.17 (m); 3.57 (s); 3.91 (m); 4.33 (m); 4.47 (m); 5.93 (s); 7.35 (d); 7.52 (d); 7.68 (s).

Ex. 5e

Racemic methyl N-[(1R,2S)-3-[1-(4-chlorophenyl) pyrazol-3-yl]oxy-2-hydroxy-1-methyl-propyl]-N-methoxy-carbamate (19)

To 1.00 g (3.2 mmol) Racemic (2S,3R-1-[1-(4-chlorophenyl)pyrazol-3-yl]oxy-3-(methoxyamino)butan-2-ol in 7 ml THF 0.28 g (3.5 mmol) sodium hydrogencarbonate has been added. Then 0.33 g (3.5 mmol) methyl chloroformiate has been added dropwise with stirring at ambient temperature. Stirring has been continued over night. The reaction mixture was poured into 10 ml of water, extracted thrice with 10 ml MTBE each, the combined extracts dried with sodium sulfate, and the solvent removed in vacuo. The crude product (1.3 g) was used without further purification.

Ex. 5f

Methyl N—[(Z)-3-[1-(4-chlorophenyl)pyrazol-3-yl] oxy-1-methyl-prop-1-enyl]-N-methoxy-carbamate (I-1)

To 3.50 g (9.46 mmol) racemic methyl N-[(1R,2S)-3-[1-(4-chlorophenyl)pyrazol-3-yl]oxy-2-hydroxy-1-methyl-propyl]-N-methoxy-carbamate in 13 ml THF 2.61 g (9.94 mmol) triphenylphoshin has been added with stirring at ambient temperature. The mixture was cooled to −15° C. Then 2.11 g (10.41 mmol) azodicarbonic acid diisopropyl ester has been added with stirring which was continued for 1 h at 0° C. and for about 1d at ambient temperature. After removal of the solvents in vacuo the crude product was further purified by chromatography on 25 g silica with MTBE/heptane/1% triethylamine. $^1$H-NMR (CDCl$_3$): δ=1.93 (s); 3.72 (s); 3.81 (s); 4.78 (d); 5.73 (t); 5.90 (d); 7.36 (d); 7.55 (d); 7.70 (d).

TABLE I

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-1 | CH$_3$ | H | R3-1 | R4-4, R$^5$ = OCH$_3$ | O | Y-1 | δ = 1.93 (s); 3.72 (s); 3.81 (s); 4.78 (d); 5.73 (t); 5.90 (d); 7.36 (d); 7.55 (d); 7.70 (d) |
| I-2 | CH$_3$ | H | R3-1 | R4-4, R$^5$ = OCH$_3$ | NH | Y-1 | |
| I-3 | CH$_3$ | H | R3-1 | R4-3 | O | Y-1 | |
| I-4 | CH$_3$ | H | R3-1 | R4-3 | NH | Y-1 | |
| I-5 | CH$_3$ | H | R3-1 | R4-1 | O | Y-1 | 88-89° C. |
| I-6 | CH$_3$ | H | R3-1 | R4-1 | NH | Y-1 | 130° C. |
| I-7 | CH$_3$ | H | R3-1 | R4-2 | O | Y-1 | 123-125° C. |
| I-8 | CH$_3$ | H | R3-1 | R4-2 | NH | Y-1 | |
| I-9 | CH$_3$ | H | R3-1 | R4-7 | | Y-1 | |
| I-10 | CH$_3$ | H | R3-1 | R4-4, R$^5$ = CH$_3$ | O | Y-1 | δ = 1.90 (s); 3.05 (s); 3.70 (s); 4.68 (m); 5.63 (m); 5.90 (d); 7.35 (m); 7.55 (m); 7.68 (d) |
| I-11 | CH$_3$ | H | R3-2 | R4-1 | NH | Y-1 | δ = 1.95 (s); 2.85 (d); 3.95 (s); 4.55 (m); 5.87 (m); 5.95 (m); 6.70 (br); 6.95 (m); 7.73 (m); 7.80 (m) |
| I-12 | CH$_3$ | H | R3-3 | R4-1 | NH | Y-1 | δ = 1.95 (s); 2.27 (s); 2.80 (d); 3.95 (s); 4.52 (m); 5.83 (d); 5.93 (m); 6.75 (br); 6.95 (m); 7.30 (m) |
| I-13 | CH$_3$ | H | R3-4 | R4-1 | NH | Y-1 | δ = 1.93 (s); 2.38 (s); 2.80 (d); 3.95 (s); 4.55 (m); 5.88 (d); 5.95 (m); 6.75 (br); 7.13 (m); 7.28 (m); 7.41 (d); 7.64 (d) |
| I-14 | CH$_3$ | H | R3-5 | R4-1 | NH | Y-1 | 125-127° C. |
| I-15 | CH$_3$ | H | R3-6 | R4-1 | NH | Y-1 | δ = 1.95 (s); 2.85 (d); 3.95 (s); 4.55 (m); 5.90 (d); 5.95 (m); 6.70 (br); 7.32 (m); 7.50 (s); 7.54 (d); 7.70 (d) |
| I-16 | CH$_3$ | H | R3-7 | R4-1 | NH | Y-1 | δ = 1.95 (s); 2.90 (d); 3.97 (s); 4.56 (m); 5.88 (d); 5.94 (m); 6.70 (br); 7.45 (m); 7.64 (s); 7.72 (d) |
| I-17 | CH$_3$ | H | R3-8 | R4-1 | NH | Y-1 | |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-18 | CH$_3$ | H | R3-9 | R4-1 | NH | Y-1 | δ = 1.95 (s); 2.33 (s); 2.88 (d); 3.97 (s); 4.56 (m); 5.85 (m); 5.95 (m); 6.70 (br); 7.03 (t); 7.30 (m); 7.44 (m); 7.62 (m) |
| I-19 | CH$_3$ | H | R3-10 | R4-1 | NH | Y-1 | |
| I-20 | CH$_3$ | H | R3-11 | R4-1 | NH | Y-1 | δ = 1.95 (s); 2.25 (s); 2.30 (s); 2.87 (d); 3.97 (s); 4.56 (m); 5.85 (d); 5.95 (m); 6.73 (br); 7.15 (d); 7.27 (m); 7.35 (d); 7.63 (d) |
| I-21 | CH$_3$ | H | R3-12 | R4-1 | NH | Y-1 | |
| I-22 | CH$_3$ | H | R3-13 | R4-1 | NH | Y-1 | |
| I-23 | CH$_3$ | H | R3-14 | R4-1 | NH | Y-1 | |
| I-24 | CH$_3$ | H | R3-15 | R4-1 | NH | Y-1 | |
| I-25 | CH$_3$ | H | R3-16 | R4-1 | NH | Y-1 | |
| I-26 | CH$_3$ | H | R3-17 | R4-1 | NH | Y-1 | |
| I-27 | CH$_3$ | H | R3-14 | R4-1 | NH | Y-1 | |
| I-28 | CH$_3$ | H | R3-18 | R4-1 | NH | Y-1 | δ = 1.95 (s); 2.90 (d); 3.97 (s); 4.57 (m); 5.87 (m); 5.95 (m); 6.70 (br); 7.07 (m); 7.33 (m); 7.55 (m); 7.64 (m) |
| I-29 | CH$_3$ | H | R3-19 | R4-1 | NH | Y-1 | δ = 1.95 (s); 2.90 (d); 3.97 (s); 4.58 (m); 5.88 (d); 5.94 (m); 6.70 (br); 7.15 (m); 7.30 (m); 7.43 (m); 7.64 (s); 7.70 (d) |
| I-30 | CH$_3$ | H | R3-20 | R4-1 | NH | Y-1 | |
| I-31 | CH$_3$ | H | R3-21 | R4-1 | NH | Y-1 | |
| I-32 | CH$_3$ | H | R3-22 | R4-1 | NH | Y-1 | δ = 1.95 (s); 2.37 (s); 2.87 (d); 3.95 (s); 4.55 (m); 5.86 (d); 5.93 (m); 6.70 (br); 7.20 (m); 7.45 (m); 7.65 (d) |
| I-33 | CH$_3$ | H | R3-23 | R4-1 | NH | Y-1 | δ = 1.23 (m); 1.95 (s); 2.64 (m); 2.87 (d); 3.95 (s); 4.58 (m); 5.87 (d); 5.95 (m); 6.70 (br); 7.25 (m); 7.48 (m); 7.67 (d) |
| I-34 | CH$_3$ | H | R3-24 | R4-1 | NH | Y-1 | δ = 1.95 (s); 2.90 (d); 3.97 (s); 4.58 (m); 5.92 (m); 6.70 (br); 7.67 (m); 7.75 (d) |
| I-35 | CH$_3$ | H | R3-25 | R4-1 | NH | Y-1 | |
| I-36 | CH$_3$ | H | R3-26 | R4-1 | NH | Y-1 | |
| I-37 | CH$_3$ | H | R3-58 | R4-1 | NH | Y-1 | |
| I-38 | CH$_3$ | H | R3-28 | R4-1 | NH | Y-1 | |
| I-39 | CH$_3$ | H | R3-29 | R4-1 | NH | Y-1 | |
| I-40 | CH$_3$ | H | R3-30 | R4-1 | NH | Y-1 | |
| I-41 | CH$_3$ | H | R3-31 | R4-1 | NH | Y-1 | |
| I-42 | CH$_3$ | H | R3-32 | R4-1 | NH | Y-1 | |
| I-43 | CH$_3$ | H | R3-33 | R4-1 | NH | Y-1 | |
| I-44 | CH$_3$ | H | R3-34 | R4-1 | NH | Y-1 | |
| I-45 | CH$_3$ | H | R3-35 | R4-1 | NH | Y-1 | |
| I-46 | CH$_3$ | H | R3-36 | R4-1 | NH | Y-1 | |
| I-47 | CH$_3$ | H | R3-37 | R4-1 | NH | Y-1 | |
| I-48 | CH$_3$ | H | R3-38 | R4-1 | NH | Y-1 | |
| I-49 | CH$_3$ | H | R3-39 | R4-1 | NH | Y-1 | |
| I-50 | CH$_3$ | H | R3-40 | R4-1 | NH | Y-1 | |
| I-51 | CH$_3$ | H | R3-41 | R4-1 | NH | Y-1 | |
| I-52 | CH$_3$ | H | R3-42 | R4-1 | NH | Y-1 | |
| I-53 | CH$_3$ | H | R3-43 | R4-1 | NH | Y-1 | |
| I-54 | CH$_3$ | H | R3-44 | R4-1 | NH | Y-1 | |
| I-55 | CH$_3$ | H | R3-45 | R4-1 | NH | Y-1 | |
| I-56 | CH$_3$ | H | R3-46 | R4-1 | NH | Y-1 | |
| I-57 | CH$_3$ | H | R3-47 | R4-1 | NH | Y-1 | |
| I-58 | CH$_3$ | H | R3-45 | R4-1 | NH | Y-1 | |
| I-59 | CH$_3$ | H | R3-49 | R4-1 | NH | Y-1 | |
| I-60 | CH$_3$ | H | R3-50 | R4-1 | NH | Y-1 | |
| I-61 | CH$_3$ | H | R3-51 | R4-1 | NH | Y-1 | |
| I-62 | CH$_3$ | H | R3-52 | R4-1 | NH | Y-1 | |
| I-63 | CH$_3$ | H | R3-53 | R4-1 | NH | Y-1 | |
| I-64 | CH$_3$ | H | R3-54 | R4-1 | NH | Y-1 | |
| I-65 | CH$_3$ | H | R3-55 | R4-1 | NH | Y-1 | |
| I-66 | CH$_3$ | H | R3-56 | R4-1 | NH | Y-1 | |
| I-67 | CH$_3$ | H | R3-57 | R4-1 | NH | Y-1 | |
| I-68 | CH$_3$ | H | R3-58 | R4-4, R$^5$ = OCH$_3$ | O | Y-1 | |
| I-69 | CH$_3$ | H | R3-58 | R4-4, R$^5$ = OCH$_3$ | NH | Y-1 | |
| I-70 | CH$_3$ | H | R3-58 | R4-3 | O | Y-1 | |

TABLE I-continued

Compounds of formula I with physical data (melting point [° C.];
$^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-71 | CH$_3$ | H | R3-58 | R4-3 | NH | Y-1 | |
| I-72 | CH$_3$ | H | R3-27 | R4-1 | O | Y-1 | |
| I-73 | CH$_3$ | H | R3-58 | R4-2 | O | Y-1 | |
| I-74 | CH$_3$ | H | R3-58 | R4-2 | NH | Y-1 | |
| I-75 | CH$_3$ | H | R3-58 | R4-7 |  | Y-1 | |
| I-76 | C$_2$H$_5$ | H | R3-1 | R4-1 | NH | Y-1 | |
| I-77 | C$_2$H$_5$ | H | R3-2 | R4-1 | NH | Y-1 | |
| I-78 | C$_2$H$_5$ | H | R3-58 | R4-1 | NH | Y-1 | |
| I-79 | H | CH$_3$ | R3-1 | R4-1 | NH | Y-1 | δ = 2.03 (s); 2.85 (d); 3.97 (s); 4.64 (s); 5.87 (s); 6.02 (d); 6.65 (br); 7.35 (d); 7.50 (d); 7.67 (d) |
| I-80 | H | CH$_3$ | R3-1 | R4-1 | O | Y-1 | |
| I-81 | CH$_3$ | H | R3-1 | R4-1 | NH | Y-3 | |
| I-82 | CH$_3$ | H | R3-59 | R4-1 | NH | Y-1 | δ = 1.95 (s); 2.16 (s); 2.18 (s); 2.30 (s); 2.90 (s); 3.97 (s); 4.33 (m); 4.65 (m); 5.30 (m); 5.87 (m); 6.07 (m); 6.55 (s); 6.65 (br); 6.96 (s) |
| I-83 | CH$_3$ | H | R3-60 | R4-1 | NH | Y-1 | δ = 1.95 (s); 2.22 (s); 2.90 (d); 3.95 (s); 4.35 (m); 4.67 (m); 5.30 (m); 5.88 (m); 6.07 (m); 6.65 (br); 6.73 (d); 7.35 (d); 7.43 (s) |
| I-84 | CH$_3$ | H | R3-61 | R4-1 | NH | Y-1 | δ = 1.95 (s); 2.15 (s); 2.18 (s); 2.28 (s); 2.90 (d); 3.95 (s); 4.33 (m); 4.67 (s); 5.39 (d); 5.43 (d); 5.88 (m); 6.57 (s); 6.65 (br); 6.95 (s) |
| I-85 | CH$_3$ | H | R3-62 | R4-1 | NH | Y-1 | δ = 1.95 (s); 2.21 (s); 2.25 (s); 2.89 (d); 3.95 (s); 4.35 (m); 4.70 (s); 5.39 (d); 5.44 (d); 5.90 (m); 6.65 (br); 6.73 (d); 7.40 (d); 7.45 (s) |
| I-86 | CH$_3$ | H | R3-63 | R4-1 | O | Y-1 | δ = 1.73 (m); 1.93 (s); 2.15 (s); 2.30 (s); 3.85 (s); 4.05 (s); 4.33 (m); 4.60 (m); 5.75 (s); 5.85 (m); 6.55 (s); 6.95 (s) |
| I-87 | CH$_3$ | H | R3-64 | R4-1 | O | Y-1 | δ = 1.95 (s); 2.12 (s); 2.14 (s); 2.30 (s); 3.85 (s); 4.07 (s); 4.35 (m); 4.63 (m); 5.85 (m); 6.15 (m); 6.27 (m); 6.55 (s); 6.97 (s) |
| I-88 | CH$_3$ | H | R3-65 | R4-1 | O | Y-1 | δ = 1.95 (s); 2.17 (s); 2.19 (s); 3.85 (s); 4.05 (s); 4.35 (m); 4.65 (m); 5.87 (m); 6.17 (m); 6.31 (m); 6.72 (d); 7.35 (d); 7.43 (s). |
| I-89 | CH$_3$ | H | R3-66 | R4-1 | NH | Y-1 | δ = 1.95 (s); 2.12 (s); 2.14 (s); 2.30 (s); 2.90 (d); 3.95 (s); 3.97 (s); 4.32 (m); 5.87 (m); 6.57 (s); 6.65 (br); 6.97 (s) |
| I-90 | CH$_3$ | H | R3-63 | R4-1 | NH | Y-1 | δ = 1.73 (m); 1.93 (s); 2.15 (s); 2.30 (s); 2.90 (d); 3.95 (s); 4.33 (m); 4.55 (m); 5.75 (m); 5.90 (m); 6.57 (s); 6.65 (br); 6.95 (s) |
| I-91 | CH$_3$ | H | R3-67 | R4-1 | NH | Y-1 | δ = 1.73 (m); 1.93 (s); 2.18 (s); 2.20 (s); 2.90 (d); 3.95 (s); 4.35 (m); 4.60 (m); 5.75 (m); 5.90 (m); 6.55 (br); 6.73 (m); 7.35 (m); 7.43 (s) |
| I-92 | CH$_3$ | H | R3-64 | R4-1 | NH | Y-1 | δ = 1.95 (s); 2.15 (s); 2.30 (s); 2.90 (d); 3.95 (s); 4.33 (m); 4.60 (m); 5.87 (m); 6.15 (m); 6.27 (m); 6.57 (s); 6.65 (br); 6.95 (s) |
| I-93 | CH$_3$ | H | R3-65 | R4-1 | NH | Y-1 | δ = 1.95 (s); 2.19 (s); 2.21 (s); 2.90 (d); 3.95 (s); 4.35 (m); 4.65 (m); 5.90 (m); 6.17 (m); 6.31 (m); 6.65 (br); 6.75 (d); 7.35 (m); 7.43 (s) |
| I-94 | CH$_3$ | H | R3-59 | R4-1 | O | Y-1 | δ = 1.95 (s); 2.15 (s); 2.30 (s); 3.85 (s); 4.07 (s); 4.33 (m); 4.63 (m); 5.30 (m); 5.87 (m); 6.07 (m); 6.53 (s); 6.97 (s) |
| I-95 | CH$_3$ | H | R3-60 | R4-1 | O | Y-1 | δ = 1.93 (s); 2.22 (s); 3.85 (s); 4.07 (s); 4.37 (m); 4.67 (m); 5.30 (m); 5.87 (m); 6.07 (m); 6.70 (d); 7.37 (m); 7.45 (s) |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-96 | CH$_3$ | H | R3-61 | R4-1 | O | Y-1 | δ = 1.95 (s); 2.15 (s); 2.17 (s); 2.28 (s); 3.87 (s); 4.07 (s); 4.33 (m); 4.67 (s); 5.40 (d); 5.43 (d); 5.87 (m); 6.53 (s); 6.95 (s) |
| I-97 | CH$_3$ | H | R3-62 | R4-1 | O | Y-1 | δ = 1.95 (s); 2.21 (s); 2.23 (s); 3.85 (s); 4.05 (s); 4.37 (m); 4.70 (s); 5.39 (d); 5.42 (d); 5.87 (m); 6.70 (d); 7.38 (m); 7.45 (s) |
| I-98 | CH$_3$ | H | R3-68 | R4-1 | O | Y-1 | δ = 1.23 (t); 1.87 (s); 2.08 (s); 2.27 (s); 3.70 (s); 3.95 (s); 4.10 (q); 4.30 (m); 5.90 (m); 6.65 (s); 7.00 (s) |
| I-99 | CH$_3$ | H | R3-69 | R4-1 | O | Y-1 | |
| I-100 | CH$_3$ | H | R3-69 | R4-1 | NH | Y-1 | |
| I-101 | CH$_3$ | H | R3-69 | R4-4, R$^5$ = OCH$_3$ | O | Y-1 | |
| I-102 | CH$_3$ | H | R3-70 | R4-1 | O | Y-6 | |
| I-103 | CH$_3$ | H | R3-70 | R4-1 | NH | Y-6 | |
| I-104 | CH$_3$ | H | R3-70 | R4-4, R$^5$ = OCH$_3$ | O | Y-6 | |
| I-105 | CH$_3$ | H | R3-71 | R4-1 | O | Y-4 | |
| I-106 | CH$_3$ | H | R3-71 | R4-1 | NH | Y-4 | |
| I-107 | CH$_3$ | H | R3-71 | R4-4, R$^5$ = OCH$_3$ | O | Y-4 | |
| I-108 | CH$_3$ | H | R3-72 | R4-1 | NH | Y-1 | |
| I-109 | CH$_3$ | H | R3-72 | R4-1 | O | Y-1 | |
| I-110 | CH$_3$ | H | R3-72 | R4-4, R$^5$ = OCH$_3$ | O | Y-1 | |
| I-111 | CH$_3$ | H | R3-72 | R4-1 | NH | Y-2 | |
| I-112 | CH$_3$ | H | R3-72 | R4-1 | O | Y-2 | |
| I-113 | CH$_3$ | H | R3-72 | R4-4, R$^5$ = OCH$_3$ | O | Y-2 | |
| I-114 | CH$_3$ | H | R3-1 | R4-4, R$^5$ = OCH$_3$ | O | Y-2 | |
| I-115 | CH$_3$ | H | R3-1 | R4-4, R$^5$ = OCH$_3$ | NH | Y-2 | |
| I-116 | CH$_3$ | H | R3-1 | R4-3 | O | Y-2 | |
| I-117 | CH$_3$ | H | R3-1 | R4-3 | NH | Y-2 | |
| I-118 | CH$_3$ | H | R3-1 | R4-1 | O | Y-2 | |
| I-119 | CH$_3$ | H | R3-1 | R4-1 | NH | Y-2 | |
| I-120 | CH$_3$ | H | R3-1 | R4-2 | O | Y-2 | |
| I-121 | CH$_3$ | H | R3-1 | R4-2 | NH | Y-2 | |
| I-122 | CH$_3$ | H | R3-1 | R4-7 | | Y-2 | |
| I-123 | CH$_3$ | H | R3-1 | R4-4, R$^5$ = CH$_3$ | O | Y-2 | |
| I-124 | CH$_3$ | H | R3-73 | R4-1 | NH | Y-1 | |
| I-125 | CH$_3$ | H | R3-74 | R4-1 | NH | Y-1 | |
| I-126 | CH$_3$ | H | R3-75 | R4-1 | NH | Y-1 | |
| I-127 | CH$_3$ | H | R3-76 | R4-1 | NH | Y-1 | |
| I-128 | CH$_3$ | H | R3-77 | R4-1 | NH | Y-1 | |
| I-129 | CH$_3$ | H | R3-78 | R4-1 | NH | Y-1 | |
| I-130 | CH$_3$ | H | R3-78 | R4-1 | NH | Y-1 | |
| I-131 | CH$_3$ | H | R3-80 | R4-1 | NH | Y-1 | |
| I-132 | CH$_3$ | H | R3-81 | R4-1 | NH | Y-1 | |
| I-133 | CH$_3$ | H | R3-82 | R4-1 | NH | Y-1 | |
| I-134 | CH$_3$ | H | R3-83 | R4-1 | NH | Y-1 | |
| I-135 | CH$_3$ | H | R3-84 | R4-1 | NH | Y-1 | |
| I-136 | CH$_3$ | H | R3-85 | R4-1 | NH | Y-1 | |
| I-137 | CH$_3$ | H | R3-86 | R4-1 | NH | Y-1 | |
| I-138 | CH$_3$ | H | R3-87 | R4-1 | NH | Y-1 | |
| I-139 | CH$_3$ | H | R3-88 | R4-1 | NH | Y-1 | |
| I-140 | CH$_3$ | H | R3-89 | R4-1 | NH | Y-1 | |
| I-141 | CH$_3$ | H | R3-90 | R4-1 | NH | Y-1 | |
| I-142 | CH$_3$ | H | R3-91 | R4-1 | NH | Y-1 | |
| I-143 | CH$_3$ | H | R3-92 | R4-1 | NH | Y-1 | |
| I-144 | CH$_3$ | H | R3-93 | R4-1 | NH | Y-1 | |
| I-145 | CH$_3$ | H | R3-94 | R4-1 | NH | Y-1 | |
| I-146 | CH$_3$ | H | R3-95 | R4-1 | NH | Y-1 | |
| I-147 | CH$_3$ | H | R3-96 | R4-1 | NH | Y-1 | |
| I-148 | CH$_3$ | H | R3-97 | R4-1 | NH | Y-1 | |
| I-149 | CH$_3$ | H | R3-98 | R4-1 | NH | Y-1 | |
| I-150 | CH$_3$ | H | R3-99 | R4-1 | NH | Y-1 | |
| I-151 | CH$_3$ | H | R3-100 | R4-1 | NH | Y-1 | |
| I-152 | CH$_3$ | H | R3-101 | R4-1 | NH | Y-1 | |
| I-153 | CH$_3$ | H | R3-102 | R4-1 | NH | Y-1 | |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-154 | CH$_3$ | H | R3-103 | R4-1 | NH | Y-1 | |
| I-155 | CH$_3$ | H | R3-104 | R4-1 | NH | Y-1 | |
| I-156 | CH$_3$ | H | R3-105 | R4-1 | NH | Y-1 | |
| I-157 | CH$_3$ | H | R3-106 | R4-1 | NH | Y-1 | |
| I-158 | CH$_3$ | H | R3-107 | R4-1 | NH | Y-1 | |
| I-159 | CH$_3$ | H | R3-108 | R4-1 | NH | Y-1 | |
| I-160 | CH$_3$ | H | R3-109 | R4-1 | NH | Y-1 | |
| I-161 | CH$_3$ | H | R3-110 | R4-1 | NH | Y-1 | |
| I-162 | CH$_3$ | H | R3-111 | R4-1 | NH | Y-1 | |
| I-163 | CH$_3$ | H | R3-112 | R4-1 | NH | Y-1 | |
| I-164 | CH$_3$ | H | R3-113 | R4-1 | NH | Y-1 | |
| I-165 | CH$_3$ | H | R3-114 | R4-1 | NH | Y-1 | |
| I-166 | CH$_3$ | H | R3-115 | R4-1 | NH | Y-1 | |
| I-167 | CH$_3$ | H | R3-116 | R4-1 | NH | Y-1 | |
| I-168 | CH$_3$ | H | R3-117 | R4-1 | NH | Y-1 | |
| I-169 | CH$_3$ | H | R3-118 | R4-1 | NH | Y-4 | |
| I-170 | CH$_3$ | H | R3-119 | R4-1 | NH | Y-4 | |
| I-171 | CH$_3$ | H | R3-120 | R4-1 | NH | Y-4 | |
| I-172 | CH$_3$ | H | R3-121 | R4-1 | NH | Y-4 | |
| I-173 | CH$_3$ | H | R3-122 | R4-1 | NH | Y-4 | |
| I-174 | CH$_3$ | H | R3-123 | R4-1 | NH | Y-4 | |
| I-175 | CH$_3$ | H | R3-124 | R4-1 | NH | Y-4 | |
| I-176 | CH$_3$ | H | R3-125 | R4-1 | NH | Y-4 | |
| I-177 | CH$_3$ | H | R3-126 | R4-1 | NH | Y-1 | |
| I-178 | CH$_3$ | OCH$_3$ | R3-1 | R4-4, R$^5$ = OCH$_3$ | O | Y-1 | |
| I-179 | CH$_3$ | OCH$_3$ | R3-1 | R4-4, R$^5$ = OCH$_3$ | O | Y-1 | |
| I-180 | CH$_3$ | OCH$_3$ | R3-1 | R4-4, R$^5$ = OCH$_3$ | O | Y-1 | |
| I-181 | CH$_3$ | H | R3-1 | R4-4, R$^5$ = OCH$_3$ | O | Y-1 | |
| I-182 | CH$_3$ | H | R3-1 | R4-1 | NH | Y-1 | |
| I-183 | CH$_3$ | H | R3-1 | R4-1 | O | Y-1 | |
| I-184 | CH$_3$ | H | R3-1 | R4-2 | NH | Y-1 | |
| I-185 | CH$_3$ | H | R3-1 | R4-2 | O | Y-1 | |
| I-186 | CH$_3$ | H | R3-127 | R4-1 | O | Y-1 | 79-81° C. |
| I-187 | CH$_3$ | H | R3-127 | R4-1 | NH | Y-1 | δ = 1.95 (s); 2.12 (s); 2.18 (s); 2.87 (d); 3.97 (s); 3.98 (s); 4.35 (m); 5.90 (m); 6.65 (br); 7.35 (d); 7.43 (s) |
| I-188 | C$_2$H$_5$ | H | R3-1 | R4-1 | O | Y-1 | δ = 1.05 (m); 2.30 (m); 3.85 (s); 4.05 (s); 4.62 (m); 5.90 (m); 7.35 (m); 7.52 (m); 7.70 (d) |
| I-189 | CH$_3$ | H | R3-127 | R4-4, R$^5$ = CH$_3$ | O | Y-1 | δ = 1.90 (s); 2.22 (s); 2.24 (s); 3.02 (s); 3.70 (s); 3.98 (s); 4.48 (m); 5.57 (m); 6.75 (m); 7.40 (m); 7.45 (s) |
| I-190 | CH$_3$ | H | R3-66 | R4-1 | O | Y-1 | δ = 1.95 (s); 2.10 (s); 2.13 (s); 2.30 (s); 3.85 (s); 3.92 (s); 4.05 (s); 4.35 (m); 5.87 (m); 6.53 (s); 6.97 (s) |
| I-191 | CH$_3$ | H | R3-128 | R4-1 | O | Y-1 | δ = 1.30 (t); 1.95 (s); 2.20 (s); 2.22 (s); 3.85 (s); 4.06 (s); 4.20 (q); 4.37 (m); 5.87 (m); 6.71 (d); 7.37 (m); 7.45 (s) |
| I-192 | CH$_3$ | H | R3-128 | R4-1 | NH | Y-1 | δ = 1.30 (t); 1.95 (8); 2.20 (s); 2.21 (s); 2.92 (d); 3.95 (s); 4.22 (m); 4.37 (m); 5.90 (m); 6.65 (br); 6.73 (m); 7.37 (m); 7.45 (s) |
| I-193 | CH$_3$ | H | R3-68 | R4-1 | NH | Y-1 | δ = 1.32 (t); 1.95 (s); 2.16 (s); 2.17 (s); 2.32 (s); 2.92 (d); 3.97 (s); 4.20 (q); 4.33 (m); 5.90 (m); 6.57 (s); 6.65 (br); 7.97 (s) |
| I-194 | CH$_3$ | H | R3-5 | R4-1 | O | Y-1 | δ = 1.95 (s); 3.85 (s); 4.05 (s); 4.53 (m); 5.87 (d); 5.93 (m); 7.07 (m); 7.25 (m); 7.55 (m); 7.63 (d) |
| I-195 | CH$_3$ | H | R3-6 | R4-1 | O | Y-1 | δ = 1.95 (s); 3.85 (s); 4.05 (s); 4.55 (m); 5.88 (d); 5.93 (m); 7.33 (m); 7.48 (s); 7.53 (d); 7.70 (d) |
| I-196 | CH$_3$ | H | R3-2 | R4-1 | O | Y-1 | δ = 1.95 (s); 3.85 (s); 4.07 (s); 4.55 (m); 5.87 (d); 5.92 (m); 6.95 (m); 7.73 (d); 7.80 (m) |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-197 | CH$_3$ | H | R3-4 | R4-1 | O | Y-1 | δ = 1.95 (s); 2.37 (s); 3.85 (s); 4.07 (s); 4.55 (m); 5.85 (d); 5.92 (m); 7.12 (m); 7.28 (m); 7.43 (d); 7.67 (d) |
| I-198 | CH$_3$ | H | R3-22 | R4-1 | O | Y-1 | δ = 1.95 (s); 2.35 (s); 3.85 (s); 4.05 (s); 4.57 (m); 5.83 (d); 5.93 (m); 7.20 (d); 7.47 (d); 7.66 (d) |
| I-199 | CH$_3$ | H | R3-24 | R4-1 | O | Y-1 | δ = 1.95 (s); 3.85 (s); 4.07 (s); 4.60 (m); 5.95 (m); 7.67 (m); 7.77 (d) |
| I-200 | CH$_3$ | H | R3-22 | R4-1 | O | Y-1 | δ = 1.25 (m); 1.95 (s); 2.65 (m); 3.85 (s); 4.05 (s); 4.58 (m); 5.83 (d); 5.93 (m); 7.25 (m); 7.48 (m); 7.67 (d |
| I-201 | CH$_3$ | H | R3-19 | R4-1 | O | Y-1 | δ = 1.95 (s); 3.85 (s); 4.07 (s); 4.58 (m); 5.87 (d); 5.93 (m); 7.15 (m); 7.30 (m); 7.45 (m); 7.63 (s); 7.70 (d) |
| I-202 | CH$_3$ | H | R3-7 | R4-1 | O | Y-1 | δ = 1.95 (s); 3.85 (s); 4.07 (s); 4.58 (m); 5.90 (d); 5.95 (m); 7.45 (m); 7.67 (d); 7.73 (d) |
| I-203 | CH$_3$ | H | R3-129 | R4-1 | O | Y-1 | δ = 1.35 (d); 1.95 (s); 3.85 (s); 4.07 (s); 4.55 (m); 5.84 (d); 5.93 (m); 6.92 (m); 7.45 (m); 7.60 (d) |
| I-204 | CH$_3$ | H | R3-11 | R4-1 | O | Y-1 | δ = 1.95 (s); 2.27 (s); 2.32 (s); 3.85 (s); 4.07 (s); 4.58 (m); 5.85 (d); 5.95 (m); 7.15 (d); 7.30 (m); 7.37 (s); 7.66 (d) |
| I-205 | CH$_3$ | H | R3-3 | R4-1 | O | Y-1 | δ = 1.95(s); 2.25 (s); 3.83 (s); 4.05 (s); 4.54 (m); 5.82 (d); 5.92 (m); 6.95 (m); 7.25 (d); 7.32 (d) |
| I-206 | CH$_3$ | H | R3-9 | R4-1 | O | Y-1 | δ = 1.93 (s); 2.31 (s); 3.85 (s); 4.07 (s); 4.56 (m); 5.85 (m); 5.95 (m); 7.03 (m); 7.33 (m); 7.43 (m); 7.64 (m). |
| I-207 | CH$_3$ | H | R3-18 | R4-1 | O | Y-1 | δ = 1.95 (s); 3.85 (s); 4.07 (s); 4.58 (m); 5.85 (d); 5.95 (m); 7.05 (m); 7.33 (m); 7.55 (d); 7.65 (d) |
| I-208 | CH$_3$ | H | R3-129 | R4-1 | NH | Y-1 | δ = 1.33 (d); 1.95 (8); 2.87 (d); 3.97 (s); 4.55 (m); 5.84 (m); 5.95 (m); 6.73 (br); 6.92 (d); 7.45 (d); 7.62 (m) |
| I-209 | CH$_3$ | H | R3-58 | R4-1 | O | Y-1 | δ = 1.95 (s); 3.83 (s); 4.05 (s); 4.65 (m); 5.95 (m); 7.43 (d); 7.55 (d); 8.23 (s) |
| I-210 | Cl | CH$_3$ | R3-1 | R4-1 | NH | Y-1 | δ = 2.10 (s); 2.65 (d); 4.01 (s); 4.95 (s); 5.97 (d); 6.85 (br); 7.37 (d); 7.50 (d); 7.67 (d) |
| I-211 | phenyl ring* | | R3-1 | R4-7 R$^6$ = CH$_3$ | | Y-1 | 90° C. |
| I-212 | phenyl ring* | | R3-98 | R4-7 R$^6$ = CH$_3$ | | Y-1 | 151° C. |
| I-213 | phenyl ring* | | R3-130 | R4-7 R$^6$ = CH$_3$ | | Y-4 | |
| I-214 | phenyl ring* | | R3-131 | R4-7 R$^6$ = CH$_3$ | | Y-4 | 139-142° C. |
| I-215 | phenyl ring* | | R3-132 | R4-7 R$^6$ = CH$_3$ | | Y-4 | 58-63° C. |
| I-216 | phenyl ring* | | R3-133 | R4-7 R$^6$ = CH$_3$ | | Y-1 | 111-113° C. |
| I-217 | phenyl ring* | | R3-65 | R4-7 R$^6$ = CH$_3$ | | Y-1 | 78-88° C. |
| I-218 | phenyl ring* | | R3-60 | R4-7 R$^6$ = CH$_3$ | | Y-1 | 83-88° C. |
| I-219 | phenyl ring* | | R3-67 | R4-7 R$^6$ = CH$_3$ | | Y-1 | 87-89° C. |
| I-220 | phenyl ring* | | R3-62 | R4-7 R$^6$ = CH$_3$ | | Y-1 | 82-88° C. |
| I-221 | phenyl ring* | | R3-134 | R4-7 R$^6$ = CH$_3$ | | Y-1 | 92-98° C. |
| I-222 | phenyl ring* | | R3-135 | R4-7 R$^6$ = CH$_3$ | | Y-1 | 141-145° C. |
| I-223 | phenyl ring* | | R3-64 | R4-7 R$^6$ = CH$_3$ | | Y-1 | 88-91° C. |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-224 | | phenyl ring* | R3-59 | R4-7<br>R$^6$ = CH$_3$ | | Y-1 | 82-86° C. |
| I-225 | | phenyl ring* | R3-63 | R4-7<br>R$^6$ = CH$_3$ | | Y-1 | 64-70° C. |
| I-226 | | phenyl ring* | R3-136 | R4-7<br>R$^6$ = CH$_3$ | | Y-1 | 101-108° C. |
| I-227 | | phenyl ring* | R3-137 | R4-7<br>R$^6$ = CH$_3$ | | Y-1 | 98-102° C. |
| I-228 | | phenyl ring* | R3-138 | R4-7<br>R$^6$ = CH$_3$ | | Y-1 | 71-75° C. |
| I-229 | | phenyl ring* | R3-139 | R4-7<br>R$^6$ = CH$_3$ | | Y-7 | 72-74° C. |
| I-230 | | phenyl ring* | R3-140 | R4-7<br>R$^6$ = CH$_3$ | | Y-7 | δ = 1.65 (s); 3.32 (s); 3.67 (s); 5.20 (s); 7.07 (m); 7.27 (m); 7.47 (m) |
| I-231 | | phenyl ring* | R3-141 | R4-7<br>R$^6$ = CH$_3$ | | Y-1 | 136-138° C. |
| I-232 | | phenyl ring* | R3-142 | R4-7<br>R$^6$ = CH$_3$ | | Y-7 | δ = 1.65 (s); 3.43 (s); 3.70 (s); 5.20 (s); 7.30-7.65 (m) |
| I-233 | | phenyl ring* | R3-127 | R4-7<br>R$^6$ = CH$_3$ | | Y-1 | R$_t$ = 3.678 min |
| I-234 | | phenyl ring* | R3-143 | R4-7<br>R$^6$ = CH$_3$ | | Y-1 | Rt = 4.092 min |
| I-235 | | phenyl ring* | R3-144 | R4-7<br>R$^6$ = CH$_3$ | | Y-1 | R$_t$ = 4.065 min |
| I-236 | | phenyl ring* | R3-145 | R4-7<br>R$^6$ = CH$_3$ | | Y-1 | R$_t$ = 3.947 min |
| I-237 | | phenyl ring* | R3-146 | R4-7<br>R$^6$ = CH$_3$ | | Y-1 | R$_t$ = 3.875 min |
| I-238 | | phenyl ring* | R3-147 | R4-7<br>R$^6$ = CH$_3$ | | Y-1 | R$_t$ = 4.100 min |
| I-239 | | phenyl ring* | R3-68 | R4-7<br>R$^6$ = CH$_3$ | | Y-1 | R$_t$ = 3.933 min |
| I-240 | | phenyl ring* | R3-148 | R4-7<br>R$^6$ = CH$_3$ | | Y-4 | R$_t$ = 3.496 min |
| I-241 | | phenyl ring* | R3-149 | R4-7<br>R$^6$ = CH$_3$ | | Y-4 | R$_t$ = 4.075 min |
| I-242 | | phenyl ring* | R3-150 | R4-7<br>R$^6$ = CH$_3$ | | Y-1 | R$_t$ = 4.128 min |
| I-243 | | phenyl ring* | R3-151 | R4-7<br>R$^6$ = CH$_3$ | | Y-1 | R$_t$ = 3.894 min |
| I-244 | | phenyl ring* | R3-152 | R4-7<br>R$^6$ = CH$_3$ | | Y-1 | R$_t$ = 3.875 min |
| I-245 | | phenyl ring* | R3-153 | R4-7<br>R$^6$ = CH$_3$ | | Y-1 | R$_t$ = 3.995 min |
| I-246 | | phenyl ring* | R3-154 | R4-7<br>R$^6$ = CH$_3$ | | Y-1 | R$_t$ = 4.115 min |
| I-247 | | phenyl ring* | R3-20 | R4-7<br>R$^6$ = CH$_3$ | | Y-1 | R$_t$ = 3.715 min |
| I-248 | | phenyl ring* | R3-157 | R4-7<br>R$^6$ = CH$_3$ | | Y-1 | R$_t$ = 3.714 min |
| I-249 | | phenyl ring* | R3-128 | R4-7<br>R$^6$ = CH$_3$ | | Y-1 | R$_t$ = 3.861 min |
| I-250 | | phenyl ring* | R3-158 | R4-7<br>R$^6$ = CH$_3$ | | Y-1 | R$_t$ = 4.251 min |
| I-251 | | phenyl ring* | R3-159 | R4-7<br>R$^6$ = CH$_3$ | | Y-1 | 105-107° C. |
| I-252 | | phenyl ring* | R3-151 | R4-7<br>R$^6$ = Ethyl | | Y-1 | 102-104° C. |
| I-253 | | phenyl ring* | R3-1 | R4-7<br>R$^6$ = CHF$_2$ | | Y-1 | 96-97° C. |
| I-254 | | phenyl ring* | R3-128 | R4-7<br>R$^6$ = Ethyl | | Y-1 | Rt = 4.219 min |
| I-255 | | phenyl ring* | R3-68 | R4-7<br>R$^6$ = Ethyl | | Y-1 | Rt = 4.239 min |
| I-256 | | phenyl ring* | R3-146 | R4-7<br>R$^6$ = Ethyl | | Y-1 | R$_t$ = 4.176 min |
| I-257 | | phenyl ring* | R3-66 | R4-7<br>R$^6$ = Ethyl | | Y-1 | R$_t$ = 4.013 min |
| I-258 | | phenyl ring* | R3-160 | R4-7<br>R$^6$ = CH$_3$ | | Y-1 | δ = 2.15 (s); 3.67 (s); 3.95 (s); 5.28 (s); 6.85 (m); 7.45 (m); 7.50 (m); 7.70 (m) |
| I-259 | | phenyl ring* | R3-161 | R4-7<br>R$^6$ = CH$_3$ | | Y-1 | δ = 1.33 (t); 2.17 (s); 3.68 (s); 4.22 (q); 5.28 (s); 6.87 (d); 7.45 (m); 7.52 (m); 7.73 (m) |

TABLE I-continued

Compounds of formula I with physical data (melting point [° C.]; $^1$H-NMR (CDCl$_3$) (δ); HPLC/MS retention time [min])

| No. | R$^1$ | R$^2$ | R$^3$ | R$^4$ | X | Y | m.p. [° C.]; $^1$H-NMR (δ); R$_t$ [min] |
|---|---|---|---|---|---|---|---|
| I-260 | phenyl ring* | | R3-162 | R4-7 R$^6$ = CH$_3$ | | Y-1 | R$_t$ = 3.924 min |
| I-261 | phenyl ring* | | R3-163 | R4-7 R$^6$ = CH$_3$ | | Y-1 | R$_t$ = 4.131 min |
| I-262 | phenyl ring* | | R3-164 | R4-7 R$^6$ = CH$_3$ | | Y-1 | R$_t$ = 4.141 min |
| I-263 | phenyl ring* | | R3-165 | R4-7 R$^6$ = CH$_3$ | | Y-1 | R$_t$ = 3.916 min |
| I-264 | phenyl ring* | | R3-166 | R4-7 R$^6$ = CH$_3$ | | Y-1 | R$_t$ = 4.220 min |
| I-265 | phenyl ring* | | R3-167 | R4-7 R$^6$ = CH$_3$ | | Y-1 | R$_t$ = 4.050 min |
| I-266 | phenyl ring* | | R3-149 | R4-7 R$^6$ = CH$_3$ | | Y-8 | δ = 2.03 (s); 3.71 (s); 7.45-7.62 (m) |
| I-267 | phenyl ring* | | R3-168 | R4-7 R$^6$ = CH$_3$ | | Y-1 | δ = 2.20 (s); 2.40 (s); 3.69 (s); 5.20 (s); 6.70 (s); 7.12 (s); 7.42 (s); 7.53 (m); 7.72 (m); 7.91 (s) |
| I-268 | phenyl ring* | | R3-169 | R4-7 R$^6$ = CH$_3$ | | Y-1 | δ = 2.11 (s); 2.18 (s); 3.62 (s); 3.72 (s); 5.21 (s); 6.77 (s); 6.96 (s); 7.25 (s); 7.53 (m); 7.72 (m); 8.91 (s) |
| I-269 | phenyl ring* | | R3-170 | R4-7 R$^6$ = CH$_3$ | | Y-1 | δ = 2.00 (s); 2.05 (s); 2.16 (s); 2.21 (s); 3.70 (s); 5.16 (s); 6.72 (s); 6.82 (s); 7.50 (m); 7.74 (m) |
| I-270 | phenyl ring* | | R3-171 | R4-7 R$^6$ = CH$_3$ | | Y-1 | δ = 2.16 (s); 2.39 (s); 2.53 (s); 3.70 (s); 5.19 (s); 6.70 (s); 7.53 (m); 7.72 (m) |
| I-271 | phenyl ring* | | R3-172 | R4-7 R$^6$ = CH$_3$ | | Y-1 | δ = 2.18 (s); 2.29 (s); 3.70 (s); 5.18 (s); 6.71 (s); 7.06 (s); 7.50 (m); 7.71 (m); 8.38 (s); 8.44 (s) |
| I-272 | phenyl ring* | | R3-173 | R4-7 R$^6$ = CH$_3$ | | Y-1 | δ = 1.28 (m); 2.12 (s); 3.00 (broad); 3.58 (m); 3.69 (m); 5.52 (s); 6.28 (s); 7.45 (m); 7.72 (m) |
| I-273 | phenyl ring* | | R3-174 | R4-7 R$^6$ = CH$_3$ | | Y-1 | δ = 0.97 (m); 1.02 (m); 1.20 (m); 1.90 (m); 2.05 (s); 2.62 (m); 3.68 (s); 5.51 (s); 5.84 (m); 7.50 (m); 7.73 (m) |
| I-274 | phenyl ring* | | R3-175 | R4-7 R$^6$ = CH$_3$ | | Y-8 | R$_t$ = 3.715 min |
| I-275 | CH$_3$ | H | R3-20 | R4-1 | O | Y-1 | δ = 1.95 (s); 3.85 (s); 4.07 (s); 4.58 (m); 5.92 (m); 7.45 (m); 7.52 (m); 7.75 (m); 7.84 (d) |
| I-276 | CH$_3$ | H | R3-12 | R4-1 | O | Y-1 | 72-74° C. |
| I-277 | CH$_3$ | H | R3-15 | R4-1 | O | Y-1 | 73-75° C. |
| I-278 | CH$_3$ | H | R3-176 | R4-1 | O | Y-1 | δ = 1.97 (s); 3.85 (s); 4.07 (s); 4.58 (d); 5.90 (d); 5.95 (d); 7.17 (t); 7.43 (m); 7.65 (m) |
| I-279 | CH$_3$ | H | R3-98 | R4-1 | O | Y-1 | 90-92° C. |
| I-280 | CH$_3$ | H | R3-20 | R4-1 | NH | Y-1 | 101-103° C. |
| I-281 | CH$_3$ | H | R3-12 | R4-1 | NH | Y-1 | 112-115° C. |
| I-282 | CH$_3$ | H | R3-15 | R4-1 | NH | Y-1 | 93-95° C. |
| I-283 | CH$_3$ | H | R3-176 | R4-1 | NH | Y-1 | 84-86° C. |
| I-284 | CH$_3$ | H | R3-98 | R4-1 | NH | Y-1 | δ = 1.95 (s); 2.27 (s); 2.93 (d); 3.97 (s); 4.48 (m); 5.93 (m); 6.42 (m); 6.67 (broad); 6.80 (d); 7.37 (d); 7.45 (m); 7.68 (m); 7.83 (m) |
| I-285 | CH$_3$ | H | R3-1 | R4-4, R$^5$ = OCH$_3$ | O | Y-1 | δ = 1.93 (s); 3.72 (s); 3.81 (s); 4.78 (d); 5.73 (t); 5.90 (d); 7.36 (d); 7.55 (d); 7.70 (d) |
| I-286 | CH$_3$ | H | R3-51 | R4-1 | O | Y-1 | δ = 1.93 (s); 2.45 (s); 3.82 (s); 4.05 (s); 4.60 (d); 5.92 (t); 7.25-7.50 (m) |
| I-287 | C$_2$H$_5$ | H | R3-1 | R4-1 | NH | Y-1 | δ = 1.05 (t); 2.30 (q); 2.90 (d); 3.97 (s); 4.58 (m); 5.93 (m); 6.70 (broad); 7.35 (m); 7.53 (m); 7.68 (s) |
| I-288 | CH$_3$ | H | R3-58 | R4-1 | NH | Y-1 | δ = 1.95 (s); 2.90 (d); 3.97 (s); 4.63 (m); 5.95 (m); 6.75 (broad); 7.43 (m); 7.55 (m); 8.23 (s) |
| I-289 | CH$_3$ | H | R3-51 | R4-1 | NH | Y-1 | δ = 1.93 (s); 2.45 (s); 2.83 (d); 3.95 (s); 4.58 (m); 5.92 (m); 6.73 (broad); 7.30-7.50 (m) |

TABLE I-continued

Compounds of formula I with physical data (melting point [° C.]; $^1$H-NMR (CDCl$_3$) ($\delta$); HPLC/MS retention time [min])

| No. | R$^1$ | R$^2$ | R$^3$ | R$^4$ | X | Y | m.p. [° C.]; $^1$H-NMR ($\delta$); R$_t$ [min] |
|---|---|---|---|---|---|---|---|
| I-290 | CH$_3$ | H | R3-1 | R4-4, R$^5$ = C$_2$H$_5$ | O | Y-1 | $\delta$ = 1.18 (m); 1.95 (s); 3.45 (broad); 3.73 (s); 4.67 (m); 5.70 (m); 5.90 (m); 7.35 (m); 7.53 (m); 7.67 (m) |
| I-291 | CH$_3$ | H | R3-39 | R4-1 | O | Y-1 | 72° C. |
| I-292 | CH$_3$ | H | R3-44 | R4-1 | O | Y-1 | 106-110° C. |
| I-293 | CH$_3$ | H | R3-44 | R4-1 | NH | Y-1 | 177° C. |
| I-294 | CH$_3$ | H | R3-177 | R4-1 | O | Y-1 | $\delta$ = 1.93 (s); 3.20 (m); 3.28 (m); 3.83 (s); 3.90 (m); 4.05 (s); 4.42 (m); 4.50 (m); 5.88 (m); 5.94 (s); 6.83 (m); 7.25 (m); 7.50 (s) |
| I-295 | CH$_3$ | H | R3-39 | R4-1 | NH | Y-1 | 142° C. |
| I-296 | Iso-butyl | H | R3-1 | R4-1 | O | Y-1 | $\delta$ = 0.93 (m); 1.60 (m); 2.15 (d); 3.84 (s); 4.07 (s); 4.62 (m); 5.89 (m); 7.35 (d); 7.53 (d); 7.67 (s) |
| I-297 | CH$_3$ | H | R3-29 | R4-1 | O | Y-1 | $\delta$ = 1.95 (s); 3.85 (s); 4.07 (s); 4.65 (m); 5.95 (m); 7.27 (m); 7.87 (m); 8.35 (s) |
| I-298 | CH$_3$ | H | R3-36 | R4-1 | O | Y-1 | $\delta$ = 1.95 (s); 3.85 (s); 4.07 (s); 4.65 (m); 5.95 (m); 7.63 (m); 7.67 (m); 7.93 (m); 8.37 (s) |
| I-299 | Iso-butyl | H | R3-1 | R4-1 | NH | Y-1 | 177° C. |
| I-300 | C$_2$H$_5$ | H | R3-58 | R4-1 | O | Y-1 | 87° C. |
| I-301 | CH$_3$ | H | R3-29 | R4-1 | NH | Y-1 | 140° C. |
| I-302 | CH$_3$ | H | R3-36 | R4-1 | NH | Y-1 | 125° C. |
| I-303 | CH$_3$ | H | R3-33 | R4-1 | O | Y-1 | $\delta$ = 1.95 (s); 3.83 (s); 4.05 (s); 4.65 (m); 5.95 (m); 7.37 (m); 7.57 (m); 8.27 (s) |
| I-304 | CH$_3$ | H | R3-54 | R4-1 | O | Y-1 | $\delta$ = 1.25 (m); 1.95 (s); 2.68 (m); 3.83 (s); 4.05 (s); 4.65 (m); 5.95 (m); 7.30 (m); 7.51 (m); 8.20 (s) |
| I-305 | CH$_3$ | H | R3-33 | R4-1 | NH | Y-1 | 126° C. |
| I-306 | CH$_3$ | H | R3-54 | R4-1 | NH | Y-1 | 128° C. |
| I-307 | CH$_3$ | H | R3-178 | R4-1 | O | Y-1 | $\delta$ = 1.95 (s); 2.27 (s); 3.82 (s); 4.07 (s); 4.62 (m); 5.95 (m); 7.28 (m); 7.36 (m); 7.93 (s) |
| I-308 | CH$_3$ | H | R3-130 | R4-1 | O | Y-4 | $\delta$ = 1.95 (s); 2.25 (s); 3.80 (s); 4.05 (s); 4.55 (m); 5.90 (m); 7.25-7.60 (m); 7.77 (m); 7.85 (s); 8.05 (s); 8.27 (s) |
| I-309 | CH$_3$ | H | R3-130 | R4-1 | NH | —CH=N—O—CH$_2$— | $\delta$ = 1.95 (s); 2.88 (d); 3.96 (s); 4.50 (m); 5.92 (m); 6.70 (broad); 7.25-7.60 (m); 7.76 (m); 8.05 (s); 8.08 (s); 8.27 (s) |
| I-310 | CH$_3$ | H | R3-42 | R4-1 | O | Y-1 | 116° C. |
| I-311 | C$_2$H$_5$ | H | R3-58 | R4-1 | NH | Y-1 | 154° C. |
| I-312 | CH$_3$ | H | R3-30 | R4-1 | NH | Y-1 | 167° C. |
| I-313 | CH$_3$ | H | R3-178 | R4-1 | NH | Y-1 | 143° C. |
| I-314 | CH$_3$ | H | R3-42 | R4-1 | NH | Y-1 | 147° C. |
| I-315 | CH$_3$ | H | R3-40 | R4-1 | NH | Y-1 | 153° C. |
| I-316 | CH$_3$ | H | R3-177 | R4-1 | NH | Y-1 | $\delta$ = 1.93 (s); 2.88 (d); 3.20 (m); 3.28 (m); 3.90 (m); 3.95 (s); 4.42 (m); 4.50 (m); 5.90 (m); 5.95 (m); 6.67 (broad); 6.86 (m); 7.25 (m); 7.50 (s) |
| I-317 | CH$_3$ | H | R3-179 | R4-1 | NH | Y-1 | $\delta$ = 1.83 (s); 1.93 (s); 2.18 (s); 2.42 (m); 2.70 (m); 2.88 (d); 3.83 (s); 3.95 (s); 4.35 (m); 5.90 (m); 6.65 (m); 6.93 (m) |
| I-318 | CH$_3$ | H | R3-38 | R4-1 | O | Y-1 | 87° C. |
| I-319 | CH$_3$ | H | R3-32 | R4-1 | O | Y-1 | $\delta$ = 1.93 (s); 2.27 (s); 3.80 (s); 4.05 (s); 4.62 (m); 5.95 (m); 7.30 (m); 7.93 (s) |
| I-320 | CH$_3$ | H | R3-34 | R4-1 | NH | Y-1 | 120° C. |
| I-321 | CH$_3$ | H | R3-38 | R4-1 | NH | Y-1 | 143° C. |
| I-322 | CH$_3$ | H | R3-37 | R4-1 | NH | Y-1 | 117° C. |
| I-323 | CH$_3$ | H | R3-40 | R4-1 | O | Y-1 | 118° C. |
| I-324 | CH$_3$ | H | R3-37 | R4-1 | O | Y-1 | $\delta$ = 1.93 (s); 2.23 (s); 2.35 (s); 3.80 (s); 4.05 (s); 4.62 (m); 5.95 (m); 7.15 (m); 7.91 (s) |
| I-325 | CH$_3$ | H | R3-43 | R4-1 | NH | Y-1 | 136° C. |
| I-326 | CH$_3$ | H | R3-34 | R4-1 | O | Y-1 | $\delta$ = 1.95 (s); 3.83 (s); 4.05 (s); 4.63 (m); 5.95 (m); 7.67 (m); 7.82 (m); 8.42 (s) |

TABLE I-continued

Compounds of formula I with physical data (melting point [° C.]; ¹H-NMR (CDCl₃) (δ); HPLC/MS retention time [min])

| No. | R¹ | R² | R³ | R⁴ | X | Y | m.p. [° C.]; ¹H-NMR (δ); R_t [min] |
|---|---|---|---|---|---|---|---|
| I-327 | CH₃ | H | R3-32 | R4-1 | NH | Y-1 | δ = 2.07 (s); 2.42 (s); 2.92 (d); 4.08 (s); 4.78 (m); 6.08 (m); 6.93 (broad); 7.45 (m); 8.08 (s) |
| I-328 | CH₃ | H | R3-41 | R4-1 | NH | Y-1 | δ = 1.95 (s); 2.90 (d); 3.95 (s); 4.65 (m); 5.93 (m); 6.73 (broad); 7.30 (m); 7.55 (m); 8.23 (s) |
| I-329 | CH₃ | H | R3-28 | R4-1 | NH | Y-1 | 94° C. |
| I-330 | CH₃ | H | R3-50 | R4-1 | NH | Y-1 | 130° C. |
| I-331 | CH₃ | H | R3-41 | R4-1 | O | Y-1 | δ = 1.95 (s); 3.87 (s); 4.06 (s); 4.63 (m); 5.93 (m); 7.32 (m); 7.55 (m); 8.23 (s) |
| I-332 | C₂H₅ | H | R3-2 | R4-1 | O | Y-1 | δ = 1.05 (t); 2.30 (m); 3.82 (s); 4.05 (s); 4.62 (d); 5.90 (m); 6.93 (m); 7.73 (m); 7.80 (m) |
| I-333 | CH₃ | H | R3-180 | R4-1 | O | Y-1 | δ = 1.95 (s); 2.27 (s); 3.85 (s); 4.07 (s); 4.40 (m); 5.88 (m); 6.66 (d); 6.78 (m); 7.37 (m); 7.45 (m); 7.83 (d) |
| I-334 | CH₃ | H | R3-77 | R4-1 | O | Y-1 | 123-124° C. |
| I-335 | CH₃ | H | R3-119 | R4-1 | O | Y-4 | δ = 1.90 (s); 2.12 (s); 3.83 (s); 3.92 (s); 4.03 (s); 4.33 (s); 5.74 (m); 7.18-7.45 (m) |
| I-336 | CH₃ | H | R3-80 | R4-1 | O | Y-1 | 133-134° C. |
| I-337 | CH₃ | H | R3-180 | R4-1 | NH | Y-1 | δ = 1.95 (s); 2.27 (s); 2.90 (d); 3.97 (s); 4.40 (m); 5.88 (m); 6.66 (broad); 6.82 (m); 7.37 (m); 7.45 (m); 7.81 (d) |
| I-338 | CH₃ | H | R3-79 | R4-1 | O | Y-1 | 94-97° C. |
| I-339 | CH₃ | H | R3-119 | R4-1 | NH | Y-4 | δ = 1.90 (s); 2.12 (s); 2.85 (d); 3.92 (s); 4.33 (m); 5.75 (m); 6.60 (broad); 7.18-7.45 (m) |
| I-340 | CH₃ | H | R3-130 | R4-1 | O | —CH=N—O—CH₂— | δ = 1.95 (s); 3.82 (s); 4.05 (s); 4.52 (m); 5.87 (m); 7.25-7.60 (m); 7.75 (m); 7.80 (s); 8.05 (s); 8.26 (s) |
| I-341 | CH₃ | H | R3-130 | R4-1 | NH | Y-4 | δ = 1.95 (s); 2.25 (s); 2.83 (d); 3.97 (s); 4.54 (m); 5.93 (m); 6.75 (broad); 7.25-7.60 (m); 7.77 (m); 7.82 (s); 8.02 (s); 8.29 (s) |
| I-342 | CH₃ | H | R3-181 | R4-1 | NH | Y-1 | δ = 1.95 (s); 2.27 (s); 2.88 (d); 3.97 (s); 4.39 (m); 5.93 (m); 6.67 (broad); 6.80 (m); 7.08 (m); 7.27 (m); 7.45 (m) |
| I-343 | CH₃ | H | R3-182 | R4-1 | NH | Y-1 | δ = 1.95 (s); 2.27 (s); 2.91 (d); 3.98 (s); 4.41 (m); 5.93 (m); 6.70 (broad); 6.85 (m); 7.37 (m); 7.65 (m) |
| I-344 | CH₃ | H | R3-183 | R4-1 | NH | Y-1 | δ = 1.95 (s); 2.25 (s); 2.91 (d); 3.98 (s); 4.40 (m); 5.93 (m); 6.66 (broad); 6.83 (m); 7.25-7.46 (m) |
| I-345 | CH₃ | H | R3-184 | R4-1 | NH | Y-1 | δ = 1.95 (s); 2.25 (s); 2.90 (d); 3.85 (s); 3.98 (s); 4.38 (m); 5.93 (m); 6.66 (broad); 6.82 (m); 7.30 (m) |
| I-346 | CH₃ | H | R3-185 | R4-1 | NH | Y-1 | δ = 1.95 (s); 2.20 (s); 2.88 (d); 3.95 (s); 4.30 (m); 4.98 (s); 5.92 (m); 6.65 (m); 6.80 (m); 7.40 (m) |
| I-347 | CH₃ | H | R3-69 | R4-1 | NH | Y-1 | δ = 1.95 (s); 2.90 (d); 3.95 (s); 4.65 (m); 5.92 (m); 6.67 (broad); 6.87 (m); 7.25 (m); 7.67 (m) |
| I-348 | CH₃ | H | R3-186 | R4-1 | NH | Y-1 | δ = 1.42 (m); 1.95 (s); 2.27 (s); 2.91 (d); 2.96 (m); 3.98 (s); 4.42 (m); 5.93 (m); 6.70 (broad); 6.83 (m); 7.87 (m) |
| I-349 | C₂H₅ | H | R3-5 | R4-1 | NH | Y-1 | 98° C. |
| I-350 | CH₃ | H | R3-88 | R4-1 | O | Y-1 | δ = 1.95 (s); 3.53 (s); 3.85 (s); 4.05 (s); 4.50 (m); 5.65 (s); 5.90 (m); 7.28 (m); 7.50 (s) |
| I-351 | CH₃ | H | R3-88 | R4-1 | NH | Y-1 | δ = 1.95 (s); 2.90 (d); 3.50 (s); 3.97 (s); 4.48 (m); 5.65 (m); 5.93 (m); 6.70 (broad); 7.28 (m); 7.50 (s) |
| I-352 | CH₃ | H | R3-76 | R4-1 | NH | Y-1 | δ = 1.95 (s); 2.27 (s); 2.87 (d); 3.95 (s); 4.63 (m); 5.93 (m); 6.66 (broad); 7.35 (m); 7.77 (m) |

TABLE I-continued

Compounds of formula I with physical data (melting point [° C.];
$^1$H-NMR (CDCl$_3$) ($\delta$); HPLC/MS retention time [min])

| No. | R$^1$ | R$^2$ | R$^3$ | R$^4$ | X | Y | m.p. [° C.]; $^1$H-NMR ($\delta$); R$_t$ [min] |
|---|---|---|---|---|---|---|---|
| I-353 | CH$_3$ | H | R3-187 | R4-1 | NH | Y-1 | $\delta$ = 1.95 (s); 2.87 (d); 3.97 (s); 4.63 (m); 5.90 (d); 5.95 (m); 6.70 (broad); 7.48 (m); 7.85 (m); 7.97 (d) |
| I-354 | CH$_3$ | H | R3-188 | R4-1 | NH | Y-1 | $\delta$ = 1.93 (s); 2.77 (d); 3.93 (s); 4.54 (m); 5.92 (m); 6.80 (broad); 7.33 (m); 7.45 (m) |
| I-355 | CH$_3$ | H | R3-189 | R4-1 | NH | Y-1 | $\delta$ = 1.95 (s); 2.85 (d); 3.95 (s); 4.55 (m); 5.92 (m); 6.70 (broad); 7.23 (m); 7.40 (m); 7.64 (s); 7.78 (d) |
| I-356 | CH$_3$ | H | R3-193 | R4-1 | NH | Y-1 | $\delta$ = 1.94 (s); 2.87 (d); 3.94 (s); 4.44 (m); 5.17 (s); 5.67 (d); 5.88 (m); 6.70 (broad); 6.86 (m); 7.20 (m); 7.37 (d) |
| I-357 | CH$_3$ | H | R3-194 | R4-1 | NH | Y-1 | $\delta$ = 1.95 (s); 2.80 (d); 3.95 (s); 4.55 (m); 5.87 (d); 5.93 (m); 6.75 (broad); 7.25 (m); 7.35 (m); 7.45 (m); 7.55 (m); 7.70 (d) |
| I-358 | CH$_3$ | H | R3-83 | R4-1 | NH | Y-1 | $\delta$ = 1.95 (s); 2.90 (m); 3.95 (s); 4.57 (m); 5.92 (m); 6.13 (s); 6.83 (broad); 7.45 (m); 7.35 (m); 7.70 (m) |
| I-359 | CH$_3$ | H | R3-195 | R4-1 | NH | Y-1 | $\delta$ = 1.95 (s); 2.50 (s); 2.88 (d); 3.95 (s); 4.57 (m); 5.85 (d); 5.95 (m); 6.70 (broad); 6.90 (m); 7.60 (m); 8.33 (d) |

*"phenyl ring" denotes that R$^1$ and R$^2$ together with the two carbon atoms linking them form a phenyl ring. Isobutyl = 2-methyl-1-propyl.
m.p. = melting point; R$_t$ = HPLC Retention time.
HPLC-data: RP-18 column (Chromolith Speed ROD 50 × 4.6 mm from Merck KgaA, Germany), 1.8 ml/min, injection volume 2 μl, column temperature 40° C.
Eluent: Acetonitrile + 0.1% trifluoroacetic acid (TFA)/water + 0.1% TFA (gradient %: 95 to 95:5 within 5 min), 40° C. MS: Quadrupole electrospray ionisation, 80 V (pos. mode).

II. EXAMPLES OF THE ACTION AGAINST HARMFUL FUNGI

The fungicidal action of the compounds of the formula I was demonstrated by the following experiments:

II.1 Microtiter Tests

The active substances were formulated separately as a stock solution in dimethyl sulfoxide (DMSO) at a concentration of 10 000 ppm.

Use Example 1

Activity Against the *Septoria* Blotch Pathogen Caused by *Septoria tritici* in the Microtiter Test
Fungal Strains Used:
 a) *Septoria tritici* (Qo-inhibitor sensitive, wild-type)
 b) *Septoria tritici* (Qo-inhibitor-resistant, G143A mutant)
100 ml 2% Malt extract in water at pH6.8 were inoculated with microspores from 2 week old cultures grown on 2% malt extract +2% agar in Petri dishes and incubated for 3 days on a rotary shaker at 24° C. und 150 rpm. The culture was harvested, glycerol was added (15% (v/v) and kept frozen at −20° C. in aliquots of 1 ml.

1 ml stock suspension was thawed and suspended into 800 ml of 2% malt extract in water at pH 6.8. Compounds were diluted from stock solution in (dimethylsulfoxide) DMSO in 10 steps. The compound solutions were diluted 1/5 with sterile deionized water before use. 5 μl of the compound solutions were transferred into empty microplates. The plates were then filled with 195 μl of the microspore suspension of each strain.

The antifungal activity was determined by measuring the turbidity of a culture in 96-well microplates in the presence of test compounds. Fungal growth was measured by recording the optical density at 620 nm every 15 h for 150 h. The relative antifungal activity was calculated by comparison of the effect of the test compounds with the effect of a DMSO control and a standard fungicide.

IC$_{50}$-values (concentration of test compound resulting in 50% inhibition of fungal growth) were calculated from the resulting dose-response for each compound and strain. The initial concentration of the test compounds and the 10 steps of dilution (1:4 each) allowed IC$_{50}$-values from 0.001 to 100 μmol/l (μM) to be assessed.

TABLE II

| Compound | Resistant *Septoria tritici* isolate (G143A mutation) (R-IC$_{50}$) [μM] | Sensitive *Septoria tritici* isolate (wild type) (S-IC$_{50}$) [μM] | Resistance factor RF = R-IC$_{50}$/S-IC$_{50}$ |
|---|---|---|---|
| Azoxystrobin | >100 | 3.5 | n.d. |
| Dimoxystrobin | >100 | 7.1 | n.d. |
| Enestroburin | >100 | 4.5 | n.d. |
| Kresoximmethyl | >100 | 0.76 | n.d. |
| Metominostrobin | >100 | >100 | n.d. |
| Orysastrobin | >100 | 27 | n.d. |
| Picoxystrobin | >100 | 2.3 | n.d. |
| Pyrametostrobin | >100 | >100 | n.d. |
| Pyraoxystrobin | >100 | 1.6 | n.d. |
| Pyraclostrobin | 3.4 | 0.0012 | 2882 |
| Trifloxystrobin | >100 | 0.52 | n.d. |
| I-5 | 2.2 | 0.083 | 26 |
| I-6 | 8.3 | 0.34 | 24 |
| I-82 | 6.8 | 1.1 | 6 |
| I-83 | 7.6 | 1.6 | 4.6 |

TABLE II-continued

| Compound | Resistant Septoria tritici isolate (G143A mutation) (R-IC$_{50}$) [μM] | Sensitive Septoria tritici isolate (wild type) (S-IC$_{50}$) [μM] | Resistance factor RF = R-IC$_{50}$/ S-IC$_{50}$ |
|---|---|---|---|
| I-84 | 16.1 | 0.5 | 33 |
| I-85 | 22 | 0.8 | 29 |
| I-90 | 26 | 1.0 | 26 |
| I-91 | 27 | 1.6 | 17 |
| I-94 | 12 | 0.6 | 22 |
| I-95 | 29 | 2.2 | 14 |
| I-97 | 49 | 1.7 | 29 |
| I-191 | 37 | 1.3 | 29 |
| I-211 | 1.1 | 0.44 | 2.6 |
| I-212 | 8.3 | 1.4 | 6 |
| I-213 | 0.057 | 0.076 | 0.7 | resistance level, Pyraclostrobin showed insufficient control level although it has been used at commercial dose levels, whereas compound I-6 was capable to control the Qo inhibitor-resistant isolates of *Septoria tritici* with the G143 mutation.

Trial 2: Efficacy against *Septoria tritici* on winter wheat

This trial was conducted under field conditions in Limburgerhof, Rhineland-Palatinate, Germany. Seeds of winter wheat (cv. Riband) were planted and grown under standard conditions with adequate supply of water and nutrients. At growing stage GS 33 (Apr. 8, 2011), a first first compound treatment (200 g a.i per ha) was made with a water volume of 400 L/ha, which was repeated 26 days later at growing stage GS 39. No further fungicide treatments were applied. Infection with fungal pathogens (e.g. *Septoria tritici*) occurred naturally. The evaluation of the disease incidences for *Septoria tritici* 19 and 34 days after the last treatment (DAA) are shown in Table IV. In the last row, the evaluation of the percentage of Qo inhibitor-resistant *Septoria tritici* isolates with the G143A mutation after the treatments is given.

TABLE IV

| Treatment | Concentration (g a.i./ha) | Disease (%) 19 DAA | Disease (%) 34 DAA | Percentage of G143A mutation (%) in *Septoria tritici* isolates |
|---|---|---|---|---|
| Compound I-6 | 200 | 3 | 12 | 99 |
| Pyraclostrobin | 200 | 5 | 28 | 100 |
| untreated | — | 10 | 36 | 94 |

In this test, about the entire population of the fungal pathogen *Septoria tritici* has been Qo inhibitor-resistant (as evaluated at the end of the trial). Due to this high resistance level, Pyraclostrobin has shown antifungal activity only slightly above the untreated control although it has been used at commercial dose levels. However compound I-6 was capable to reduce the infection by Qo inhibitor-resistant *Septoria tritici* with the G143 mutation significantly.

B) Glass House Trials

The spray solutions were prepared in several steps:

The stock solution was prepared as follows: 1.26 ml of a 1:1 mixture of cyclohexanone and dimethylsulfoxide was added to 8.4 mg of active ingredient. Next, 40.74 ml of a mixture of water, acetone (10%), the emulsifier Wettol (0.1%) and the wetting agent Silwet (0.05%) was added. This stock solution was then further diluted with the described solvent-emulsifier-water mixture to the desired concentrations.

Trial 3: Control of Leaf Blotch on Wheat Caused by Caused by Two *Septoria tritici* Isolates Containing the G143A in the Cytochrome b Gene for their Cytochrome $bc_1$ Complex Wheat plants were grown in pots. These plants were sprayed to run-off with an aqueous suspension, containing the desired concentration of active ingredient. The next day, the treated plants were inoculated with an aqueous suspension of *Septoria tritici*. After inoculation, the trial plants were covered with a lid and immediately transferred to a chamber with a relative humidity of about 83 to 85% and 19.5 to 20° C. After 4 days the lid was removed. Altogether, the trial plants were cultivated for about 28 days in that greenhouse chamber. The extent of fungal attack on the leaves was then visually assessed as % diseased leaf area.

TABLE VII

| Treatment | Conc. (ppm) | Resistant *Septoria tritici* isolate 1 (G143A mutation) Disease level (%) | Resistant *Septoria tritici* isolate 2 (G143A mutation) Disease level (%) |
|---|---|---|---|
| I-7 | 200 | 3 | 0 |
| I-7 | 100 | 3 | 1 |
| I-7 | 50 | 20 | 5 |
| I-7 | 25 | 80 | 15 |
| I-7 | 12.5 | 100 | 90 |
| I-211 | 200 | 1 | 0 |
| I-211 | 100 | 3 | 1 |
| I-211 | 50 | 10 | 5 |
| I-211 | 25 | 60 | 10 |
| I-211 | 12.5 | 80 | 30 |
| I-14 | 200 | 3 | 1 |
| I-14 | 100 | 15 | 5 |
| I-14 | 50 | 70 | 15 |
| I-14 | 25 | 80 | 70 |
| I-14 | 12.5 | 100 | 90 |
| I-6 | 200 | 1 | 0 |
| I-6 | 100 | 3 | 3 |
| I-6 | 50 | 3 | 3 |
| I-6 | 25 | 10 | 15 |
| I-6 | 12.5 | 50 | 20 |
| I-11 | 200 | 1 | 1 |
| I-11 | 100 | 3 | 5 |
| I-11 | 50 | 30 | 30 |
| I-11 | 25 | 90 | 50 |
| I-11 | 12.5 | 100 | 70 |
| Pyraclostrobin | 200 | 30 | 15 |
| Pyraclostrobin | 100 | 90 | 25 |
| Pyraclostrobin | 50 | 100 | 40 |
| Pyraclostrobin | 25 | 100 | 60 |
| Pyraclostrobin | 12.5 | 100 | 60 |
| Trifloxystrobin | 200 | 90 | 60 |
| Trifloxystrobin | 100 | 90 | 70 |
| Trifloxystrobin | 50 | 90 | 70 |
| Trifloxystrobin | 25 | 100 | 70 |
| Trifloxystrobin | 12.5 | 100 | 80 |

III. MOLECULAR MODELING

III.1 Structural Models of Wild-Type and G143A Mutant Binding Site

Structural models of the binding site of wild-type and G143A cytochrome $bc_1$ complex were generated based on the crystallographic structure of bovine cytochrome $bc_1$ complex with azoxystrobin bound to the Qo-site (PDB: 1SQB: Esser et al. J Mol Biol 341, 281-302 (2004)).

The structure was imported into Schrödinger Maestro (version 9.0, Schrödinger, LLC, New York, N.Y., 2009).

Cytochrome b was isolated from the structure of the complex and treated with the Schrödinger Protein Preparation Wizard (Schrödinger Suite 2009 Protein Preparation Wizard; Epik version 2.0, Schrödinger, LLC, New York, N.Y., 2009; Impact version 5.5, Schrödinger, LLC, New York, N.Y., 2009, Prime version 2.1, Schrödinger, LLC, New York, N.Y., 2009).

This structure was used as the model for the wild-type binding site without further changes.

The model of the G143A mutant was generated by changing a hydrogen in Glycine 143 of the wild-type model into a methyl group, thereby generating S-Alanine, using Schrödinger Maestro. Amino acids in a sphere of 5 Å around the co-crystallized molecule of azoxystrobin were energy-minimized using Schrödinger MacroModel (version 9.7, Schrödinger, LLC, New York, N.Y., 2009).

III.2 Molecular Docking

Structures of inhibitors were prepared for docking with Schrödinger LigPrep (version 2.3, Schrödinger, LLC, New York, N.Y., 2009) and docked into the structural models using Schrödinger Glide (version 5.5, Schrödinger, LLC, New York, N.Y., 2009).

III.3 Graphics of Inhibitors Bound to Cytochrome $bc_1$ Complex

Graphical representations of poses from the docking runs were generated using Molecular Operating Environment (MOE; 2010.10; Chemical Computing Group Inc., 1010 Sherbooke St. West, Suite #910, Montreal, QC, Canada, H3A 2R7, 2010) and refined using the GNU Image Manipulation Program (GIMP, version 2.6.8, 2008).

As illustrated in FIG. 1 molecular modelling of an artificial Qo inhibitor-resistant cytochrome $bc_1$ complex with the mutation G143A (see below for details) has been carried out. Docking of the commercial storbilurine analogue compound pyraclostrobin shows the steric clash resulting in impaired binding of this active ingredient in the G143A mutant cytochrome $bc_1$ complex. The compounds of the present invention largely avoid this steric clash by either replacing the central phenyl ring of pyraclostrobin with a smaller and/or more flexible two carbon unit which may be suitably substituted or by replacing the well known pharmacophores with the smaller tetrazolinone moiety R4-7.

III.4 Number of Van-Der-Waals Clashes Between Inhibitors and Alanine G143A

The docked ligands were transferred to the G143A binding site model keeping the coordinates from docking into the wild-type model. Thereby, complexes between the G143A binding site and ligands were formed. Those were used as starting structures for the following energy minimization using Schrödinger MacroModel. During these simulations, only the ligand was allowed to move freely, the protein was considered "frozen". The poses generated by this procedure were considered as the relaxed state of the inhibitors after introduction of the G143A mutation.

Two atoms are considered to be sterically clashing, if the distance between their centers is shorter than 0.9 times the sum of their Van-der-Waals radii. For the atoms pairs relevant for strobilurin interaction with Alanine 143 the respective distances are described in Table V.

TABLE V

| Atom 1 | vdW-Radius 1 | Atom 2 | vdW-Radius 2 | vdW-Sum | Clash Distance |
|---|---|---|---|---|---|
| C | 1.70 | C | 1.70 | 3.40 | 3.06 |
| C | 1.70 | N | 1.55 | 3.25 | 2.93 |
| C | 1.70 | O | 1.52 | 3.22 | 2.90 |
| C | 1.70 | H | 1.20 | 2.90 | 2.61 |
| H | 1.20 | N | 1.55 | 2.75 | 2.48 |
| H | 1.20 | O | 1.52 | 2.72 | 2.45 |

After mimization in the G143A binding site as described above, the number of steric Van-der-Waals clashes with Alanine 143 was counted for each inhibitor. The results are given in the Table VI.

TABLE VI

| Compound | No. of clashes |
|---|---|
| I-5 | 3 |
| I-6 | 3 |
| Pyrametostrobin | 6 |

TABLE VI-continued

| Compound | No. of clashes |
|---|---|
| Metominostrobin | 6 |
| Azoxystrobin | 7 |
| Enestroburin | 7 |
| Pyraclostrobin | 7 |
| Dimoxystrobin | 7 |
| Orysastrobin | 7 |
| Pyraoxystrobin | 8 |
| Picoxystrobin | 8 |
| Trifloxystrobin | 8 |
| Kresoxim-Methyl | 8 |

It was found that compounds I have a small number of steric Van-der-Waals clashes and also have unexpectedly high activity against Qo inhibitor-resistant fungal strains harboring said G143A mutation in microtiter titer tests as well as in field trials on sites which have a high portion of Qo inhibitor-resistant fungi strains harboring said G143A mutation (see below).

The invention claimed is:

1. A method for combating phytopathogenic fungi containing a mutation in the mitochondrial cytochrome b gene conferring resistance to Qo inhibitors, wherein the mutation is G143A, comprising applying a pesticidally effective amount of compound of formula (I)

wherein:
$R^1$, $R^2$ independently of each other are selected from the group consisting of hydrogen, halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl and $C_3$-$C_6$-cycloalkyl-$C_1$-$C_4$-alkyl, wherein the groups $R^1$ and $R^2$ are cis-oriented, or $R^1$ and $R^2$ together with the two carbon atoms linking them form a phenyl ring provided that $R^4$ is 4-methyl-1,4-dihydro-tetrazol-5-one-1-yl, and
  wherein the aliphatic moieties of $R^1$ and/or $R^2$ or the above-mentioned phenyl ring may carry 1, 2, 3 or up to the maximum number of identical or different groups $R^a$ which independently of one another are selected from the group consisting of:
$R^a$ halogen, CN, nitro, $C_1$-$C_4$-alkyl, $C_1$-$C_4$-alkoxy, $C_1$-$C_4$-haloalkyl and $C_1$-$C_4$-haloalkoxy;
Y is a direct bond or a divalent group selected from the group consisting of —OCH$_2$—, —CH$_2$—, —CH$_2$CH$_2$—, —C(Z)=N—O—CH$_2$—, —CHZ—C(Z)=N—O—CH$_2$—, —O—N=C(Z)—C(Z)=N—O—CH$_2$—, —C(=O)—C(Z)=N—O—CH$_2$— and —C(=N—O—Z)—C(Z)=N—O—CH$_2$—, where the bond depicted on the left side of the divalent group Y is attached to $R^3$, and the bond depicted on the right side is attached to the carbon atom being substituted by $R^2$, and Z, which may be the same or different to any other Z, is hydrogen, $C_1$-$C_4$-alkyl or $C_1$-$C_4$-haloalkyl;
$R^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group consisting of N, O and S;

wherein the cyclic groups $R^3$ may carry 1, 2, 3, 4 or up to the maximum possible number of identical or different groups $R^b$ which independently of one another are selected from:

$R^b$, which may be the same or different to any other $R^b$, is selected from the group consisting of amino, halogen, hydroxyl, oxo, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, naphthyl and a 3- to 10-membered saturated, partially unsaturated or aromatic mono- or bicyclic heterocyclyl which, in addition to carbon atoms, contains one to four heteroatoms selected from the group consisting of N, O and S as ring members; and wherein the aforementioned phenyl and heterocyclyl groups $R^b$ are attached via a direct bond, an oxygen or sulfur atom, and two radicals $R^b$ that are bound to adjacent ring member atoms of the cyclic group $R^3$ may form together with said ring member atoms a fused 5-, 6- or 7-membered saturated, partially unsaturated or aromatic cycle, which may be a carbocycle or heterocycle, wherein the ring member atoms of the heterocycle include besides carbon atoms 1, 2, 3 or 4 heteroatoms selected from the group consisting of N, O and S, and where the aliphatic or cyclic groups $R^b$ for their part may carry 1, 2, 3 or up to the maximum possible number of identical or different groups $R^c$:

$R^c$, which may be the same or different to any other $R^c$, is selected from the group consisting of halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups $R^c$ are attached via a direct bond, an oxygen or sulfur atom, and where the aliphatic or cyclic groups $R^c$ for their part may carry 1, 2, 3 or up to the maximum possible number of identical or different groups $R^d$:

$R^d$, which may be the same or different to any other $R^d$, is selected from the group consisting of halogen, $C_1$-$C_4$-alkyl and $C_1$-$C_4$-haloalkyl;

or $R^3$ is —$CR^A$=N—O—$R^B$, wherein $R^A$ is selected from the group consisting of amino, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_4$-alkoxy- imino-$C_1$-$C_4$-alkyl, $C_1$-$C_4$-alkylamino, $C_1$-$C_4$-alkoxycarbonyl, $C_1$-$C_4$-alkylcarbonyloxy, phenyl, phenyl-$C_1$-$C_4$-alkyl, naphthyl and a 3- to 10-membered saturated, partially unsaturated or aromatic mono- or bicyclic heterocyclyl or which, in addition to carbon atoms, contains one to four heteroatoms selected from the group consisting of O, N and S as ring members; and wherein the aforementioned cyclic $R^A$ are attached via a direct bond, an oxygen or sulfur atom;

$R^B$ is selected from the group consisting of $C_1$-$C_4$-alkyl, $C_2$-$C_4$-alkenyl, $C_2$-$C_4$-alkynyl, $C_1$-$C_4$-haloalkyl, $C_3$-$C_6$-cycloalkyl, $C_3$-$C_6$-cycloalkenyl, $C_1$-$C_4$-alkoxyimino-$C_1$-$C_4$-alkyl, $C_1$-$C_4$-alkoxycarbonyl, phenyl, phenyl-$C_1$-$C_4$-alkyl, naphthyl and a 3- to 10-membered saturated, partially unsaturated or aromatic mono- or bicyclic heterocyclyl or which, in addition to carbon atoms, contains one to four heteroatoms selected from the group consisting of O, N and S as ring members;

where the aliphatic or cyclic groups $R^A$ and/or $R^B$ for their part may carry 1, 2, 3 or up to the maximum possible number of identical or different groups $R^e$:

$R^e$, which may be the same or different to any other $R^e$, is selected from the group consisting of halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy and $C_1$-$C_4$-haloalkoxy;

$R^4$ is a monovalent group selected from formulae R4-1 to R4-7

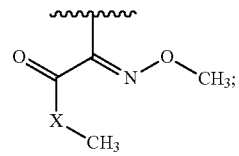

R4-1

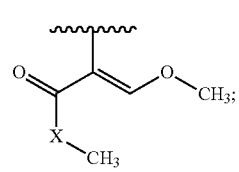

R4-2

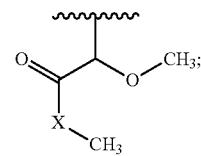

R4-3

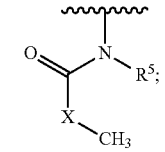

R4-4

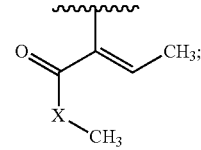

R4-5

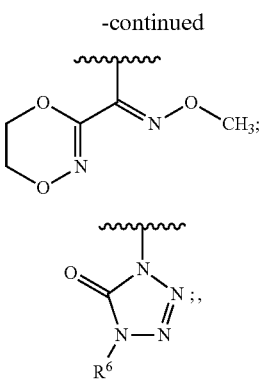

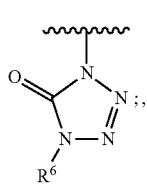

wherein the jagged line defines the point of attachment, and

X is a direct bond or a divalent group $CH_2$, O or NH, $R^5$ is selected from the group consisting of $C_1$-$C_4$-alkyl, $C_1$-$C_4$-alkoxy, $C_1$-$C_4$-haloalkyl, $C_1$-$C_4$-haloalkoxy and $C_3$-$C_6$-cycloalkyl, $R^6$ is $C_1$-$C_4$-alkyl or $C_1$-$C_4$-haloalkyl;

and the N-oxides and the agriculturally acceptable salts thereof.

2. The method of claim 1, wherein the phytopathogenic fungi are selected from the group consisting of *Alternaria alternata, Blumeria graminis, Pyriculania oryzae, Septoria tritici, Mycosphaerella fijiensis, Venturia inaequalis, Pyrenophora teres, Pyrenophona tritici-repentis* and *Plasmopara viticola*.

3. The method of claim 2, wherein the phytopathogenic fungus is *Septoria tritici*.

4. The method of claim 1, comprising:
treating the phytopathogenic fungi or the materials, plants, the soil or seeds that are at risk of being diseased from phytopathogenic fungi with an effective amount of at least one compound of formula I, or a composition comprising it thereof.

5. The method of claim 4, comprising:
a) identifying the phytopathogenic fungi, or the materials, plants, the soil or seeds that are at risk of being diseased from phytopathogenic fungi,
and
b) treating said fungi or the materials, plants, the soil or seeds with an effective amount of at least one compound of formula I, or a composition comprising it thereof.

6. A compound of formula (I)

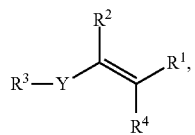

wherein:

$R^1$, $R^2$ independently of each other are selected from the group consisting of hydrogen, halogen, $C_1$-$C_4$-alkyl, $C_1$-$C_4$-alkoxy, $C_2$-$C_6$-alkenyl, $C_2$-$C_6$-alkenyloxy, $C_2$-$C_6$-alkynyl, $C_3$-$C_6$-cycloalkyl and $C_3$-$C_6$-cycloalkyl-$C_1$-$C_4$-alkyl, wherein the groups $R^1$ and $R^2$ are cis-oriented, wherein the aliphatic moieties of $R^1$ and/or $R^2$ may carry 1, 2, 3 or up to the maximum number of identical or different groups $R^a$ which independently of one another are selected from:

$R^a$ is selected from the group consisting of halogen, CN, nitro, $C_1$-$C_4$-alkyl, $C_1$-$C_4$-alkoxy, $C_1$-$C_4$-haloalkyl and $C_1$-$C_4$-haloalkoxy;

Y is a direct bond or a divalent group selected from the group consisting of —$OCH_2$—, —$CH_2$—, —$CH_2CH_2$—, —C(Z)=N—O—$CH_2$—, —CHZ—C(Z)=N—O—$CH_2$—, —O—N=C(Z)—C(Z)=N—O—$CH_2$—, —C(=O)—C(Z)=N—O—$CH_2$— and —C(=N—O—Z)—C(Z)=N—O—$CH_2$—, where the bond depicted on the left side of the divalent group Y is attached to $R^3$, and the bond depicted on the right side is attached to the carbon atom being substituted by $R^2$, and Z, which may be the same or different to any other Z, is $C_1$-$C_4$-alkyl or $C_1$-$C_4$-haloalkyl;

$R^3$ is phenyl or a 3- to 10-membered saturated, partially unsaturated or aromatic mono- or bicyclic heterocyclyl wherein the ring member atoms of the heterocyclyl include besides carbon atoms 1, 2, 3 or 4 heteroatoms selected from the group consisting of N, O and S;

wherein the cyclic groups $R^3$ may carry 1, 2, 3, 4 or up to the maximum possible number of identical or different groups $R^b$ which independently of one another are selected from the group consisting of:

$R^b$, which may be the same or different to any other $R^b$, is selected from the group consisting of amino, halogen, hydroxyl, oxo, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, naphthyl and a 3- to 10-membered saturated, partially unsaturated or aromatic mono- or bicyclic heterocyclyl or which, in addition to carbon atoms, contains one to four heteroatoms selected from the group consisting of N, O and S as ring members; and wherein the aforementioned phenyl and heterocyclyl groups $R^b$ are attached via a direct bond, an oxygen or sulfur atom;
and two radicals $R^b$ that are bound to adjacent ring member atoms of the cyclic group $R^3$ may form together with said ring member atoms a fused 5-, 6- or 7-membered saturated, partially unsaturated or aromatic cycle, which may be a carbocycle or heterocycle, wherein the ring member atoms of the fused heterocycle include besides carbon atoms 1, 2, 3 or 4 heteroatoms selected from the group consisting of N, O and S, and where the aliphatic or cyclic groups $R^b$ for their part may carry 1, 2, 3 or up to the maximum possible number of identical or different groups $R^c$:

$R^c$, which may be the same or different to any other $R^c$, is selected from the group consisting of halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkoxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, phenyl and a 5-membered saturated, partially unsaturated or aromatic heterocyclyl which, in addition to carbon atoms, contains one to three heteroatoms selected from the group consisting of N, O and S as ring members; wherein the aforementioned cyclic groups $R^c$ are attached via a direct bond, an oxygen or sulfur atom and where the aliphatic or cyclic groups $R^c$ for their part may carry 1, 2, 3 or up to the maximum possible number of identical or different groups $R^d$:

$R^d$, which may be the same or different to any other $R^d$, is selected from the group consisting of halogen, $C_1$-$C_4$-alkyl and $C_1$-$C_4$-haloalkyl;

or $R^3$ is —$CR^A$=N—O—$R^B$, wherein $R^A$ is selected from the group consisting of amino, hydroxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkenyl, $C_2$-$C_6$-alkenyloxy, $C_3$-$C_6$-alkynyloxy, $C_1$-$C_4$-alkoxyimino-$C_1$-$C_4$-alkyl, $C_1$-$C_4$-alkylamino, $C_1$-$C_4$-alkoxycarbonyl, $C_1$-$C_4$-alkylcarbonyloxy, phenyl, phenyl-$C_1$-$C_4$-alkyl, naphthyl and a 3- to 10-membered saturated, partially unsaturated or aromatic mono- or bicyclic heterocyclyl or which, in addition to carbon atoms, contains one to four heteroatoms from the group consisting of O, N and S as ring members; and wherein the aforementioned cyclic $R^A$ are attached via a direct bond, an oxygen or sulfur atom;

$R^B$ is selected from the group consisting of $C_1$-$C_4$-alkyl, $C_2$-$C_4$-alkenyl, $C_2$-$C_4$-alkynyl, $C_1$-$C_4$-haloalkyl, $C_3$-$C_6$-cycloalkyl, $C_3$-$C_6$-cycloalkenyl, $CC_1$-$C_4$-alkoxyimino-$C_1$-$C_4$-alkyl, $C_1$-$C_4$-alkoxycarbonyl, phenyl, phenyl-$C_1$-$C_4$-alkyl, naphthyl and a 3- to 10-membered saturated, partially unsaturated or aromatic mono- or bicyclic heterocyclyl or which, in addition to carbon atoms, contains one to four heteroatoms from the group consisting of O, N and S as ring members;

where the aliphatic or cyclic groups $R^A$ and/or $R^B$ for their part may carry 1, 2, 3 or up to the maximum possible number of identical or different groups $R^e$:

$R^e$, which may be the same or different to any other $R^e$, is selected from the group consisting of halogen, hydroxyl, nitro, CN, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy and $C_1$-$C_4$-haloalkoxy;

$R^4$ is a monovalent group selected from formulae R4-1 to R4-7

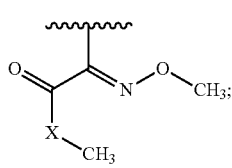

R4-1

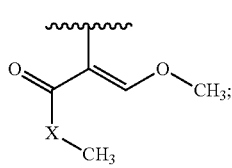

R4-2

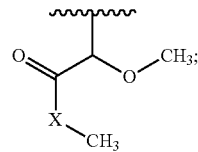

R4-3

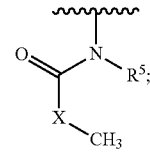

R4-4

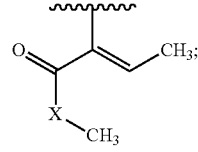

R4-5

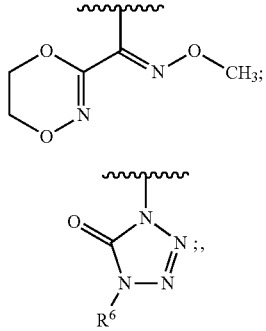

R4-6

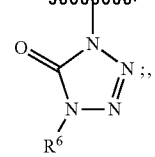

R4-7 wherein the jagged line defines the point of attachment, and where

X is a divalent group O or NH, $R^5$ is selected from the group consisting of $C_1$-$C_4$-alkyl, $C_1$-$C_4$-alkoxy, $C_1$-$C_4$-haloalkyl, $C_1$-$C_4$-haloalkoxy and $C_3$-$C_6$-cycloalkyl, $R^6$ is $C_1$-$C_4$-alkyl or $C_1$-$C_4$-haloalkyl;

and the N-oxides and the agriculturally acceptable salts thereof, except for (E)-2-[1-methoxy-meth-(E)-ylidene]-5-(4-phenoxy-phenoxy)-3-trifluoromethyl-pent-3-enoic acid methyl ester, (E)-2-[1-methoxy-meth-(E)-ylidene]-5-(3-phenoxy-phenoxy)-3-trifluoromethyl-pent-3-enoic acid methyl ester (207853-00-7); (E)-2-[1-methoxy-meth-(E)-ylidene]-4-methyl-5-(3-phenoxy-phenoxy)-3-trifluoromethyl-pent-3-enoic acid methyl ester, (E)-5,5,5-trifluoro-2-[1-methoxy-meth-(E)-ylidene]-3-methyl-4-(4-phenoxy-phenoxymethyl)-pent-3-enoic acid methyl ester, and (2E,3Z)-2-(ethylidene)-5-phenyl-3-pentenoic acid methyl ester.

7. The compound of claim 6, with the proviso that $R^1$ is not $CF_3$ if $R^4$ is 1-methoxycarbonyl-2-methoxy-ethen-1-yl.

8. The compound of claim 6, wherein $R^1$ is selected from the group consisting of hydrogen, halogen, $C_1$-$C_4$-alkyl, $C_1$-$C_4$-chloroalkyl, $C_1$-$C_4$-alkoxy, $C_1$-$C_4$-alkoxy-$C_1$-$C_4$-alkyl and $C_1$-$C_4$-haloalkoxy-$C_1$-$C_4$-alkyl.

9. The compound of claim 8, wherein $R^1$ is methyl or ethyl.

10. The compound of claim 6, wherein $R^2$ is hydrogen.

11. The compound of claim 6, wherein Y is selected from the group consisting of —$OCH_2$—, —$CH_2CH_2$—, —$C(CH_3)$=N—O—$CH_2$—, —O—N=$C(CH_3)$—$C(CH_3)$=N—O—$CH_2$— and —C(=N—O—$CH_3$)—$C(CH_3)$=N—O—$CH_2$—.

12. The compound of claim 6, wherein $R^3$ is selected from the group consisting of pyrazolyl, imidazolyl, oxazolyl, isoxazolyl, thiazolyl, 1,2,4-triazolyl, 1,2,4-oxadiazolyl, 1,3,4-oxadiazolyl and 1,2,4-thiadiazolyl, which is substituted by phenyl, wherein said phenyl may carry 1, 2, 3 or up to the maximum possible number of identical or different groups $R^c$:

$R^c$, which may be the same or different to any other $R^c$, is selected from the group consisting of halogen, $C_1$-$C_4$-alkyl, $C_2$-$C_4$-alkenyl, $C_1$-$C_4$-haloalkyl, $C_1$-$C_4$-alkoxy, $C_1$-$C_4$-haloalkoxy, $C_1$-$C_4$-alkoxyimino-$C_1$-$C_4$-alkyl, phenyl and a 5-membered saturated, partially unsaturated or aromatic heterocyclyl which, in addition to carbon atoms, contains one to three heteroatoms selected from the group consisting of N, O and S as ring members; and wherein the aforementioned heterocyclyl groups $R^c$ are attached via a direct bond, an oxygen or sulfur atom and for their part may carry 1, 2, 3 or up to the maximum possible number of identical or different groups $R^d$.

13. The compound of claim 6, wherein $R^4$ is selected from the group consisting of —C(=NOCH$_3$)—CONHCH$_3$, —C(=NOCH$_3$)—COOCH$_3$, —C(=CHOCH$_3$)—COOCH$_3$, —C(=CHOCH$_3$)—CONHCH$_3$, —N(OCH$_3$)—COOCH$_3$, —N(CH$_3$)—COOCH$_3$ and —N(CH$_2$CH$_3$)—COOCH$_3$.

14. An agrochemical composition comprising an auxiliary and at least one compound of formula I, as defined in claim 6, an N-oxide or an agriculturally acceptable salt thereof.

15. The composition of claim 14 comprising at least one further active substance.

16. The composition of claim 15, wherein the further active substance is selected from the classes A) to O):

A) Respiration inhibitors
Inhibitors of complex III at $Q_o$ site: azoxystrobin, coumethoxystrobin, coumoxystrobin, dimoxystrobin, enestroburin, fenaminstrobin, fenoxy-strobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;
inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl] amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;
inhibitors of complex II: benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;
other respiration inhibitors: diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors
C14 demethylase inhibitors: triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chloro-phenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine; Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic acid synthesis inhibitors
phenylamides or acyl amino acid fungicides: benalaxyl, benalaxyl-M, kiralaxyl, metalaxyl, metalaxyl-M, ofurace, oxadixyl;
others: hymexazole, octhilinone, oxolinic acid, bupirimate, 5-fluorocytosine, 5-fluoro-2-(p-tolylmethoxy) pyrimidin-4-amine, 5-fluoro-2-(4-fluorophenyl-meth-oxy)pyrimidin-4-amine;

D) Inhibitors of cell division and cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of amino acid and protein synthesis
methionine synthesis inhibitors: cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal transduction inhibitors
  MAP/histidine kinase inhibitors: fluoroimid, iprodione, procymidone, vinclozolin, fenpiclonil, fludioxonil;
  G protein inhibitors: quinoxyfen;
G) Lipid and membrane synthesis inhibitors
  Phospholipid biosynthesis inhibitors: edifenphos, iprobenfos, pyrazophos, isoprothiolane;
  lipid peroxidation: dicloran, quintozene, tecnazene, tolclofos-methyl, biphenyl, chloroneb, etridiazole;
  phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
  compounds affecting cell membrane permeability and fatty acids: propamocarb, propamocarb-hydrochlorid;
  fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;
H) Inhibitors with Multi Site Action
  inorganic active substances: Bordeaux mixture, copper acetate, copper hydroxide, copper oxychloride, basic copper sulfate, sulfur;
  thio- and dithiocarbamates: ferbam, mancozeb, maneb, metam, metiram, propineb, thiram, zineb, ziram;
  organochlorine compounds: anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
  guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;
I) Cell wall synthesis inhibitors
  inhibitors of glucan synthesis: validamycin, polyoxin B;
  melanin synthesis inhibitors: pyroquilon, tricyclazole, carpropamid, dicyclomet, fenoxanil;
J) Plant defence inducers
  acibenzolar-S-methyl, probenazole, isotianil, tiadinil, prohexadione-calcium; phosphonates: fosetyl, fosetyl-aluminum, phosphorous acid and its salts;
K) Unknown mode of action
  bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxincopper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine, N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;
L) Antifungal biocontrol agents, plant bioactivators
  *Ampelomyces quisqualis, Aspergillus flavus, Aureobasidium pullulans, Bacillus pumilus, Bacillus subtilis, Bacillus subtilis* var. *amyloliquefaciens* FZB24, *Candida oleophila* 1-82, *Candida saitoana, Chitosan, Clonostachys rosea* f. *catenulata*, Coniothyrium minitans, Cryphonectria parasitica, Cryptococcus albidus, Fusarium oxysporum, Metschnikowia fructicola, Microdochium dimerum, Phlebiopsis gigantea, Pseudozyma flocculosa, Pythium oligandrum DV74, *Reynoutria sachlinensis, Talaromyces flavus* V117b, *Trichoderma asperellum* SKT-1, *T. atroviride* LC52, *T. harzianum* T-22, *T. harzianum* TH 35, *T. harzianum* T-39, *T. harzianum* and *T. viride, T. harzianum* ICC012 and *T. viride* ICC080, *T. polysporum* and *T. harzianum, T. stromaticum, T. virens* GL-21, *T. viride, T. viride* TV1, *Ulocladium oudemansii* HRU3;
M) Growth regulators
  abscisic acid, amidochlor, ancymidol, 6-benzylaminopurine, brassinolide, butralin, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat chloride, naphthaleneacetic acid, N-6-benzyladenine, paclobutrazol, prohexadione-calcium, prohydrojasmon, thidiazuron, triapenthenol, tributyl phosphorotrithioate, 2,3,5-tri-iodobenzoic acid, trinexapac-ethyl and uniconazole;
N) Herbicides
  acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
  amino acid derivatives: bilanafos, glyphosate, glufosinate, sulfosate;
  aryloxyphenoxypropionates: clodinafop, cyhalofop-butyl, fenoxaprop, fluazifop, haloxyfop, metamifop, propaquizafop, quizalofop, quizalofop-P-tefuryl;
  Bipyridyls: diquat, paraquat;
  (thio)carbamates: asulam, butylate, carbetamide, desmedipham, dimepiperate, eptam, esprocarb, molinate, orbencarb, phenmedipham, prosulfocarb, pyributicarb, thiobencarb, triallate;
  cyclohexanediones: butroxydim, clethodim, cycloxydim, profoxydim, sethoxydim, tepraloxydim, tralkoxydim;
  dinitroanilines: benfluralin, ethalfluralin, oryzalin, pendimethalin, prodiamine, trifluralin;
  diphenyl ethers: acifluorfen, aclonifen, bifenox, diclofop, ethoxyfen, fomesafen, lactofen, oxyfluorfen;
  hydroxybenzonitriles: bromoxynil, dichlobenil, ioxynil;
  imidazolinones: imazamethabenz, imazamox, imazapic, imazapyr, imazaquin, imazethapyr;
  phenoxy acetic acids: clomeprop, 2,4-dichlorophenoxyacetic acid, 2,4-DB, dichlorprop, MCPA, MCPA-thioethyl, MCPB, Mecoprop;

pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
others: benclothiaz, bifenazate, cartap, flonicamid, pyridalyl, pymetrozine, sulfur, thiocyclam, flubendiamide, chlorantraniliprole, cyazypyr, cyenopyrafen, flupyrazofos, cyflumetofen, amidoflumet, imicyafos, bistrifluron, and pyrifluquinazon.

17. The composition of claim 14, with the proviso that $R^1$ in the compound of formula I is not $CF_3$ if $R^4$ is 1-methoxycarbonyl-2-methoxy-ethen-1-yl.

18. The composition of claim 14, wherein $R^1$ in the compound of formula I is selected from the group consisting of hydrogen, halogen, $C_1$-$C_4$-alkyl, $C_1$-$C_4$-chloroalkyl, $C_1$-$C_4$-alkoxy, $C_1$-$C_4$-alkoxy-$C_1$-$C_4$-alkyl and $C_1$-$C_4$-haloalkoxy-$C_1$-$C_4$-alkyl.

19. The composition of claim 14, wherein $R^1$ in the compound of formula I is methyl or ethyl.

20. The composition of claim 14, wherein $R^2$ in the compound of formula I is hydrogen.

\* \* \* \* \*